United States Patent
Scott et al.

(10) Patent No.: US 7,481,782 B2
(45) Date of Patent: Jan. 27, 2009

(54) MOVEMENT FACILITATION DEVICE

(75) Inventors: Timothy Roderick Dalkeith Scott, New South Wales (AU); Veronica A. Vare, New South Wales (AU); Peter Puya Abolfathi, New South Wales (AU); Gordon G. Wallace, New South Wales (AU); Dezhi Zhou, New South Wales (AU)

(73) Assignee: Northern Sydney Area Health Service, Gosford NSW (AU)

( * ) Notice: Subject to any disclaimer, the term of this patent is extended or adjusted under 35 U.S.C. 154(b) by 206 days.

(21) Appl. No.: 10/526,713

(22) PCT Filed: Sep. 4, 2003

(86) PCT No.: PCT/AU03/01138

§ 371 (c)(1),
(2), (4) Date: Sep. 23, 2005

(87) PCT Pub. No.: WO2004/021936

PCT Pub. Date: Mar. 18, 2004

(65) Prior Publication Data

US 2006/0094989 A1 May 4, 2006

(30) Foreign Application Priority Data

Sep. 4, 2002 (AU) .............................. 2002951193

(51) Int. Cl.
*A61H 1/00* (2006.01)
*A61H 1/02* (2006.01)
*A61H 5/00* (2006.01)
*G01L 1/24* (2006.01)

(52) U.S. Cl. ................. 601/5; 601/33; 601/40; 73/862.624

(58) Field of Classification Search ............... 601/5, 601/23, 33–35, 40; 73/862.624
See application file for complete search history.

(56) References Cited

U.S. PATENT DOCUMENTS 4,167,044 A * 9/1979 Girard ................. 623/63
4,719,906 A * 1/1988 DeProspero ............. 602/21

(Continued)

FOREIGN PATENT DOCUMENTS

EP 924033 9/1996

(Continued)

*Primary Examiner*—Justine R. Yu
*Assistant Examiner*—Kristen C Matter
(74) *Attorney, Agent, or Firm*—Knobbe Martens Olson & Bear, LLP

(57) ABSTRACT

The present invention concerns movement facilitation devices for facilitating movement between a first portion of a first object and a second portion of the first object. One or more of the movement facilitation devices may be combined to form a movement device for facilitating movement of at least one joint or limb of a patient's body. One form of a movement device according to the invention is a glove which at least partially encloses the joint or limb. The invention also encompasses systems for applying Continuous Passive Motion therapy to a joint or limb of a patient using the devices of the invention. The invention also encompasses the use of shape memory materials and of conducting polymers in the devices and systems of the invention, as well as the design of force transducers and actuators that may be used in the devices.

3 Claims, 53 Drawing Sheets

U.S. PATENT DOCUMENTS

| | | |
|---|---|---|
| 4,875,469 A | 10/1989 | Brook et al. |
| 5,252,102 A * | 10/1993 | Singer et al. ................. 623/24 |
| 5,516,249 A * | 5/1996 | Brimhall ....................... 414/5 |
| 5,556,700 A | 9/1996 | Kaneto et al. |
| 5,683,351 A | 11/1997 | Kaiser et al. |
| 5,980,435 A * | 11/1999 | Joutras et al. ............... 482/114 |
| 6,312,398 B1 * | 11/2001 | Cencer ....................... 601/40 |
| 6,379,393 B1 * | 4/2002 | Mavroidis et al. ............. 623/25 |
| 6,554,472 B1 * | 4/2003 | Dietz et al. ................. 378/197 |
| 6,619,134 B1 * | 9/2003 | Kinnunen et al. ............. 73/800 |

FOREIGN PATENT DOCUMENTS

| | | |
|---|---|---|
| EP | 1364636 | 11/2003 |
| WO | WO 00/15157 | 3/2000 |

* cited by examiner

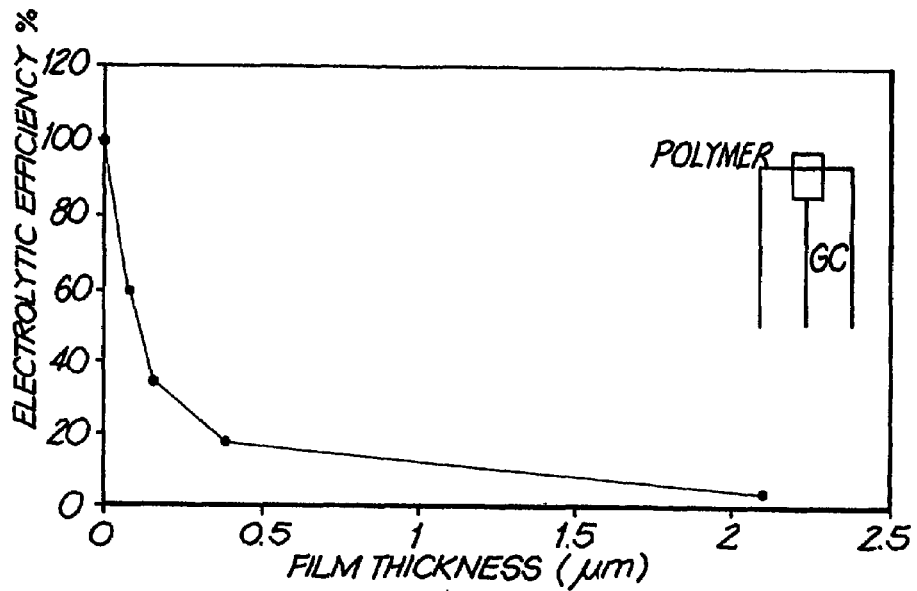
FIG. 6
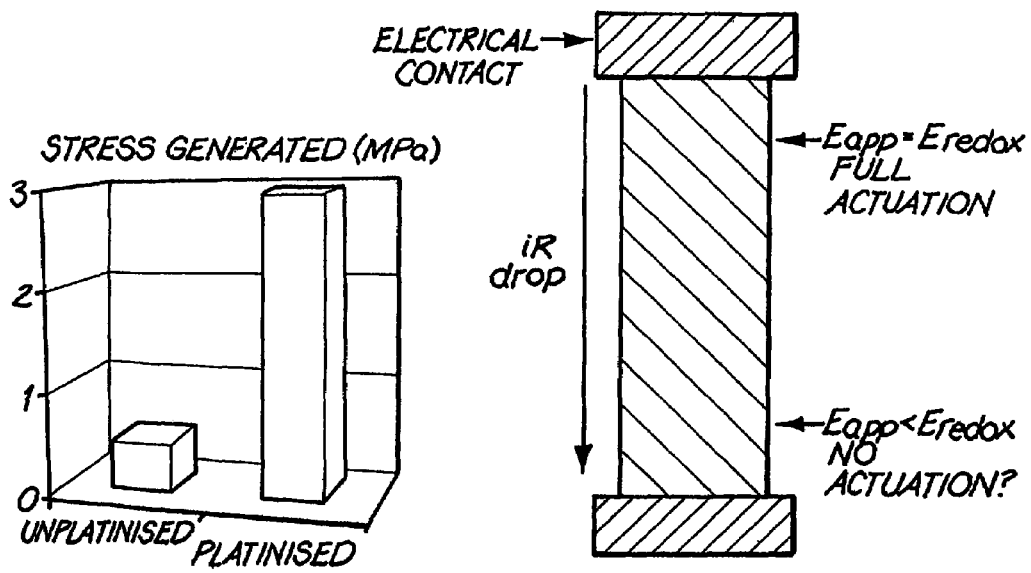
FIG. 7a
FIG. 7b (PART I)

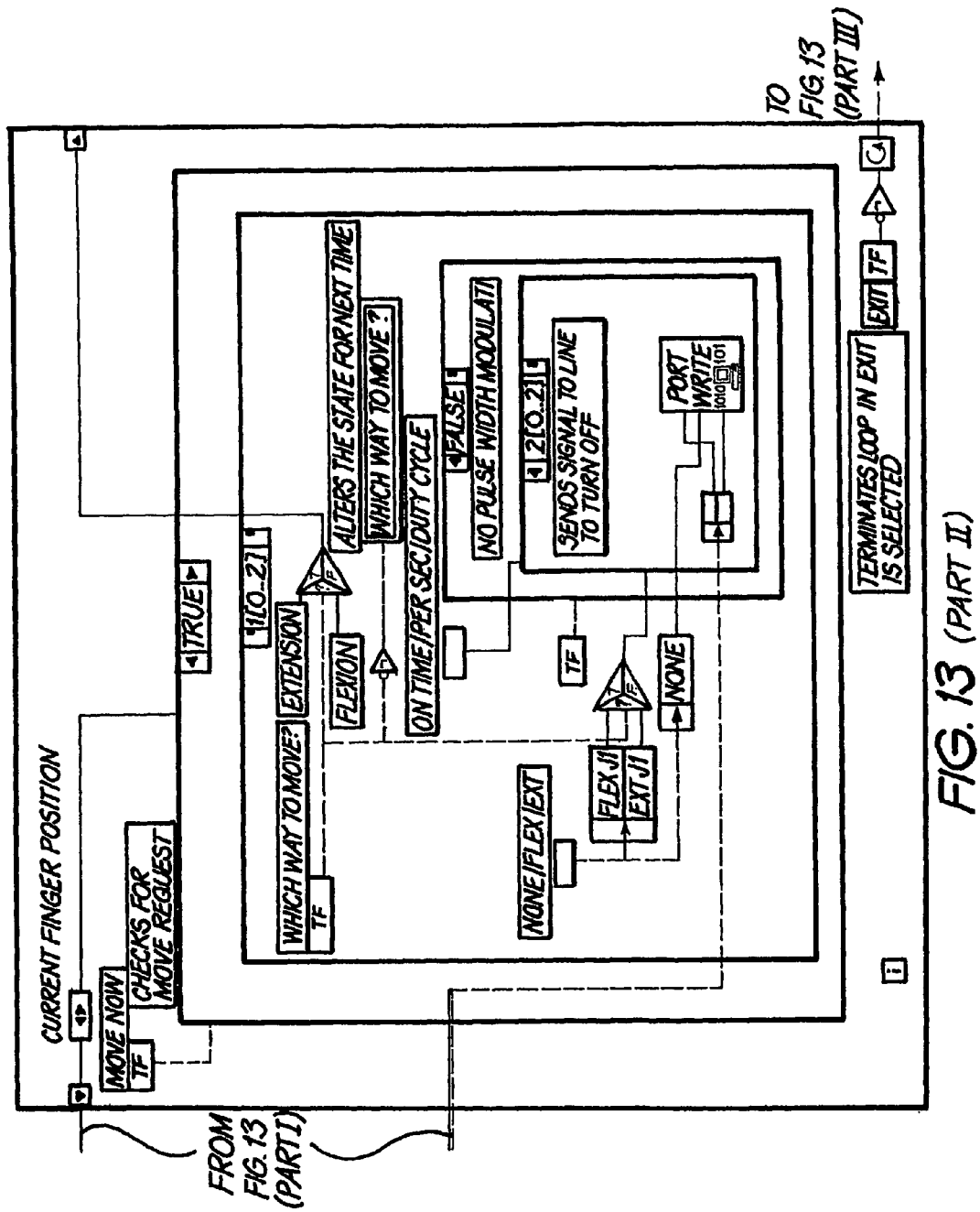
FIG. 13 (PART II)

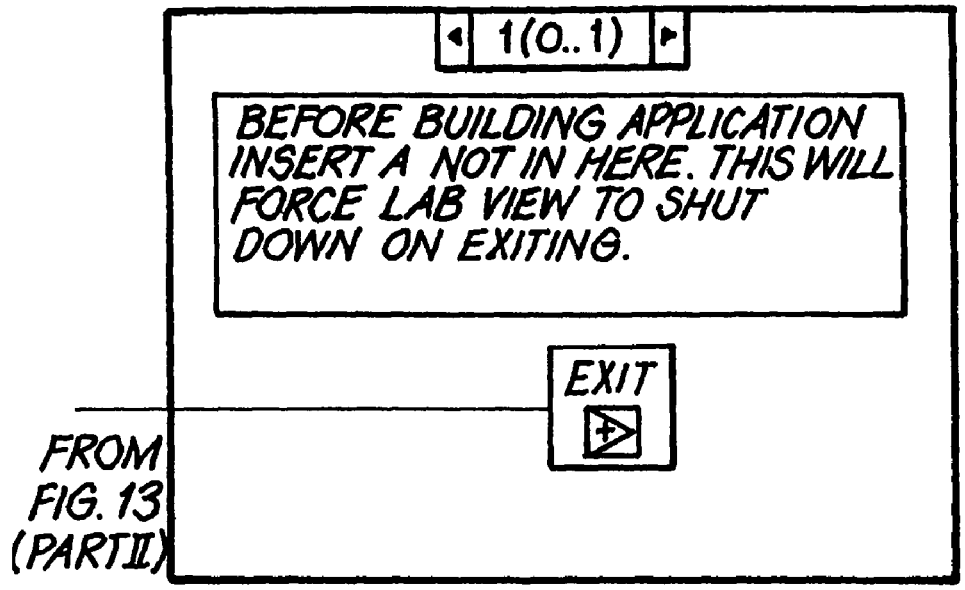
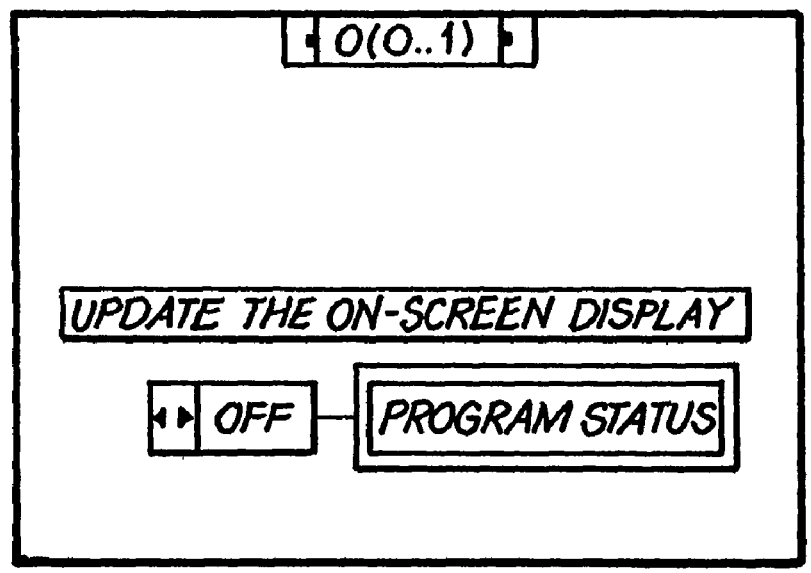
FIG. 13
(PART III)

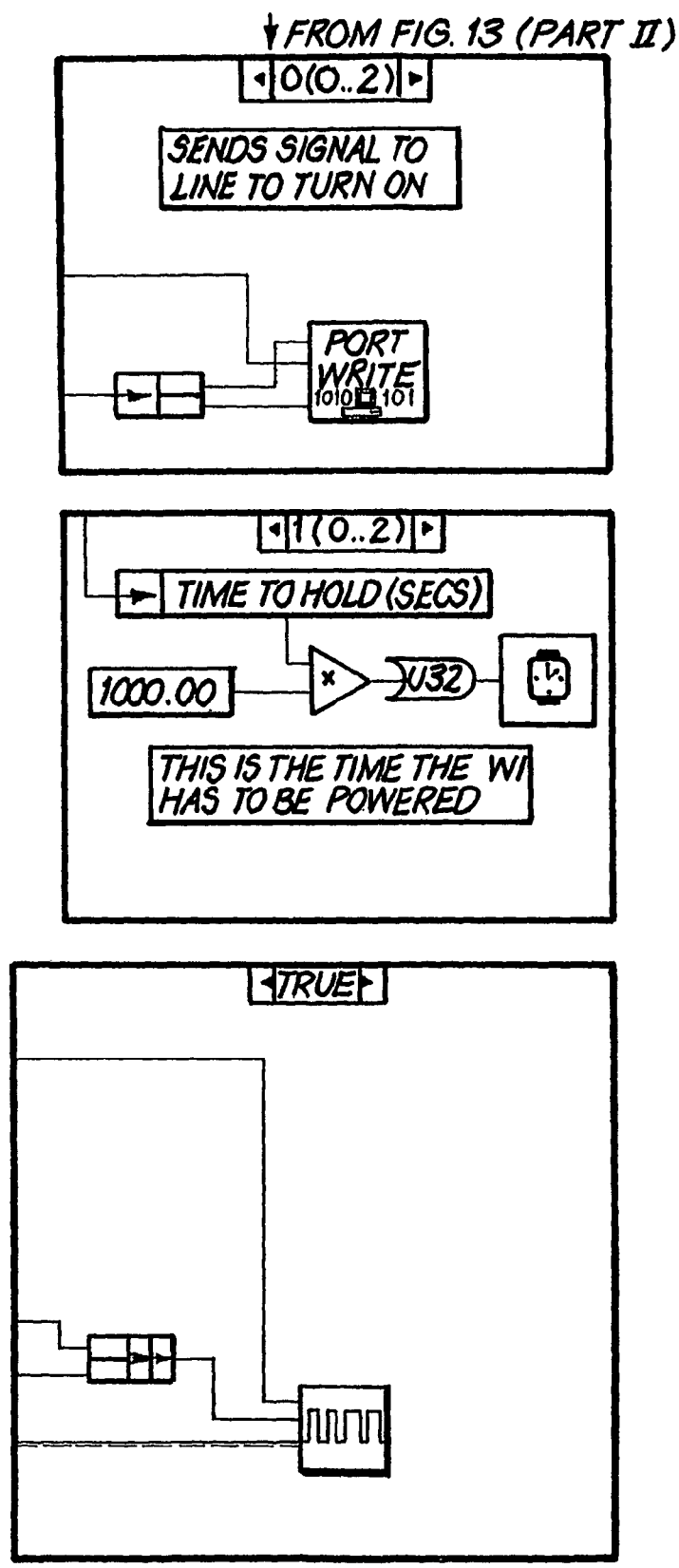
FIG. 13 (PART IV)

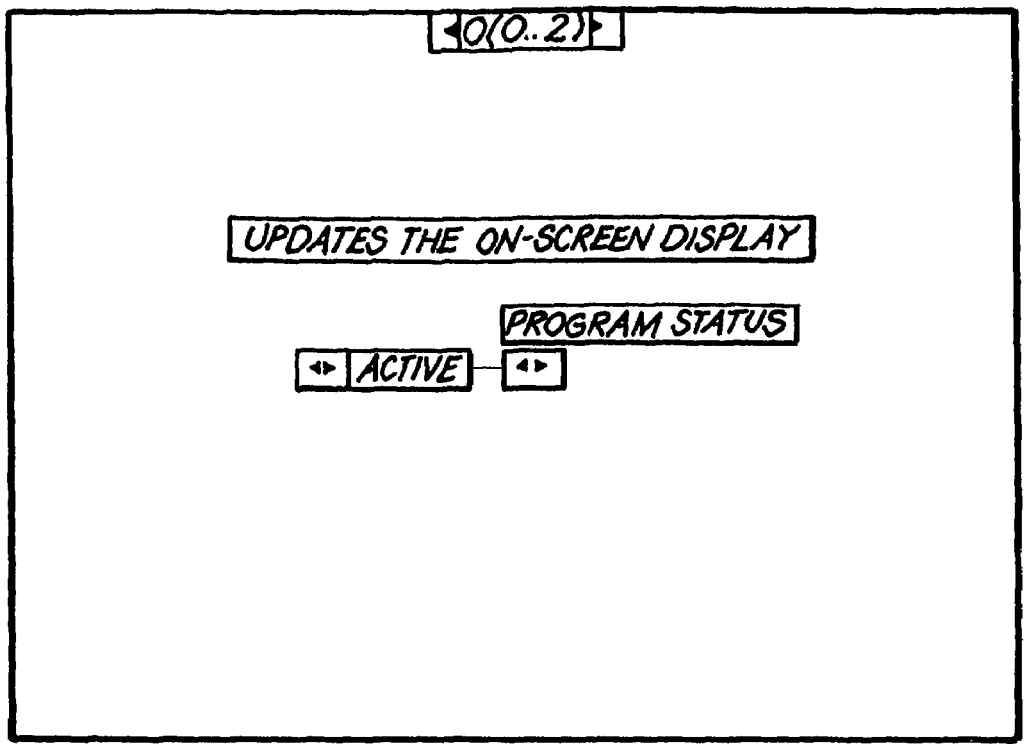
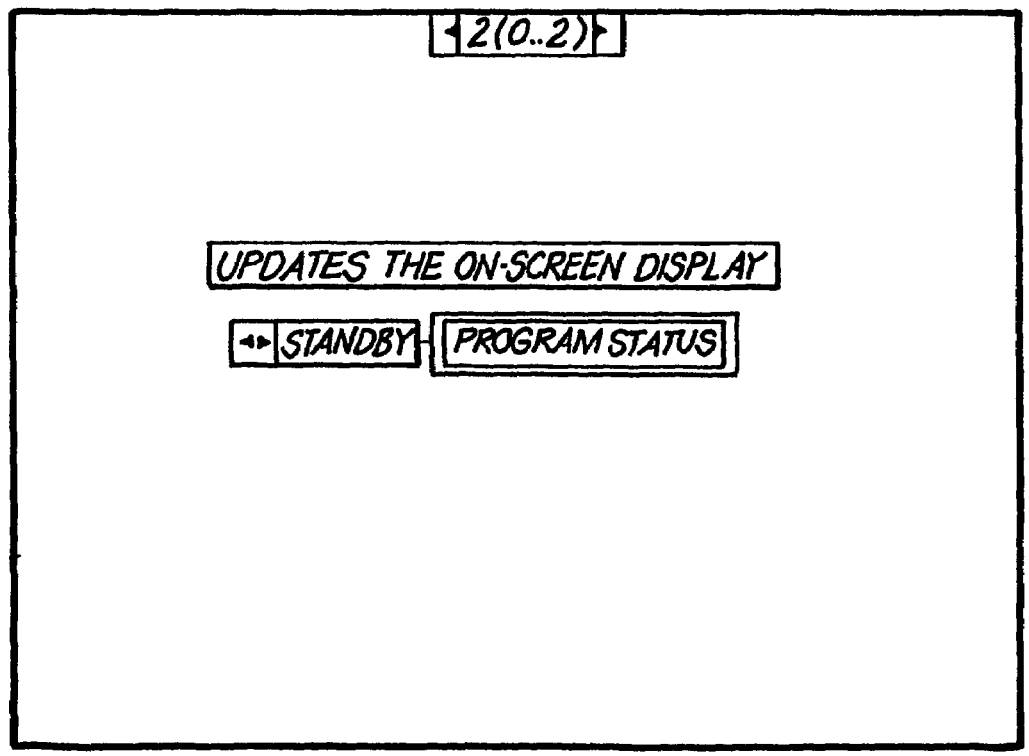
↑ TO FIG. 14 (PART II)
FIG. 14
(PART I)

↓FROM FIG. 14 (PART I)

◁FALSE▷

NO MOVE REQUESTED SO WAIT FOR 500ms
(HALF A SECOND) & THEN CHECK AGAIN

500 ─

(PART II)

(PART I)

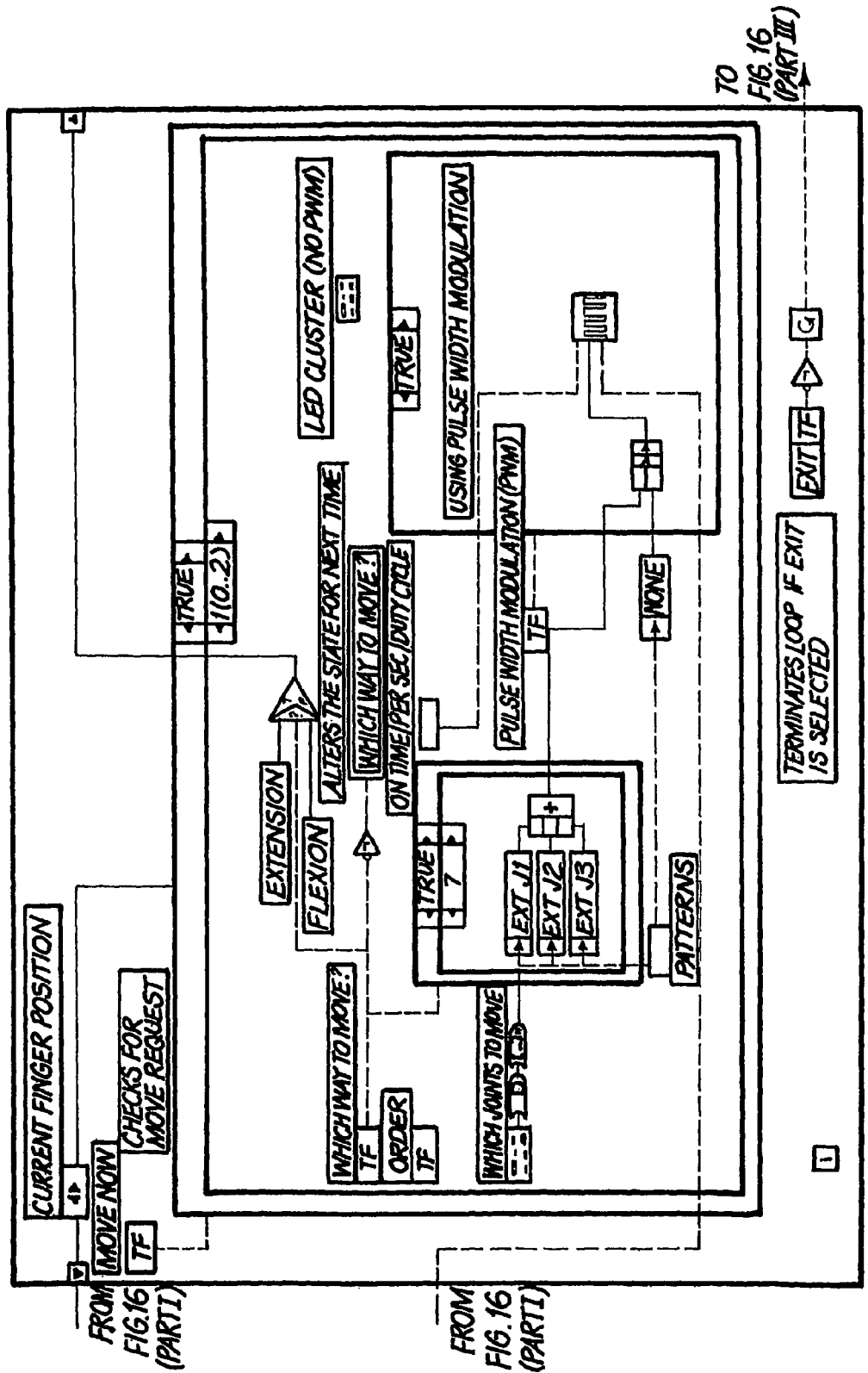
FIG. 16 (PART II)

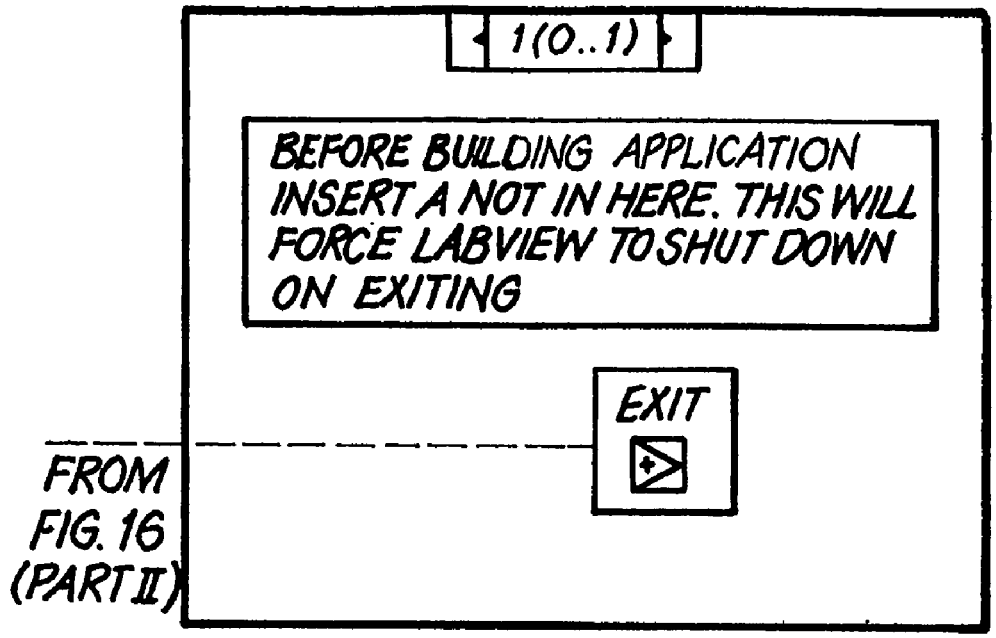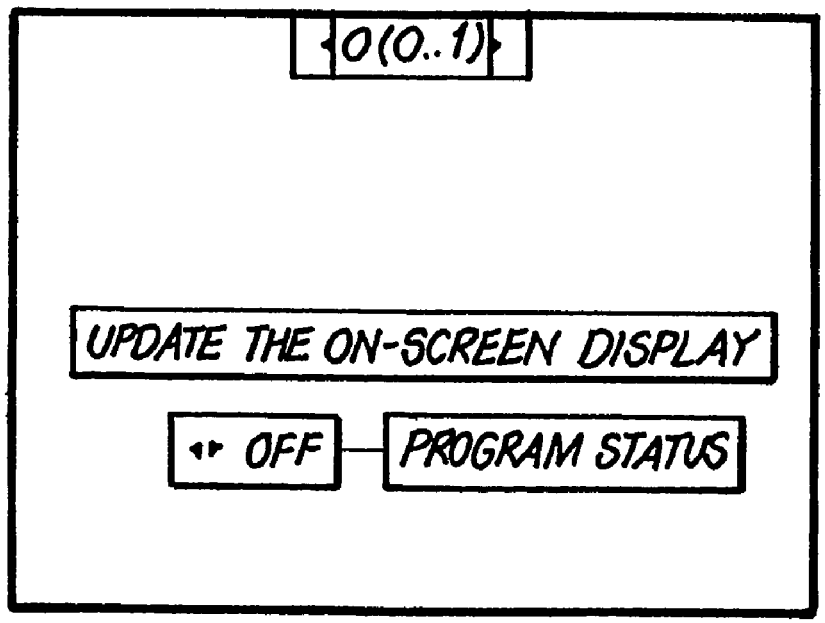
FIG. 16
(PART III)

(PART IV)

↑FROM FIG. 16 (PART IV)
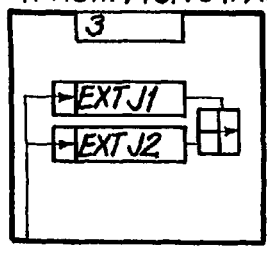
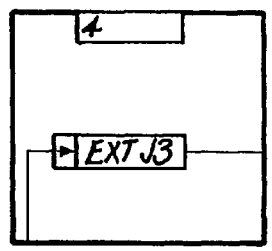
↑FROM FIG. 16 (PART IV)
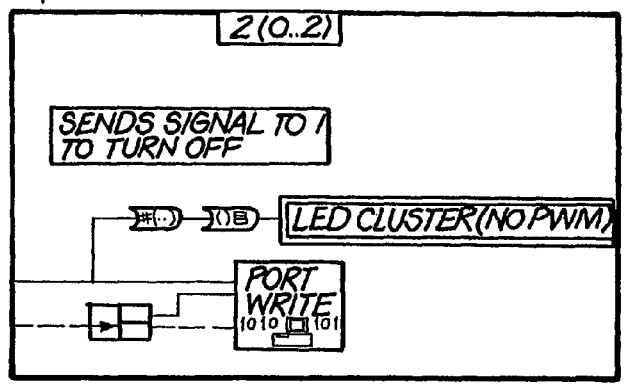
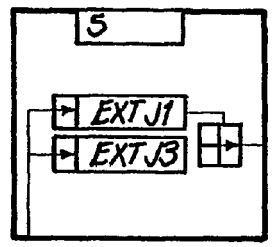
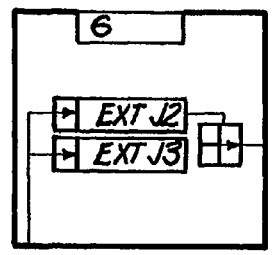
FIG. 16
(PART V)

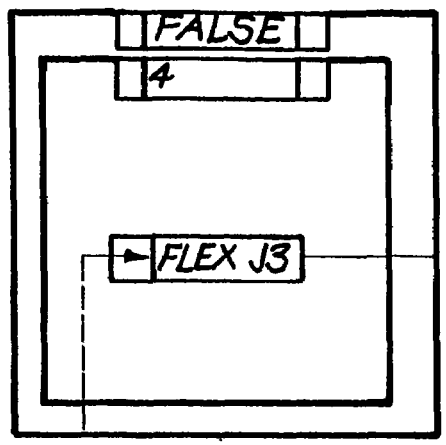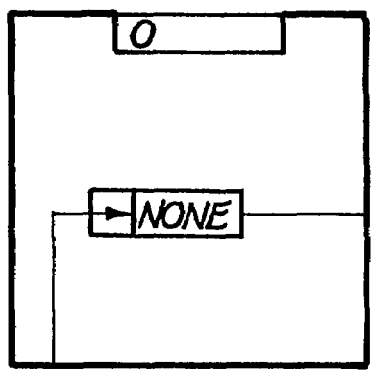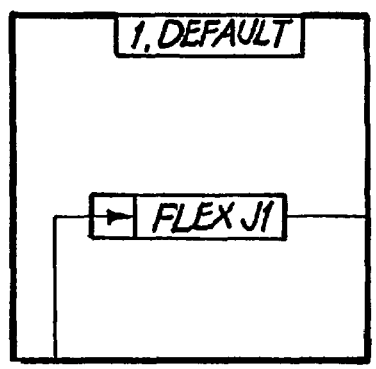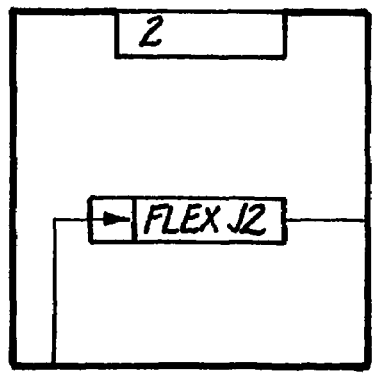
FIG. 18
(PART I)
↓ TO FIG. 18 (PART II)

↓FROM FIG. 18 (PART I)
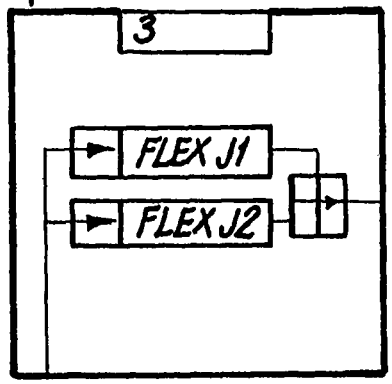
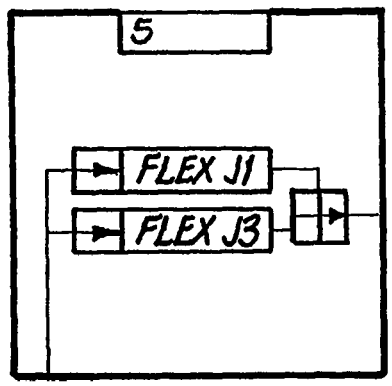
*FIG. 18*
*(PART II)*
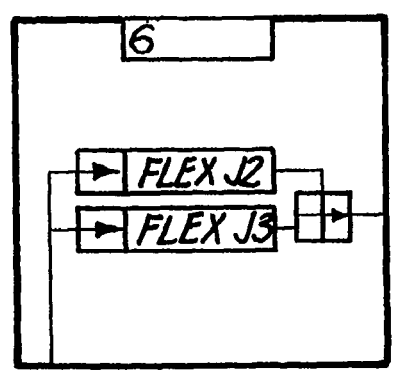
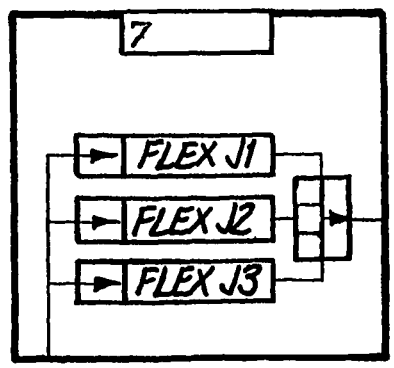
↓TO FIG. 18 (PART III)

(PART III)

FIG. 19

TIME / PER SEC / DUTY CYCLE

TIME TO HOLD (SECS)
2.0

CYCLES PER SECOND
10

% ON
50

TO SHOW POWER STATE

OFF
0

ON
0

LINE PATTERNS

ON PATTERN ×0
OFF PATTERN ×0

TASK ID / ERROR CLUSTER

TASK ID
×0

ERROR OUT
CODE
NO ERROR    0
SOURCE

FLOOR (x,y)  x-y
0    0

LED CLUSTER

| EXTENSORS | OFF | 6 | OFF | 4 | OFF | 2 | OFF | 0 |
| FLEXORS | OFF | 7 | OFF | 5 | OFF | 3 | OFF | 1 |

FIG. 20

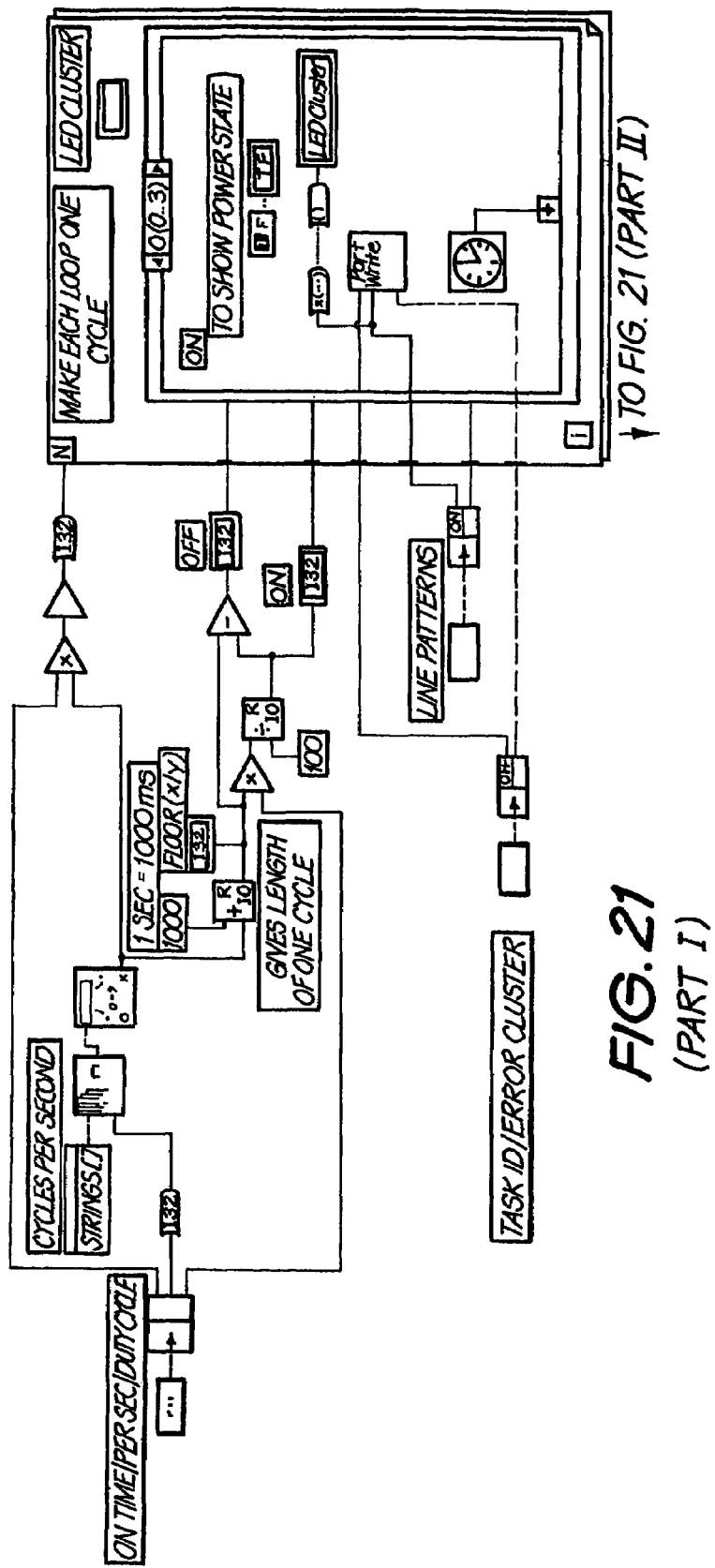
FIG. 21 (PART I)

(PART II)

(PART I)

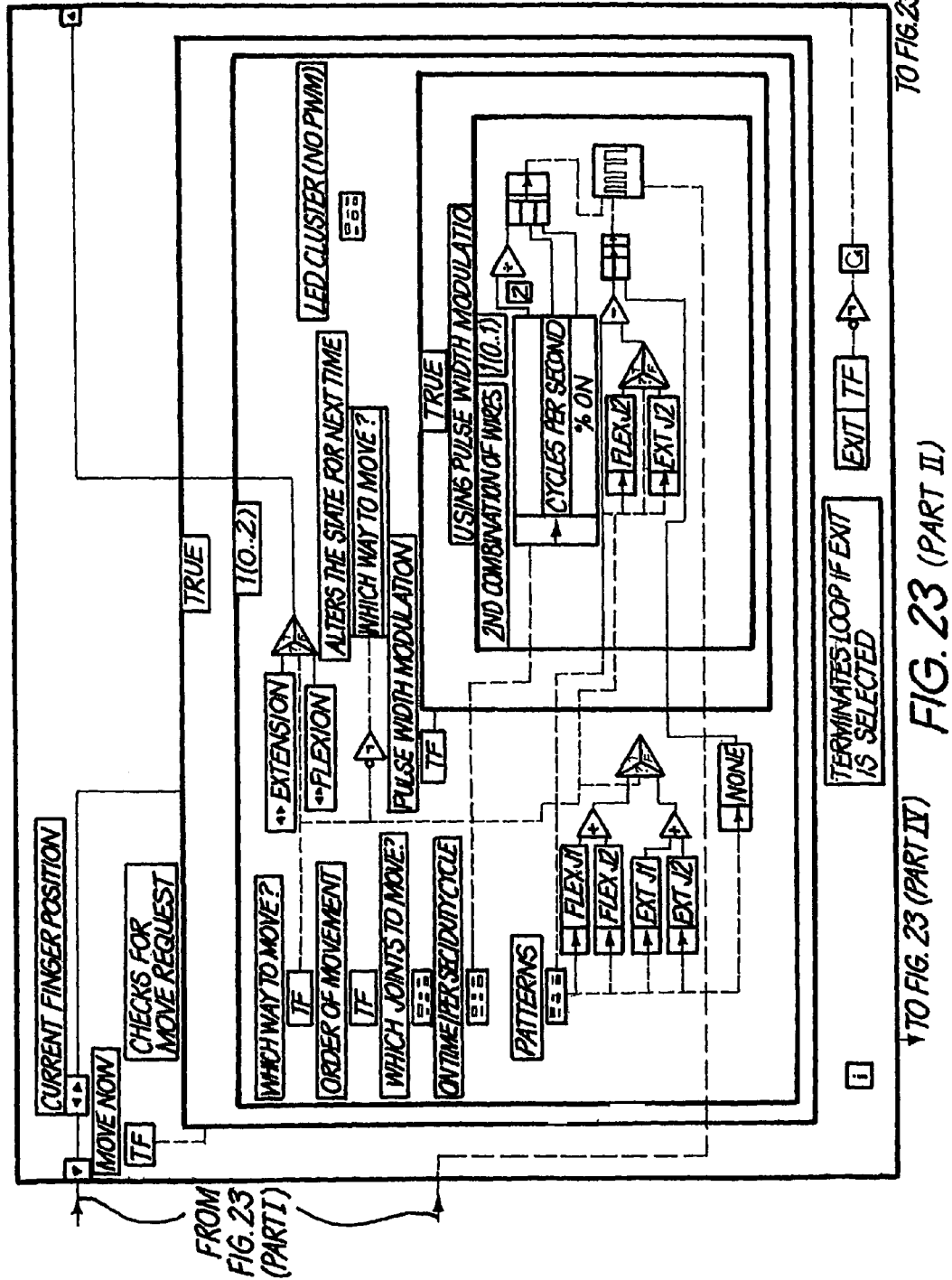
FIG. 23 (PART II)

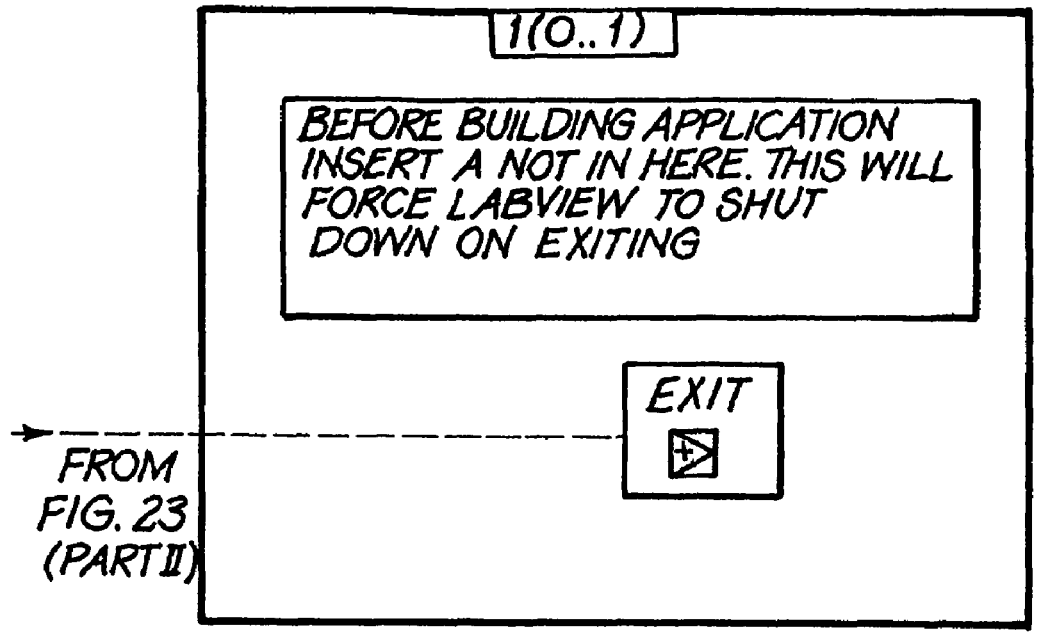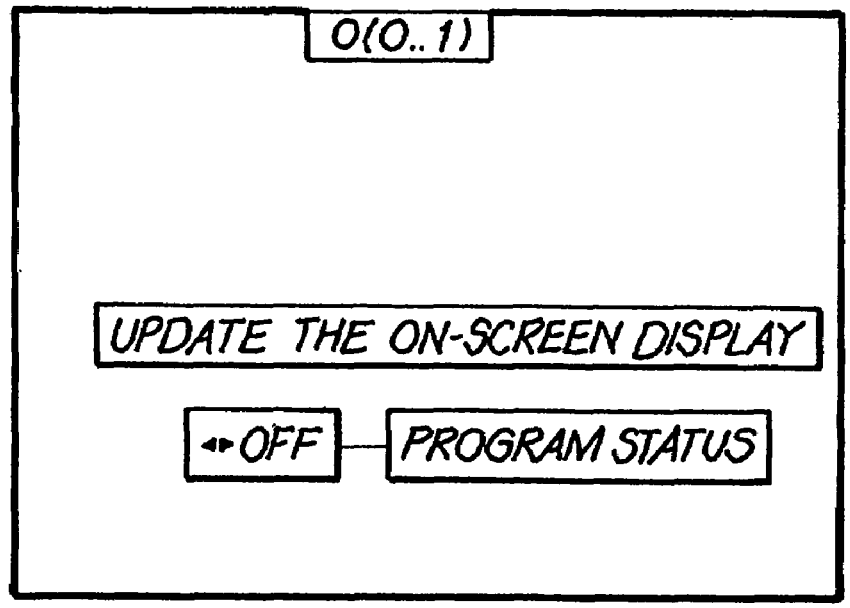
FIG. 23
(PART III)

(PART IV)

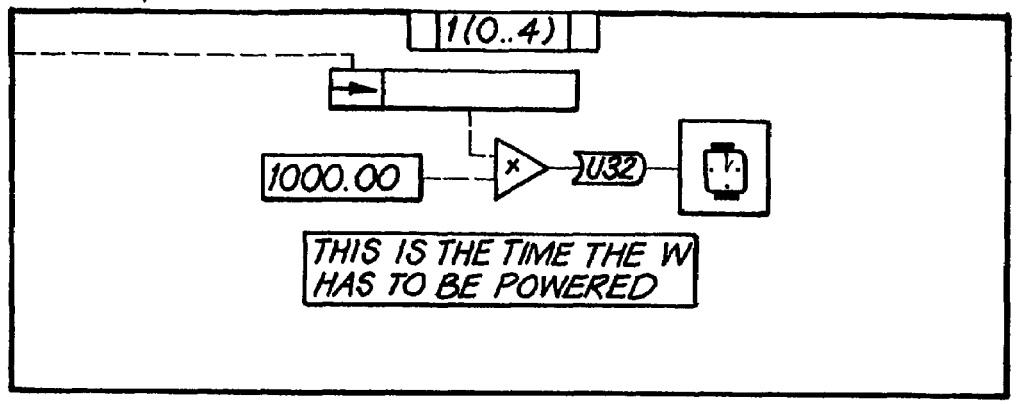
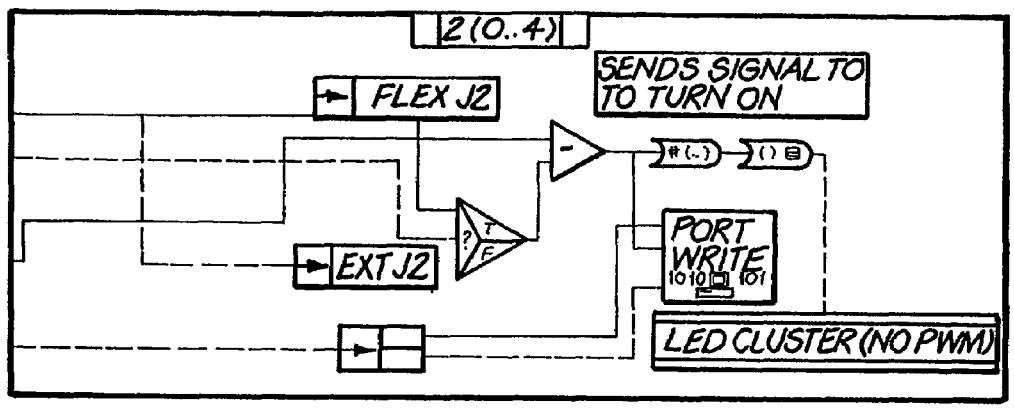
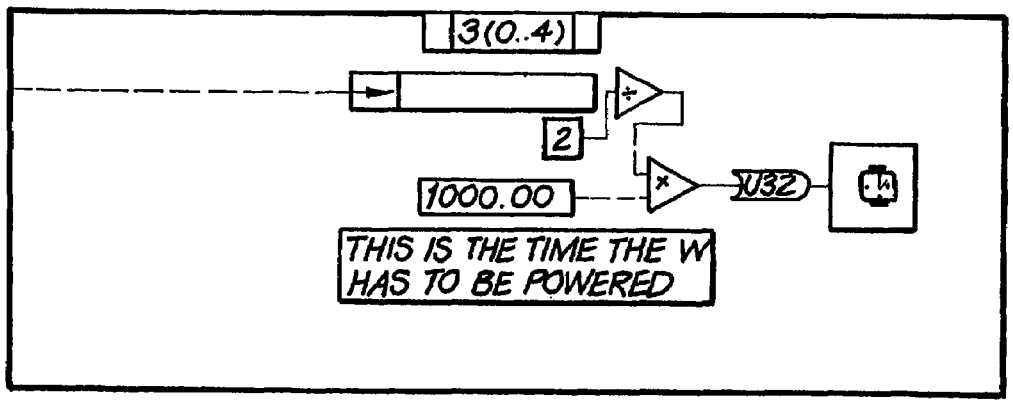
FIG. 23
(PART V)

↑ TO FIG. 24 (PART II)

(PART I)

↓FROM FIG. 24 (PART I)

|2(0..2)|

UPDATES THE ON-SCREEN DIS
•• STANDBY — PROGRAM STATUS

|FALSE|

NO MOVE REQUESTED SO WAIT 500MS
(HALF A SECOND) AND THEN CHECK AGAIN

|500| —

(PART II)

MOVEMENT FACILITATION DEVICE

TECHNICAL FIELD

The present invention relates generally to devices for facilitating movement of objects. More specifically, the present invention relates to devices for facilitating the relative movement between two portions of an object. More specifically still, the invention relates to devices for facilitating the bending or deforming of an object or a joint. In that regard, the present invention also relates to devices for moving joints in a human or non-human animal body, or mimics thereof.

BACKGROUND OF THE INVENTION

The loss of hand function will affect every aspect of an individuals life. This includes the ability to feed and care for themselves and the ability to work and participate in family life. For people recovering from problems such as trauma, burns or surgery affecting the hand, careful management of hand rehabilitation can influence the outcome for the patient significantly. In order to reduce the possibility of mobility difficulties occurring, including loss of joint range of motion, muscle and tendon sheath adhesions or non-functional scar tissue formation, continuous passive motion (CPM) is often indicated.

Additionally, for people with reduced mobility of the hand due to upper limb paralysis, such as those with cervical spinal cord injury, stroke, cerebral palsy or peripheral nerve injury, disregard for management of the maintenance of the joint range of motion of the effected hand will result in contracture and limited joint range of motion. Such syndromes will reduce hand function, which is already limited by paralysis, and will negatively affect potential outcomes for aggressive rehabilitation techniques, such as tendon transfer surgery and functional neuromuscular stimulation. Therefore, in such cases, CPM is also indicated.

Current devices applying CPM have shown to be effective in minimising the syndromes indicated above. Unfortunately, the use of such devices is not always prescribed by clinicians. This is due, mainly, to the limitations of these devices that are in the marketplace. These limitations include lack of secure finger placement, lack of portability, the inability to provide specialised therapy to specific joints, inflexible programming, of the device (only on or off with only one treatment modality) and, more importantly, the potential for damage to the hand to occur due to ineffective securing and placement of the fingers and thumb in the device.

It is important to note that the therapeutic benefits of continuous passive movement rely on the response of dense ordinary connective tissue to low-load prolonged stress (LLPS). In the human body, joints, tendons, ligaments, synovial membranes, fascia and the fibrous joint capsule are all composed of connective tissue. The deprivation of these elements of stress after an injury has been found to be detrimental. Indeed, profound structural and functional changes can occur which result in restricted mobility.

Although immobilisation had been previously championed with respect to the healing of orthopaedic injury (as early as the late nineteenth century by HO Thomas), such structural changes contraindicated it in many cases. These structural changes include:

Development of fibro-fatty deposits within the joint;
Diminished ground substance (which usually serves as a joint spacer and lubricant plus allows collagen fibres to glide freely);
Excessive randomly oriented collagen fibre crosslinks resulting in intrarticular and extraarticular adhesions;
A reduction in the extensibility of the joints with resultant joint stiffness.

It has been shown that stress deprivation can cause what is termed iatrogenic immobilisation disease which is characterised by muscle disuse atrophy, disuse osteopenia and the destruction of articular cartilage with late secondary degenerative arthritis. In combatting the occurrence of such problems, CPM:

Maintains the proper constituents within the ground substance;
Inhibits abnormal cross-linking of collagen fibres;
Enhances cellularity, strength and mobility of the tissues.

Thereby, CPM prevents intraarticular and periarticular adhesions. In achieving such a therapeutic benefit, CPM has shown to clinically:

Minimise joint stiffness;
Improve the healing and regeneration of articular cartilage;
Reduce inflammatory conditions;
Improve wound healing;
Improve the repair of Ligaments and tendons;
Reduce pain;
Support more rapid and stronger healing of repaired ligament;
Improve healing subsequent to bone fractures.

In usual clinical hand therapy, therapists apply passive movement to the hand for mobilisation of its structures. CPM has been applied for the purpose of providing such therapy although with increasingly lasting results. Nevertheless, the limitations of prior art machines applying such CPM have reduced their impact on the patient population.

Prior art to embodiments of the invention is the portable continuous passive motion machine as applied to the human upper extremity. This has involved the attachment of a motor to the forearm. The motor usually drives a cross bar or longitudinal bars, which are attached to the fingers, in a cyclical pattern. These produce a continuous pattern of finger flexion followed by finger extension driven by the motor. This is for the purpose of maintaining and improving the condition of the hand during rehabilitation. This includes improving finger joint range of motion, reduction of oedema and reducing the likelihood of tendon sheath adhesions.

Prior art weighs the hand down with a motor which, in addition to being heavy and awkward for the user (thus limiting their mobility), is non-cosmetic. Additionally, the 15 power requirements of the motor limit the portability, especially if the device is driven from mains power. Where the device is battery driven, the length of therapy is limited. The cross bar configuration of the prior art allows the possibility of misalignment of the fingers in the device, thereby producing the risk of damage to the hand. Such therapy is applied to all the fingers at the same time, in the same manner. Therefore, tailoring of therapy to individual fingers and joints is not possible.

Priority needs are repeatability, reliability and portability. Preferred devices should also be cosmetically pleasing, light weight, energy efficient for portable battery power, flexible in operation and comfortable, robust, easy to don and doff securely, and safe when used.

SUMMARY OF THE INVENTION

In a first aspect, the present invention provides a movement facilitation device for facilitating movement between a first portion of a first object and a second portion of the first object, said device having:

(a) at least one actuator,
a first part of the actuator coupled to the first portion of the first object, said actuator for moving said first portion with respect to the second portion; and
(b) an operating means coupled to the actuator for operating the actuator.

The device may have:
(a) an actuator for moving the first portion with respect to the second portion, said actuator being coupled to the first portion of the first object; and
(b) an operating means coupled to the actuator for operating the actuator. In some preferred embodiments, the first object has a bendable or moveable portion coupling the first and the second portions. In some preferred embodiments a second part of the actuator is coupled to the second portion of the first object. In other preferred embodiments, a second part of the actuator is coupled to a second object.

In some preferred embodiments, the first object is any object capable of being bent, moved, or deformed in such a way that first and second portions of the object can be moved relative to one another.

In further preferred embodiments, the first object is a joint including at least two members which the joint's purpose it is to move relative to one another by movement of the joint.

Joints of preferred embodiments are any joints capable of movement in a single plane or in multiple planes. They can include all forms of mechanical and non-mechanical joints. They can also include joints in the human body, including the relevant bones which the joints' purpose it is to move relative to one another by movement of the joints.

In many of the more preferred embodiments, the movement facilitation device can be applied to a range of joints including all finger, thumb and hand joints, all toe and foot joints, wrist joints, elbow joints, shoulder joints, ankle joints, knee joints, hip joints, and any of the joints associated with the spinal column and skull, including the jaw.

Furthermore, apart from some preferred embodiments in which the first object is a human body joint, the first object may also be a prosthesis of a human body joint. The first object can also be the joint of a non-human animal, or a prosthesis thereof. The non-human animal may be a mammal or a bird or some other animal. It may be for example a horse or a monkey or an ape or a cow or a pig or a sheep. The first object can further be a joint in a mimic of a human or non-human animal, such as a toy, mannequin or robot. In yet still further preferred embodiments, the first object may also be a support structure, exoskeleton, cage, caliper, orthosis, splint, or portion thereof, which is designed to be put on or replicate a human or non-human animal or a mimic of a human or non-human animal. Thus the first object may be a prosthesis of a joint selected from the group consisting of a human body joint and a joint of a non-human animal.

In some embodiments, the movement facilitation device is implantable and capable of performing its function within the human or non-human animal's body.

The second object of some preferred embodiments is a separate and independent object from the first object. In other preferred embodiments, the second object is coupled with, connected to, or integral with the first object. In such embodiments, the second object may be effectively indistinguishable from the first object being a component thereof.

Preferred embodiments of the first and second objects are described in more detail below with reference to specific preferred embodiments of the movement facilitation device and/or specific preferred embodiments of a plurality of movement facilitation devices functionally coupled so as to work together toward specific aims.

Some preferred embodiments of the actuator are formed of a non-flexible or flexible member. Other preferred embodiments of the actuator are formed of a material which, when operated, contracts or decreases in length. In such embodiments, the material from which the actuator is formed features elastic and/or contractile and/or resilient properties. One embodiment of the actuator is a rubber band. Another embodiment is a strip of elastic.

In more preferred embodiments, the actuator is formed of a material which has a shape memory, such as Nitinol (Ni—Ti), Cu—Al—Ni, Cu—Zn—Al, and others. In such embodiments, the length of the actuator can decrease when the temperature of the actuator is caused to change, for example, when the actuator is heated to an appropriate temperature. The relevant change in temperature may be caused by passing a current through the shape memory material.

In other embodiments, the length may also decrease when, for example, an electrical potential across the actuator is altered, or when a current is passed through the actuator, or when a magnetic field is brought into appropriate proximity to the actuator. In other words, any material which is capable of changing its shape upon application of a relevantly appropriate form of energy to cause that change in shape is suitable material from which an actuator of these preferred embodiments can be formed.

In preferred embodiments, the actuator is an electromechanical actuator of a type utilising a conducting polymer for effecting a desired action with change(s) in the volume of the polymer in response to an applied potential.

In one embodiment, the electromechanical actuator comprises:
a conducting polymer and a conductor for conducting voltage along the polymer from one end region of the polymer to an opposite end region of the polymer, wherein the conductor is capable of extending and contracting in length with expansion and contraction of the polymer.

Typically, the conductor will be arranged for enabling expansion and contraction with the polymer. Hence another embodiment of the electromechanical actuator of the present invention comprises:
a conducting polymer and a conductor for conducting voltage along the polymer from one end region of the polymer to an opposite end region of the polymer, wherein the conductor is arranged for extending and contracting in length with expansion and contraction of the polymer.

Preferably, the conductor will be wound in a helix along the polymer.

Accordingly, another embodiment of the preferred electromechanical actuator comprises:
a conducting polymer and a conductor wound in a helix along the polymer for conducting voltage from one end region of the polymer to an opposite end region of the polymer.

Typically, the conductor will be in intimate contact with the conducting polymer substantially along the entire length of the polymer. Preferably, the conductor will be embedded in the polymer.

Preferably, the conducting polymer will be in the form of a tube. The tube may have a cross-section lying in a plane extending substantially perpendicularly to a longitudinal axis of the tube of any desired shape. Generally, the shape of the cross-section of the tube will be substantially circular.

Another embodiment of the preferred electromechanical actuator comprises:
a tube of conducting polymer having an internal passageway for receiving an electrolyte.

Preferably, the electromechanical actuator will further comprise an electrical connector for facilitating electrical connection to the conductor. Typically, the connector will also be in direct electrical contact with the polymer. Most preferably, an electrical connector will be connected to each end of the conductor, respectively.

If desired, the further electrical connector may also be in direct electrical contact with the polymer at a spaced distance from the first mentioned electrical connector.

A further embodiment of an electromechanical actuator of the present invention is made according to a method, which method comprises:

forming a tube of conducting polymer around a template having a desired shape.

Yet another embodiment of a preferred electromechanical actuator is made according to a method, which method comprises:

forming a polymer body on a conductor for extending and contracting in length with expansion and contraction of the polymer body and conducting voltage along the polymer body from one end region of the polymer body to an opposite end region of the polymer body.

Typically, the conducting polymer will be electrodeposited onto the template and/or the conductor.

Yet another preferred embodiment of an electromechanical actuator is made according to a method, which method comprises:

electrodepositing a conducting polymer onto a conductor wound in a helix to form a polymer body in which the helix is embedded.

A further embodiment of the electromechanical actuator is made according to a method, which method comprises:

(a) winding a conductor onto a template to form a helix along the template; and (b) electrodepositing a conducting polymer onto the helix to form a polymer body in which the helix is embedded;

wherein the helix is in electrical contact with the polymer body for conducting a voltage along the polymer body from one end region of the polymer body to an opposite end region of the polymer body.

Typically, the conducting polymer will be electrodeposited onto the helix while the helix is wound around the template.

Preferably, the method will further comprise the steps of:

(c) removing the template from the helix;

(d) connecting an electrical connector to one or each end section of the conductor for facilitating electrical connection with the conductor; and (e) securing the conductor to the or each electrical connector.

Preferably, an electrical connector will be inserted into the one end region of the polymer body and another said electrical connector into the opposite end region of the polymer body.

The conducting polymer may be any polymer capable of undergoing a volume change in response to redox processes and which is deemed suitable for use in the provision of an electromechanical actuator of the type to which the present invention relates. Suitable polymers include, but are not limited to polyaniline, polypyrrole, polythiophene, derivatives thereof and mixtures thereof. That is, the polymer used may comprise a polymeric material consisting of a number of different polymers. Accordingly, the term "conducting polymer" is to be taken to include a mixture of polymers capable of undergoing redox processes. Derivatives include, for example, alkyl, alkoxy, amine and alcohol derivatives of polyaniline, polypyrole and polythiophene such as, for example, poly(3-alkyltbiophene)s. Thus in an embodiment of the invention, the electromechanical actuator comprises a conducting polymer selected from the group consisting of polyaniline, polypyrrole, polythiophene, derivatives thereof and mixtures thereof.

The conductor used for conducting voltage along the polymer will typically have greater conductivity ($\kappa$) compared to the conducting polymer utilised. The conductor may be formed from any material deemed suitable. For example, the conductor may be another conducting polymer such as a polyaniline fibre or thread. Preferably, however, the conductor will be a metal such as platinum, gold, silver or other metal with sufficient flexibility to expand and contract in concert with expansion and contraction of the conducting polymer. Most preferably, the conductor will be a wire.

Preferably, the template will also be conductive and most preferably, a length of metal such as a metal strip, wire or the like. Generally, the template will consist of the same material as used for the conductor.

The electrical connector(s) may be any short length of conducting metal. Preferably, the or each electrical connector will consist of the same material as used for the conductor.

The conductor will generally be secured to the or each electrical connector by wrapping the connector tightly around the connector(s) or by spot welding or other suitable means. Preferably, the conductor will also be secured to the connector(s) by a suitable epoxy resin.

By forming the conducting polymer in the shape of a tube, it has been found that improved characteristics of the actuator may be obtained compared to the conducting polymer when provided in strip form. In particular, one or more of the electronic, mechanical and/or electrochemical properties of the actuator may be enhanced. While not being bound by theory, it is believed that a tube configuration has enhanced electrolytic efficiency compared to an actuator in the form of a strip as more of the conducting polymer comprising the tube is electrochemically accessible than a corresponding strip of the polymer.

It is further believed the provision of the conductor further enhances electrolytic efficiency by reducing voltage (iR) drops along the conducting polymer, enabling longer fibres to be used while retaining efficient activation capability.

The electromechanical actuator of preferred embodiments may be provided in a suitable electrolyte. The electrolyte may be a liquid or solid electrolyte, and the actuator may be immersed in the electrolyte or otherwise coated with the electrolyte. An electrolyte may for instance be contained in a film of cellophane or a gel such as a polyacrylamide gel. Preferred electrolytes include ionic liquids (salts that are liquid at room temperature) and particularly, ionic liquids containing polymers.

Some preferred embodiments of actuators are formed of for example, any combination of a conducting polymer such as that described above, carbon nanotubes and Nitinol or other shape memory alloy.

It is important to note that while the above description appears to limit embodiments of the invention to include only one actuator, other preferred embodiments of the invention provide that there are plurality of such actuators all coupled together for each movement facilitation device. In some such embodiments, although the plurality of actuators are coupled together, they are insulated from one another. In other of such embodiments, there is no insulation between the actuators and any change in potential effected across one such actuator is also effected across the others. Having a plurality of actuators for each movement facilitation device may well increase the strength and capabilities of those movement facilitation devices.

Alternative embodiments of the actuator are formed of a reel and pulling means. The pulling means may be a string, rope, tape or any other means capable of being reeled and having a resilience that can withstand a pulling pressure. In such embodiments, the actuator decreases in length as the pulling means is reeled in on the reel. The reel of such embodiments may be operated manually or automatically.

Further alternative embodiments of the actuator comprise any means that is capable of performing the function of the actuator, in particular, causing a first portion of an object to be moved relative to a second portion of the object when operated. The actuator may be capable of actuation in a continuous manner.

As already indicated, in preferred embodiments of the movement facilitation device a first part of the actuator is coupled to a first portion of the first object and a second part of the actuator is coupled to the second object. The construction of more preferable coupling arrangements depends on the purpose for which the device is being used as well as the type of actuator and the nature of the objects to which the actuator is being coupled.

In some preferred embodiments, the coupling arrangement between the first part of the actuator and the first portion of the first object is different to the coupling arrangement between the second part of the actuator and the second object. Such a situation may arise, for example, where the second object is a separate and independent object from the first object. In other preferred embodiments, the coupling arrangement between the first part of the actuator and the first portion of the first object is the same as the coupling arrangement between the second part of the actuator and the second object. Such a situation may arise, for example, where the second object is coupled with, connected to, or integral with the first object, and is effectively indistinguishable from the first object being a component thereof.

It is important to note that the examples described in the previous paragraph are illustrative only. Accordingly, where the second object is a separate and independent object from the first object, it may be that the respective and relevant coupling arrangements will be the same as one another. Similarly, where the second object is effectively indistinguishable from the first object, it may be that the respective and relevant coupling arrangements will be different to one another.

In some preferred coupling arrangements, the relevant part of the actuator is secured to the relevant object by securing means. Any form of securing means capable of ensuring that the actuator is not uncoupled from the objects when the actuator is operated is suitable. Examples of securing means that may be suitable include, but are not limited to, adhesives of various forms, welds, solders, nails, screws, pins, rivets, crimping, and the like.

In other preferred coupling arrangements, the relevant part of the actuator is connected to the relevant object by connection means. Appropriate connection means for such embodiments take the form of a pivot mechanism whereby the relevant part of the actuator is pivotally connected to the relevant object. In such embodiments, movement of the first portion of the first object relative to the second portion of the first object can be further facilitated by the pivotal mechanism between the relevant part of the actuator and the relevant object.

In yet still further preferred coupling arrangements, the relevant part of the actuator is integral with the relevant object. In such embodiments, the relevant part of the actuator may be melted or melded into or onto the relevant object. The relevant part of the actuator and the relevant object may also be chemically treated such that they are caused to become integral with one another.

Further preferred embodiments of the coupling arrangements additionally take into consideration the specific properties of the actuator that enable the actuator to perform its function. For example, where the actuator changes shape when an electrical potential across the actuator is altered, the coupling arrangement may include electrical insulation. The coupling arrangement of such embodiments may additionally or alternatively be formed, at least in part, of an electroconductive material.

The particular way the coupling arrangement takes into consideration the specific properties of the actuator that enable the actuator to perform its function depends on the circumstances for which the movement facilitation device is being used, and is preferably determined on that basis. Similarly, whether or not the coupling arrangements do, in fact, additionally take into consideration the specific properties of the actuator that enable the actuator to perform its function also depends on the circumstances for which the movement facilitation device is being used, and is also preferably determined on that basis.

In some preferred embodiments, by attaching the actuator at a small radius from an axis of movement, a small change in the actuator's length can cause a significant movement in the first object. Accordingly, in some preferred embodiments where the device is being used, for example, on a finger joint, a 5% reduction in length of the actuator may achieve full flexion of the finger joint, when the actuator is coupled as described above.

Some specific examples of appropriate constructions for the coupling arrangements are described in more detail below with reference to specific preferred embodiments of the movement facilitation device and/or specific preferred embodiments of a plurality of movement facilitation devices functionally coupled so as to work together toward specific aims.

The operating means of preferred embodiments operates the actuator. Accordingly, preferred operating means are capable of operating at least one of the preferred embodiments of the actuator described above. Some preferred embodiments of the operating means are capable of operating more than one, or all, preferred and alternative embodiments of an actuator capable of being used in the performance of the present invention.

An aspect of the invention comprises a movement facilitation device according to the invention wherein the operating means comprises:

a power source having an on/off switch; and at least one actuator interface linking the power source to the actuator, wherein when the power source is switched off, no power passes through the actuator interface and there is no change in electrical potential across the actuator, and wherein when the power source is switched on, power passes through the actuator interface, and an electrical potential across the actuator is altered, thereby causing the actuator to operate.

In another aspect, said movement facilitation device additionally comprises a computer.

Some preferred embodiments of an operating means for operating an actuator formed of a memory material responsive to a change in electrical potential, include:

a power source having an on/off switch; and at least one actuator interface linking the power source to the actuator, wherein when the power source is switched off, no power passes through the actuator interface and there is no change in electrical potential across the actuator, and wherein when the power source is switched on, power passes through the actuator interface, and an electrical potential across the actuator is altered, thereby causing the actuator to operate.

Other preferred embodiments of an operating means for operating an actuator formed of a memory material responsive to a change in electrical potential, include:

a power source;
a digital to analog converter having a computer interface; and
at least one actuator interface, wherein when the digital to analog converter receives a signal from a computer, the signal is conveyed through the actuator interface, thereby altering the electrical potential across the actuator causing the actuator to operate.

In such embodiments of an operating means for operating an actuator formed of a memory material responsive to a change in electrical potential, the actuator interface is preferably an electricity carrying means connectable to the actuator.

Further preferred embodiments of an operating means for operating an actuator formed of a memory material responsive to a change in temperature, include:

a power source having an on/off switch;
at least one actuator interface; and
a temperature changing means operably connected to the power source and to the actuator via the actuator interface, wherein when the power source is switched off, no power passes to the temperature changing means and the temperature of the actuator is unchanged, and wherein when the power source is switched on, power passes to the temperature changing means which causes the actuator to change temperature, thereby causing the actuator to operate.

Still further preferred embodiments of an operating means for operating an actuator formed of a memory material responsive to a change in temperature, include:

a power source;
a digital to analog converter having a computer interface;
at least one relay operably connected to the digital to analog converter;
at least one actuator interface; and
a temperature changing means operably connected to the relay and to the actuator via the actuator interface, wherein when the digital to analog converter receives a signal from a computer, the signal is conveyed to the relay which activates and passes power to the temperature changing means which causes the actuator to change temperature, thereby causing the actuator to operate.

In such preferred embodiments of an operating means for operating an actuator formed of a memory material responsive to a change in temperature, the temperature changing means is a heater in which case the actuator is heated when the heater receives power from the power source.

In further preferred embodiments, the temperature changing means is an electricity carrying means capable of carrying sufficient electricity to cause the actuator to increase its temperature when the electricity passes from the temperature changing means to the actuator. Such embodiments would be particularly valuable where the actuator is formed of Nitinol.

In other such preferred embodiments of an operating means for operating an actuator formed of a memory material responsive to a change in temperature, the temperature changing means is a cooler in which case the actuator is cooled when the cooler receives power from the power source.

In many embodiments of the operating means for operating an actuator formed of a memory material responsive to a change in temperature, the actuator interface is preferably formed of a material that is amenable to changing its temperature, and even more preferably such a material that is well suited either to heating or cooling depending upon the specific properties of the actuator with which it is interfaced.

Yet still further preferred embodiments of an operating means for operating an actuator formed of a reel and pulling means which is operated manually, is a rotation means which, when moved, causes the reel to operate.

In such embodiments, the operation means may take the form of a knob located anywhere on the reel, being a location that enables the reel to be operated when the knob is moved. The rotation means is not, however, limited to being a knob, and may take any form that enables adequate performance of its function.

Preferred embodiments of an operating means for operating an actuator formed of a reel and pulling means which is operated automatically, includes:

a power source having an on/off switch;
at least one actuator interface coupled to the reel; and
an automatic rotation means operably connected to the power source and to the actuator interface, wherein when the power source is switched off, no power passes to the automatic rotation means and there is no movement of the reel, and wherein when the power source is switched on, power passes to the automatic rotation means causing said means to rotate thereby rotating the reel via the actuator interface and causing the actuator to operate.

In another preferred embodiment of an operating means for operating an actuator formed of a reel and pulling means which is operated automatically, includes:

a power source;
a digital to analog converter having a computer interface;
at least one relay operably connected to the digital to analog converter;
at least one actuator interface; and
an automatic rotation means operably connected to the relay and to the actuator via the actuator interface, wherein when the digital to analog converter receives a signal from a computer, the signal is conveyed to the relay which activates and passes power to the automatic rotation means causing said means to rotate thereby rotating the reel via the actuator interface and causing the actuator to operate.

In such embodiments of an operating means for operating an actuator formed of a reel and pulling means which is operated automatically, the automatic rotation means may be a motor or any other means capable of causing the reel to automatically rotate. Operation of the actuator, in such embodiments, results in a shortening of the pulling means.

In some embodiments where the actuator is a non-flexible or flexible member, the operating means causes movement of the actuator to change the distance between the first portion of the first object and the operating means.

In many of the embodiments of the operating means which utilise a relay, the relay is preferably a solid state relay. The relay can also be a mechanical relay. In many embodiments of the operating means described above that do not mention a relay, it is important to note that depending on the particular material chosen for the actuator, a relay can additionally be used as a further component of the operating means' circuit.

For example, it is relevant to note that Nitinol responds to a change in temperature. As alluded to above, this change in temperature can be achieved by passing a current through it. For such embodiments, it may be necessary to include a relay in the operating means' circuit, as higher currents are required. On the other hand, actuators formed of polymers or carbon nanotubes as described above respond to a change in current only and do not require a change in temperature. In such embodiments, as only a small amount of current is required, relays may not be a necessary component of the circuit.

Actuators made of the polymers and/or nanotubes have been shown to be capable of generating forces in the order of 1 Newton per cm sample width by the application of potentials no higher than 1 or 2 volts. The current drawn in the operation of such devices is very small and, preferably, in the vicinity of 10 mA per Newton.

Many preferred embodiments of the operating means use a computer. Any computer having appropriate software and/or hardware may be utilised in the performance of this invention. In one preferred embodiment, the computer takes the form of a desktop computer. In another preferred embodiment, the computer takes the form of a laptop computer or notebook. In still another preferred embodiment, the computer takes the form of a palmtop computer, such as, for example, a PalmPilot. In yet still further preferred embodiments, the computer is custom made for the purpose of carrying out this invention and is a custom pager sized device.

Provided that appropriate software may be installed on the computer, the computer may have any operating system thereon, including DOS, Windows, Macintosh, Unix, Linux.

An example of a basic circuit layout for one preferred embodiment of the operating means which can be connected to a computer is illustrated in FIG. 11.

The software of preferred embodiments is tailored to provide the movement facilitation device with the necessary instructions to perform its function. Such instructions vary depending on the purpose for which the device is being used. Some detailed examples of purposes for which the movement facilitation device could be used are given below with reference to specific preferred embodiments of a movement facilitation device and/or specific preferred embodiments of a plurality of movement facilitation devices functionally coupled so as to work together toward specific aims.

In an embodiment, parameters of a software program on said computer allow for customising and selection of protocols to enable desired movements.

By way of preliminary example, where a movement facilitation device or a plurality of such devices are being used to cause movement of a joint or a plurality of joints in a human body the parameters of the preferred software program will allow for customising and selection of protocols to enable desired movements. Preferred parameters for such embodiments of the invention may include: joint selection, joint range of motion, speed of motion, force of motion, duration of motion, direction of motion, and frequency of motion.

Where the program LabVIEW Professional Development System (manufactured by National Instruments) is running on the relevant computer, preferred embodiments of the software my be run through LabVIEW. Having said that, it is not necessary for preferred embodiments of the software to be run through LabVIEW or through any other such software development platform program.

An example of some preferred embodiments of software for instructing a movement facilitation device having an operating means for operating an actuator formed of a memory material responsive to a change in electrical potential and being used for the purpose of moving at least one human joint is found in FIGS. 12-24. The software program illustrated in those figures was created using LabVIEW.

In a second aspect, the present invention provides a movement device for facilitating movement of at least one joint of a patient's body, said device having:

(a) a support structure for enveloping at least a portion of the patient's body proximate the joint, said support structure formed of at least a first strut member positioned so as not to interfere with an ability of the joint to move;

(b) at least one movement means corresponding to the at least one joint, said movement means coupled to the first strut member; and (c) at least one movement facilitation device having at least one actuator, a first part of the actuator coupled to a first portion of the first strut member, said actuator for moving said first strut member thereby causing movement of the joint, and an operating means coupled to the actuator for operating the actuator. The invention also provides a movement device according to the invention when used to move a joint or a limb, or when used to rehabilitate a joint or a limb.

The movement device of the invention may be used to move the joint or limb one time or more than one time. It may be used to cycle the joint through a sequence of movements. The number of cycles may be between 1 and 10000 or between 1 and 5000 or between 1 and 1000 or between 1 and 500, or between 1 and 100 or between 1 and 50 or between 1 and 40 or between 1 and 30 or between 1 and 20 or between 1 and 10, and may be about 1, 2, 3, 4, 5, 10, 15, 20, 30, 40, 50, 75, 100, 150, 200, 250, 300, 350, 400, 450, 500, 600, 700, 800, 900, 1000, 1500, 2000, 2500, 3000, 4000, 5000, 6000, 8000 or 10000. The time for each cycle may be between 1 second and 10 minutes or between 1 second and 5 minutes or between 1 second and 1 minute or between 1 and 50 seconds or between 1 and 40 seconds or between 1 and 30 seconds or between 1 and 20 seconds or between 1 and 10 seconds, and may be about 1, 2, 5, 10, 15, 20, 25, 30, 40, or 50 seconds or about 1, 2, 3, 4, 5, 6, 7, 8, 9 or 10 minutes.

In some preferred embodiments, the support structure additionally has at least a second strut member and the movement means couples the first strut member to the second strut member. In such embodiments, operation of the actuator causes the first strut member to move relative to the second strut member, thereby causing movement of the joint. In further preferred embodiments, a second part of the actuator is coupled to a second object.

In an embodiment, said device has (a) a support structure attached to at least a portion of the patient's body proximate the at least one joint, said support structure comprising at least a first member positioned so as not to interfere with an ability of the at least one joint to move; and (b) at least one movement facilitation device having at least one actuator and at least one operating means, said actuator being coupled to the first member, and said operating means being coupled to the actuator for operating the actuator.

The support structure may comprise at least one artificial joint or other movement means corresponding to each of the patient's joints which are intended to be moved by the device.

Indeed, in some preferred embodiments, the movement facilitation device is adapted for use with hand and/or finger joint/s and/or thumb joint/s of a patient.

It is relevant to note that the device of such preferred embodiments may significantly benefit people after hand trauma and/or hand surgery (especially helping in the reduction of the formation of scar tissue which has a detrimental effect on hand function). Additionally, or alternatively, the device may be applied to maintain and increase good condition of a person's hand and hand function following spinal cord injury, burns, stroke, the onset of arthritis, septic arthritis, oedema, peripheral nerve injury and/or other syndromes influencing the condition and/or function of the upper extremity, including, for example, cerebral palsy.

The device of such embodiments may additionally or alternatively be used to provide hand function to patients with impaired hand function. Where such patients are capable of achieving some small function without assistance, the device of preferred embodiments may aid those patients to improve that function further. Where such patients are unable to achieve any function without assistance, the device may perform the function on behalf of the patient.

This may allow an increase in independence for the permanently disabled and an early restoration of function for those recovering (such as patients with peripheral nerve injury). In addition to allowing injured individuals a greater societal contribution in this way, such an improvement in function will provide a significant cost benefit via the reduction of the need for paid personal carers and a possible early return to work.

When appropriately adapted and when coupled with an appropriate number of other of such devices, the movement device can be used to aid or achieve a full range of hand movements including, for example, pinching, clenching a fist, holding a pen, paintbrush or other such means, holding cutlery, holding a toothbrush, and so on.

Such embodiments provide an example of a plurality of movement facilitation devices functionally coupled so as to work together toward specific aims. These are referred to as combination embodiments.

In preferred combination embodiments, a support structure envelops the patient's hand. The support structure may envelop a finger, a thumb, more than one finger, a wrist, an elbow, or a shoulder, or appropriate combinations thereof. In some embodiments, the support structure extends from the tip of the fingers and/or thumb to a point distal to the wrist. In other embodiments, as the case may be, the support structure may envelop the patient's wrist joint or elbow joint or the patient's entire arm including the shoulder joint.

The support structure of some preferred combination embodiments is formed of a plurality of strut members joined together in such a way that does not interfere with the ability of the joints (which the support structure envelops) to move. Of course, where there are certain joints which are not intended to be moved by the application of this invention there is no need for the support structure to be designed to enable the movement of those joints. In some preferred embodiments, however, the support structure additionally envelops joints that are not necessarily intended to be moved or are intended to be splinted in a particular position. In such embodiments the combination embodiment can be worked so that appropriate and opposing movement facilitation devices are operated so as to immobilise the joint.

The strut members of preferred combination embodiments may be formed of any material which provides sufficient stiffness and/or resilience to enable the movement facilitation device to perform its function. By way of example only, the strut members may be formed of aluminium, another metal, an alloy, a plastic, or in appropriate circumstances, combinations thereof.

A preferred support structure has an artificial joint or other movement means corresponding to at least each of the patient's joints which are intended to be moved by the invention. The artificial joint or movement means of preferred combination embodiments can take any form which allows movement of the patient's joint to which the artificial joint or movement means corresponds.

The form which the artificial joint or movement means takes may be designed by reference to the patient's joint to which it corresponds. For example, an artificial joint or movement means corresponding to the proximal interphalangeal joint may take the form of a single pivot joint capable of moving in one plane only. It may also take the form of a bendable member capable of being bent in one plane only. Similarly, an artificial joint or movement means corresponding to the shoulder joint may take the form of, for example, a ball and socket joint capable of movement in multiple planes. It may also take the form of a bendable member capable of being bent in multiple planes.

The artificial joints or movement means of preferred combination embodiments may be formed of any material which enables the artificial joint or movement means to perform its function, namely, to mimic the range of movements available to the patient's joint to which it corresponds. By way of example only, like the strut members, the artificial joints or movement means of preferred embodiments may be formed of aluminium, another metal, an alloy, a plastic, or in appropriate circumstances, combinations thereof. Indeed, this principle of construction for the artificial joints or movement means highlights the fact that the invention could be used for moving artificial limbs also.

The artificial joints or movement means may also be formed of a material which constantly seeks to retain its shape, such that once a deforming force capable of deforming the shape of the material is removed, the material immediately returns to its former shape. An example is a spring or a spring-clip arrangement. Other materials having this feature include, but are not limited to, rubber and fluid filled flexible tubes. Many of the more preferred combination embodiments have artificial joints or movement means formed of such a material since it will seek to return the patient's joint to its original position after a movement facilitation device (appropriately adapted to the support structure) is caused to cease operating. In this way, while the movement facilitation device may cause, for example, the proximal interphalangeal joint to flex, the artificial joint or movement means will cause the proximal interphalangeal joint to extend thereby returning its position to that prior to the flexion movement caused by the operation of the movement facilitation device. Of course, in some preferred combination embodiments, there may be at least two opposing movement facilitation devices acting on a single joint, such that one causes the joint to flex while the other causes the joint to extend.

Further preferred combination embodiments have at least one movement facilitation device operably coupled via its actuator to at least a first strut member leading from the artificial joint or movement means and, in some embodiments, coupled to a second strut member leading to the artificial joint or movement means. Referring back to the first aspect of the invention, in such embodiments, the artificial joint or movement means along with at least first and second strut members leading respectively from and to the artificial joint or movement means is the first object.

Further, in one embodiment, the first portion of the first object is the first strut member, the second portion of the first object is the second strut member, and the second object is a component of the second strut member. In another embodiment, the first portion of the first object is the first strut member and the second object is another part of the support structure, preferably proximal the artificial joint or movement means.

In some such preferred combination embodiments, each first object has two movement facilitation devices which can work in opposition to one another, wherein:

the first device, when operated, causes movement of the first object in a way which flexes the human joint to which the first object corresponds; and the second device, when operated, causes movement of the first object in a way which extends the human joint to which the first object corresponds.

Such combination embodiments are particularly useful for human joints that typically move in one plane only. With respect to the hand, such joints include, for example, the distal interphalangeal joints, the proximal interphalangeal joints and the metacarpophalangeal joints.

In further preferred combination embodiments there are a plurality of movement is facilitation devices operably coupled via their actuators to some of the first objects. Such embodiments are particularly useful for first objects which correspond to human joints typically capable of movement in multiple planes, such as, for example, shoulder joints.

In some preferred combination embodiments, there are a plurality of channels for guiding some of the actuators from their respective movement facilitation devices. By way of example only, there may be a channel for guiding all of the actuators from movement facilitation devices that flex each finger joint, namely, the metacarpophalangeal joints, the distal interphalangeal joints and the proximal interphalangeal joints. There may be one such channel for each finger. Similarly, there may be one such channel for guiding all of the actuators from movement facilitation devices that extend each of the finger joints. Again, there may be one such channel for each finger. There may also be other of such channels for guiding other groups of actuators that are, by virtue of their actions, appropriate to be channelled through the same channel.

In other preferred combination embodiments, the movement facilitation devices may be arranged such that their respective actuators run through each other in a concentric manner. In such embodiments, some of the actuators have a tubular structure with a hollow centre capable of receiving another actuator. In yet still further preferred combination embodiments, the arrangement of the movement facilitation device is such that a physical relationship between their respective actuators mimics that of the anatomical pathways of the human or non-human animal's tendons and, where appropriate, muscles of the hand.

In further combination embodiments, the actuators of each movement facilitation device remain completely independent of one another in the sense that their respective movement facilitation devices are not arranged in such a way that creates a special physical relationship between the actuators.

As suggested above, in some preferred embodiments, by attaching the actuator at a small radius from an axis of movement, a small change in the actuator's length can cause a significant movement in the first object. Accordingly, where the device is being used, for example, on a finger joint, a 5% reduction in length of the actuator may achieve full flexion of the finger joint, when the actuator is coupled as described above.

Having regard to these combination embodiments, operation of each of the respective movement facilitation devices, results in a particular movement of the artificial joint or movement means to which the device is operably coupled, and said movement of the artificial joint or movement means results in a corresponding and relative movement in a particular plane in the human joint to which the artificial joint or movement means corresponds. Ultimately, such embodiments can achieve a full range of movements for the particular human joint that they are seeking to move, since the number of movement facilitation devices corresponds to the number of planes in which that particular human joint can move. For example, preferred combination embodiments seeking to move a joint that moves in a single plane only, there may be two movement facilitation devices adapted for moving that joint. The first movement facilitation device would cause the joint to flex while the second would cause the joint to extend.

For preferred combination embodiments, the operating means is designed to accommodate the relevant number of movement facilitation devices. Accordingly, in some preferred embodiments of the operating means that have an on/off switch for the power source, there may be one on/off switch for each such movement facilitation device. In other preferred embodiments, there may be one such on/off switch for an appropriate plurality of movement facilitation devices, wherein such an appropriate plurality is, for example, a group of movement facilitation devices that perform similar functions, such as, flexion of each of the finger joints.

Similarly, in other preferred embodiments of the operating means that utilise a computer, there may be a corresponding electrical and/or computer data carrying channel for each movement facilitation device, said channel running through a circuit of the operating means via each component thereof and being capable of providing the necessary input for the operation of the movement facilitation device to which it corresponds. Thus the movement device according to the invention may have an operating means comprising a computer whereby there is a corresponding electrical and/or computer data carrying channel for each movement facilitation device, said channel being capable of providing the necessary input to the movement facilitation device to which it corresponds for the operation of said movement facilitation device.

In yet still further preferred combination embodiments, the operating means also has a controlling means for controlling a plurality of operating means. The control means of preferred embodiments has the capacity to receive information from a plurality of operating means or sensors and to use that information to control the operation of the operating means so as to achieve purposeful movement of the patient's joints.

The computer and software programs of such combination embodiments are designed to accommodate operating means capable of accommodating the plurality of movement facilitation devices.

In some preferred combination embodiments, there is at least one pressure sensor strategically located on or in the support structure in a proximity of at least one movement facilitation device, and/or on or in the movement facilitation device itself.

The pressure sensor of preferred embodiments is capable of providing feedback to the operating means as to the activity of the patient's joint which is sought to be moved by the movement facilitation device.

In some such embodiments, the pressure sensor senses any pressure difference created by the patient voluntarily moving the joint. Once that activity has been "sensed" by the pressure sensor, a feedback signal is transmitted to the operating means that causes the operating means to operate the actuator, thereby amplifying the patient's desired movement. Such embodiments are particularly valuable for patients who have, for example, a weakness and are capable of very small voluntary movements only.

In another embodiment, the pressure sensor senses any pressure difference created by operation of the movement facilitation device. Once such activity has been "sensed" by the pressure sensor, a feedback signal is transmitted to the operating means providing the operating means with information that it may use to regulate the activity of the movement facilitation device.

In another embodiment still, pressure sensors are located on or in the actuators. In some such embodiments, the pressure sources can provide feedback control of therapy to ensure safe and correct operation. In this way, such pressure sensors may provide a type of artificial proprioception.

In some preferred combination embodiments, there are three pressure sensors for each movement facilitation device where each such sensor has one of the functions described in the previous three paragraphs.

In still further preferred combination embodiments, where bandages or casts are applied, the support structure and/or the struts and/or the movement means may be incorporated into the casting or bandaging.

In yet still further preferred combination embodiments, a glove member which envelops the relevant joints of the hand and/or arm is used instead of the support structure. In other preferred combination embodiments, the glove member envelops the support structure.

The glove member of preferred embodiments can be formed of any material that is suitable to the functioning of the combination embodiment. The preferred glove member may be formed of a material that is aesthetically pleasing such that the glove can be worn as an item of clothing.

The glove may be suitable for application to any of a range of joints including all finger, thumb and hand joints, all toe and foot joints, wrist joints, elbow joints, shoulder joints, ankle joints, knee joints, hip joints, and any of the joints associated with the spinal column and skill, including the jaw. In this specification a glove is not restricted to enveloping a hand, but may envelop or partially envelop any of the above-mentioned joints or combinations thereof.

Thus a movement device for facilitating movement of at least one joint of a patient's body, according to the present invention, may have:

(a) a glove for enveloping at least a portion of the patient's body proximate the at least one joint;

(b) at least one movement facilitation device having at least one actuator, at least one operating means and at least one cable, said at least one cable forming a part of, or linked to, the glove, said actuator being capable of moving said cable thereby causing movement of the joint in use, and said operating means being coupled to the actuator for operating the actuator.

Indeed, in preferred combination embodiments of the invention, actuation is incorporated into a glove member improving its cosmetic appeal. Donning and doffing of the glove member may produce more reliable positioning of the hand in relation to the actuators than previously possible with the prior art. This will maximise the benefit and reduce the risk of damage occurring during operation. In some preferred combination embodiments, the movement facilitation devices are able to control the total of fifteen metacarpophalangeal, distal interphalangeal and proximal interphalangeal joints to provide specific therapies which were not previously possible with the prior art. Some individual joints within the glove member can be held stiff (splinted) to increase therapeutic options ahead of previous modalities. Therapy is electronically controlled and programmed. Such programs can be entered or downloaded to a small battery powered electronic control unit. Such programs of operation can modify, for example, the specific joints that are moved, the range of motion for each joint, the speed of movement, and the strength of movement.

This preferably provides increased flexibility and effectiveness to target specific regions with different therapies. One preferred combination embodiment is lightweight and portable and preferably provides the possibility of grasp control. With the provision of lightweight actuating materials incorporated into movement facilitation devices of preferred combination embodiments (including, for example, any combination of a conducting polymer, carbon nanotubes and Nitinol), the portability, efficiency, cosmetic appeal, effectiveness and flexibility for therapy and function will present significant advantages over the prior art.

It is envisaged that preferred combination embodiments will be applied to people post-hand trauma and post hand surgery. Also such embodiments, being movement devices according to the invention, can be applied to maintain and increase good condition of the users hand following spinal cord injury, burns, stroke, the onset of arthritis, peripheral nerve injury and/or other syndrome influencing the condition and function of the upper extremity.

Preferably, there is at least one mode of operation for preferred combination embodiments. Two such modes are, for example, Continuous Passive Motion Mode and Grasp and Release Mode.

In preferred embodiments of Continuous Passive Motion Mode, speed, force, range of motion and number of cycles may be programmed by a clinician for each moving joint. Splinting or locking can be applied to each non-moving joint. The user will be able to begin their individual therapeutic program, for example, via a button press at the portable programmer unit, or using an analogue shoulder stick, an external pressure sensor, voice activation or other suitable means. An analogue shoulder stick may also be used to control the speed of hand closure.

The number of cycles may be between 1 and 10000 or between 1 and 5000 or between 1 and 1000 or between 1 and 500, or between 1 and 100 or between 1 and 50 or between 1 and 40 or between 1 and 30 or between 1 and 20 or between 1 and 10, and may be about 1, 2, 3, 4, 5, 10, 15, 20, 30, 40, 50, 75, 100, 150, 200, 250, 300, 350, 400, 450, 500, 600, 700, 800, 900, 1000, 1500, 2000, 2500, 3000, 4000, 5000, 6000, 8000 or 10000. The time for each cycle may be between 1 second and 10 minutes or between 1 second and 5 minutes or between 1 second and 1 minute or between 1 and 50 seconds or between 1 and 40 seconds or between 1 and 30 seconds or between 1 and 20 seconds or between 1 and 10 seconds, and may be about 1, 2, 5, 10, 15, 20, 25, 30, 40, or 50 seconds or about 1, 2, 3, 4, 5, 6, 7, 8, 9 or 10minutes.

In preferred embodiments of Grasp and Release Mode, programming for the movement of each joint may be performed in a series of steps. Initially, a clinician can program the preferred combination embodiments to produce an open hand. Subsequently, the order of operation of joints necessary for hand closure in a particular hand grasp configuration can be programmed. The degree of flexion for each joint can be programmed for each desired hand grasp configuration. The speed of overall hand closure can then be established and programmed. Subsequent to programming, hand closure and opening can be achieved by the user pressing a button on the programmable unit.

In another mode of operation, the combination embodiments can also be programmed such that certain joints are splinted or held stiff with coactivation of opposing movement facilitation devices.

In a third aspect, the present invention provides a rehabilitation glove for facilitating movement of a patient's metacarpophalangeal, proximal interphalangeal and distal interphalangeal joints, said glove having:

(a) a support structure for enveloping at least the patient's fingers and thumb, said support structure formed of a plurality of strut members positioned so as not to interfere with finger and thumb movement;

(b) at least one movement means corresponding to each of the joints, said movement means coupling at least a first strut member;

(c) at least one movement facilitation device corresponding to each of the movement means, said movement facilitation device having at least one actuator, a first part of the actuator coupled to a first portion of the first strut member, said actuator for moving said first strut member thereby causing movement of the joint, and an operating means coupled to the actuator for operating the actuator.

In some preferred embodiments, the rehabilitation glove additionally facilitates movement of a patient's wrist joints.

In an embodiment, the invention provides a system for applying Continuous Passive Motion therapy to a hand of a patient, comprising:

a movement device according to the invention;

a control system comprising a user interface and an internal CPU containing control software;

one or more force and position transducers connecting to the movement facilitation device; and a power supply.

In some of these preferred combination embodiments, the support structure additionally has at least a second strut member and the movement means couples the first strut member to the second strut member. In such embodiments, operation of the actuator causes the first strut member to move relative to the second strut member, thereby causing movement of the joint. In further preferred embodiments, a second part of the actuator is coupled to a second object.

The discussion of preferred combination embodiments has focussed on the use of such embodiments for the hand. As indicated earlier, the device of preferred embodiments may be used with all the joints in a human or non-human animal or a mimic thereof. Accordingly, combination embodiments may be specifically designed to accommodate other parts of the body including, for example, feet, legs, hips, back, neck and jaw.

In a fourth aspect, the present invention provides a process for causing movement between a first portion of a first object and a second portion of the first object, said process comprising:

(a) providing a movement facilitation device having:

at least one actuator, a first part of the actuator coupled to the first portion of the first object, said actuator for moving said first portion with respect to the second portion, and an operating means coupled to the actuator for operating the actuator; and (b) operating the operating means, thereby causing the actuator to move the first portion relative to the second portion.

In an embodiment the invention provides a process for causing movement between a first portion of a first object and a second portion of the first object, said process comprising:

(a) providing a movement facilitation device according to this invention; and (b) operating the operating means, thereby causing the actuator to move the first portion relative to the second portion.

In a further aspect of the invention there is provided an actuator capable of incremental actuation. Said actuator may comprise at least one movement control means in operational association with one or more actuation means, wherein said actuation means comprise a shape memory material or a conducting polymer, whereby displacement of a movement control means is promoted by change in dimension of the shape memory material or the conducting polymer. There is also provided a movement facilitation device according to the invention, said device comprising an actuator according to this aspect.

The movement control means may be any suitable means may be used that is capable of allowing movement in one direction and of restricting movement in the opposite direction, for example a ratchet, a gearing mechanism, a friction device or an electronically controlled mechanism.

In still a further aspect of the invention there is provided a transducer for determining an applied force comprising:

a radiation source and one or more detectors, and a return mechanism coupled to the one or more detectors, wherein each of the one or more detectors is capable of generating a signal dependent on an intensity of radiation incidental on said detector, and wherein a distance between the radiation source and a detector is a function of the force applied to the return mechanism. The radiation source and the one or more detectors may be disposed in an enclosure, and the enclosure may be opaque. The enclosure may be in the form of a cylinder or a tube or a box or it may be some other means for at least partially excluding the radiation. The radiation may be any safe energy form that dissipates over distance and can be detected readily, for example light, infra-red, magnetic, ultrasonic or electromagnetic. The radiation source may for example be a light emitting diode. The return mechanism may for example be a spring or a torsion bar or an elastic device.

BRIEF DESCRIPTION OF THE DRAWINGS

FIG. 6 is a graph of electrolytic efficiency against polymer thickness of a film of polypyrrole on a glassy carbon disc electrode obtained using an applied voltage of 1.0 V~+0.50 V with a pulse width of 250 msec;

FIG. 7(a) is a graph comparing stress generated by unplatinised and platinised polypyrrole films;

FIG. 7(b) is a schematic diagram illustrating the effect of iR (voltage) drop on the actuation of polypyrrole film;

Figure 19:
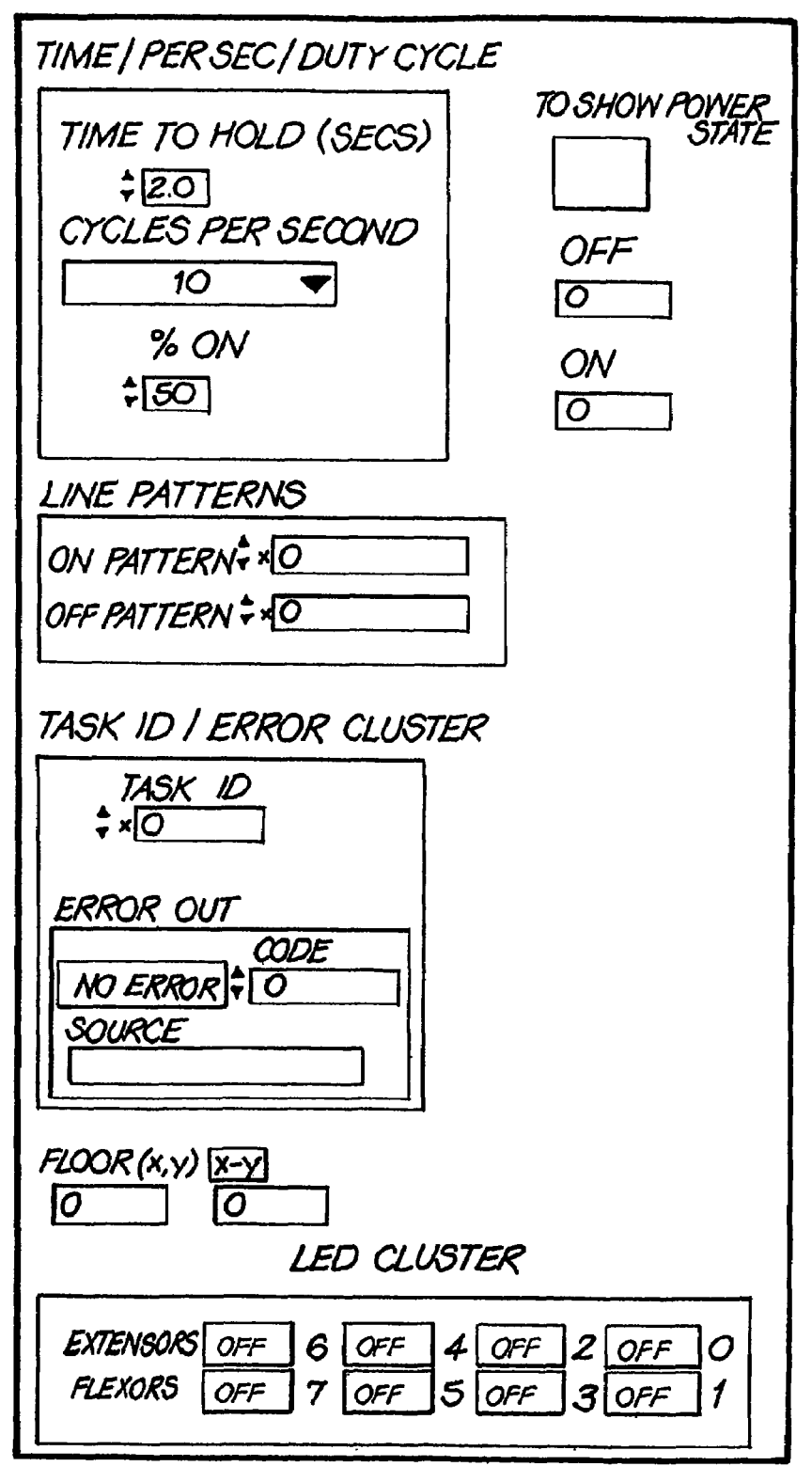

FIG. 19 is a front panel view or user interface of the software of preferred embodiments programmed with a "pulse percent on" configuration.

FIG. 20 is a further front panel view or user interface of the software of preferred embodiments programmed with a "pulse percent on" configuration.

DETAILED DESCRIPTION OF PREFERRED EMBODIMENTS OF THE INVENTION

Figure 1:
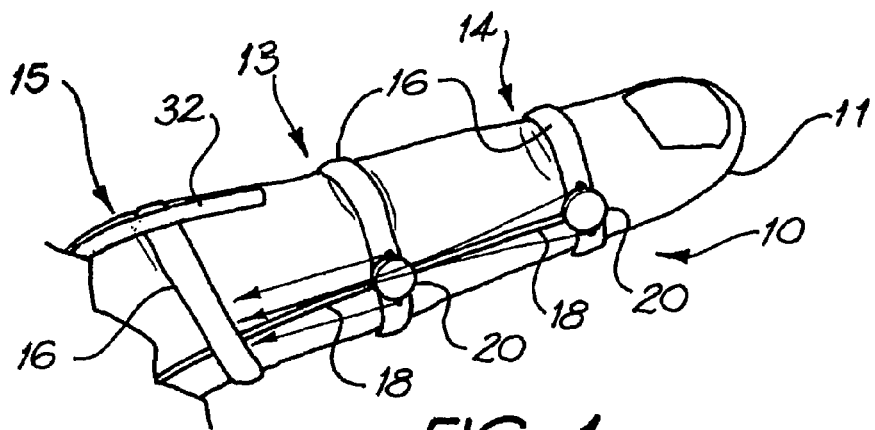
FIG. 1 is a schematic representation of one combination embodiment having a plurality of movement facilitation devices, said combination embodiment being worn on the finger of a patient.

Preferred combination embodiments include a structure 10, such as a support structure, surrounded by cloth-like material. In some preferred combination embodiments, the support 10 may be incorporated into and around dressings that need to be applied to an injured hand. In other preferred combination embodiments, the support structure 10 sits outside the hand 12 and is built into a glove member 25. The preferred combination embodiment is then secured at the proximal interphalangeal 13 and distal interphalangeal 14 joints by firm bands 16 (which may be slightly elasticised to ensure their secure placement at the desired position about the finger 11) or anchoring connectors, for attachment to bandaging or casts.

Figure 2:
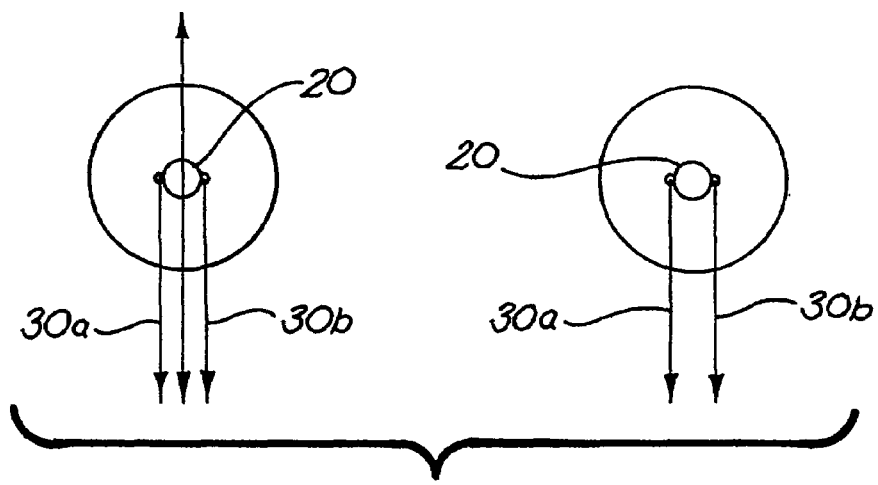
FIG. 2 is an enlarged view of the coupling arrangements for movement facilitation devices at the distal and proximal interphalangeal joints of the finger, for the combination embodiment of FIG. 1.
Figure 3:
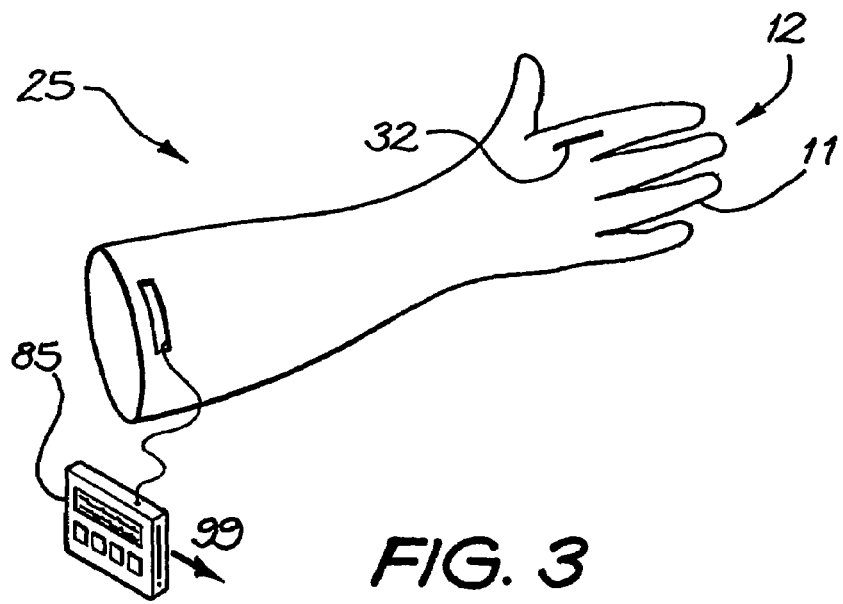
FIG. 3 is a schematic representation of one preferred combination embodiment having a glove member, and illustrates the pager-sized, battery powered programmable, portable operating means.

The support structure 10 has a plurality of movement means 20, such as a hinge, that sit on both sides of each of the proximal interphalangeal 13 and distal interphalangeal 14 joints. These hinges 20 are held together by strut members 18 at the sides of the fingers 11. The hinges 20 are to be lockable so that the position of each joint can be maintained fixed whilst force is being applied. The metacarpophalangeal joints 15 may be splinted by inserting rods 32 into the glove member 25 on a dorsal side. The actuator 30 (see 30a and 30b on FIG. 2) passes directly over, or is attached close to, the hinges 20 to move the proximal interphalangeal 13 and distal interphalangeal 14 joints.

For the operation of the metacarpophalangeal joints 15, the actuator 30 (see 30a and 30b on FIG. 2) may be attached to the firm band 16 just distal to the metacarpophalangeal joint 15 on both dorsal and volar aspects of the glove member 25. At the hinges 20, agonist 30a and antagonist actuators 30b can act at a small radius from a longitudinal axis 50 associated with the finger 11 to produce a large movement.

Some preferred actuators are those of the electromechanical type. Electromechanical actuators based on inherently conducting polymers (ICPs) can be viewed as simple electrochemical cells in which the application of a potential creates dimensional changes in one or more of the electrode materials. The ability to efficiently inject or extract charge from the polymer(s) utilised without mechanical degradation of the system determines the overall actuator performance possible.

Hence, the electrochemical properties of polymer(s) utilised dictate the level of performance obtainable.

Conducting polymers are oxidised/reduced according to Equations (1) and (2) set out below using polypyrrole as an example:

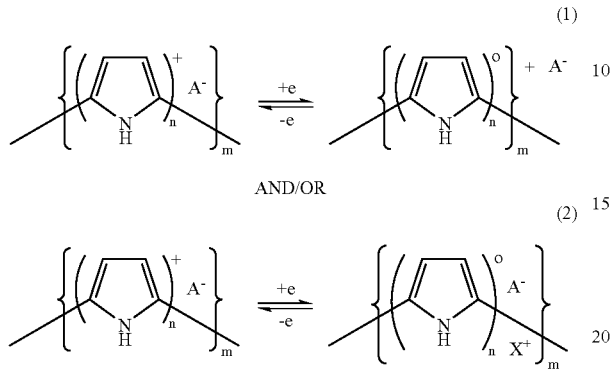

AND/OR $A^-$ is a dopant anion, $X^+$ is a cation from the supporting electrolyte, n is an integer of from 1 to X and is most usually 3 or 4. The symbol m represents the number of repeat units of the polymer thereby determining the molecular weight of the polymer.

Figure 4:
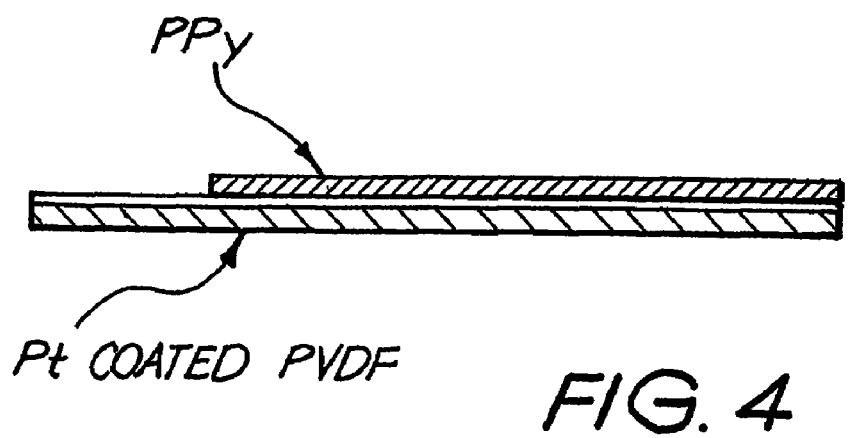
FIG. 4 is a schematic representation of a electromechanical actuator in the form a bimorph comprising a laminate structure formed by electrochemically polymerising polypyrrole onto a platinum coated PVDF membrane.
Figure 5:
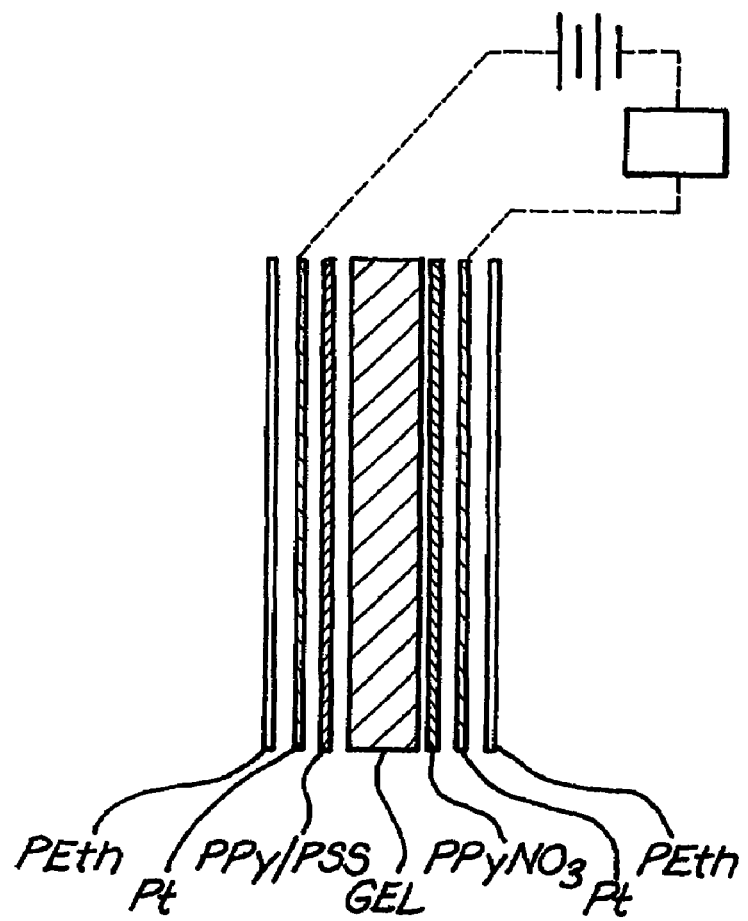
FIG. 5 is a schematic representation of an axial force electromechanical actuator.

For small mobile anions ($A^-$) the process described by Eq. 1 predominates whereas for larger immobile anions (such as polyelectrolytes), processes described by Eq. 2 will predominate. In practice, for most anions, a mixture of both processes occurs. Accompanying anion expulsion (Eq. 1) is a decrease in volume of the conducting polymer. Alternatively, if cations are incorporated into the polymer (Eq. 2) during the redox reaction, the volume of the polymer increases[1]. These dimensional changes may be translated into a bending motion using a bimorph[2] as illustrated in FIG. 4, or a uniaxial force[3] using an appropriate configuration as for example illustrated in FIG. 5.

To maximise energy efficiency, the conducting polymer should be oxidised/reduced at minimal potentials and the process not be limited by kinetic effects.

However, with all conducting polymers the latter is an inherent limitation since movement of ions through the electrolyte and polymer is diffusion controlled.

Transitions induced by polymer oxidation/reduction may have an effect on the ability of a polymer to actuate[4]. For instance, a polymer becomes more resistive (that is, resistance R increases) with electrochemical reduction making subsequent reduction or oxidation more difficult since:

$$E = E_{app} - iR \quad (3)$$

where E is the potential at the polymer, Eapp is the potential applied by an external power source and i is the current. Change in the electronic properties of the polymer makes efficient charge injection throughout the polymer, especially to the reduced state, desirable.

Chemical properties of a polymer can also change dramatically with properties such as hydrophobicity being dependent on the oxidation state[4]. This, in turn, influences which electrochemical mechanism (Eq. 1 or 2) predominates. For example, if hydrophobicity of a polymer dramatically increases upon reduction it is easier to extract anions from the polymer than inject highly hydrated cations into the polymer. In addition, mechanical properties of a polymer can be greatly influenced by the potential applied[5] and hence, the redox state of the polymer. In this regard, a polymer can become significantly more ductile in the reduced state, and such changes in mechanical properties may well influence the efficiency of an electromechanical actuator. The above illustrates that actuator performance and efficiency are dependent on the ability to inject or extract charge from the polymer with low energy consumption. The ease of charge injection/extraction is reflected in a parameter denoted as electrolytic efficiency (EE). The electrolytic efficiency is a measure of the ability to access all the available electrochemical sites of a polymer that can contribute to actuation. Specifically, the electrolytic efficiency of a system can be defined as:

$$EE_{ox} = \frac{\text{Charge passed during oxidation}}{\text{Charge for complete oxidation}^{(a)}} \times 100$$

$$EE_{red} = \frac{\text{Charge passed during reduction}}{\text{Charge for complete reduction}^{(a)}} \times 100$$

(a) Estimated from charge consumed during growth and assuming n=3 in Eqs. (1) and (2).

The effect of polymer thickness on electrolytic efficiency of a polymer film deposited on a glassy carbon disc electrode (ie. with substantially ideal electrical connection) is shown as a function of polymer thickness in FIG. 6. The polymer used in this study was polypyrrole. From the graph, it is clear that only a very thin film (<0.27 μm) gave high electrolytic efficiency. This corresponds to an electrode contact surface area to polymer volume ratio of $3.7 \times 10^4$ cm$^2$/cm$^3$. Generally, however, only freestanding films of a thickness greater than about 4 μm have adequate mechanical properties for actuation.

While the polymer(s) and electrolyte used determine the maximum performance of an electromechanical actuator that can be expected, practical issues such as the efficiency of the electrical connection to the actuator may also be a limiting factor.

Improvement in actuation performance may be obtained by platinising a conducting polymer film in order to minimise iR (ie voltage) drop effects along the length of the actuator as indicated in FIGS. 7(a) and 7(b). In particular, an unplatinised polymer film was found to produce approximately 0.5 MPa stress during isometric testing. In contrast, when contraction was induced by electrochemical stimulation, an identical platinised film generated 3 MPa stress.

For most efficient performance an electromechanical actuator should not only allow efficient injection and extraction of charge, but should also desirably enhance or at least not interfere with the mechanical and electromechanical properties of the device. In the example illustrated in FIG. 7, although enhanced electrical connection to the polymer was obtained, the coating of the polymer with platinum (sputter coating) markedly decreased the strength of the polymer film.

Figure 8:
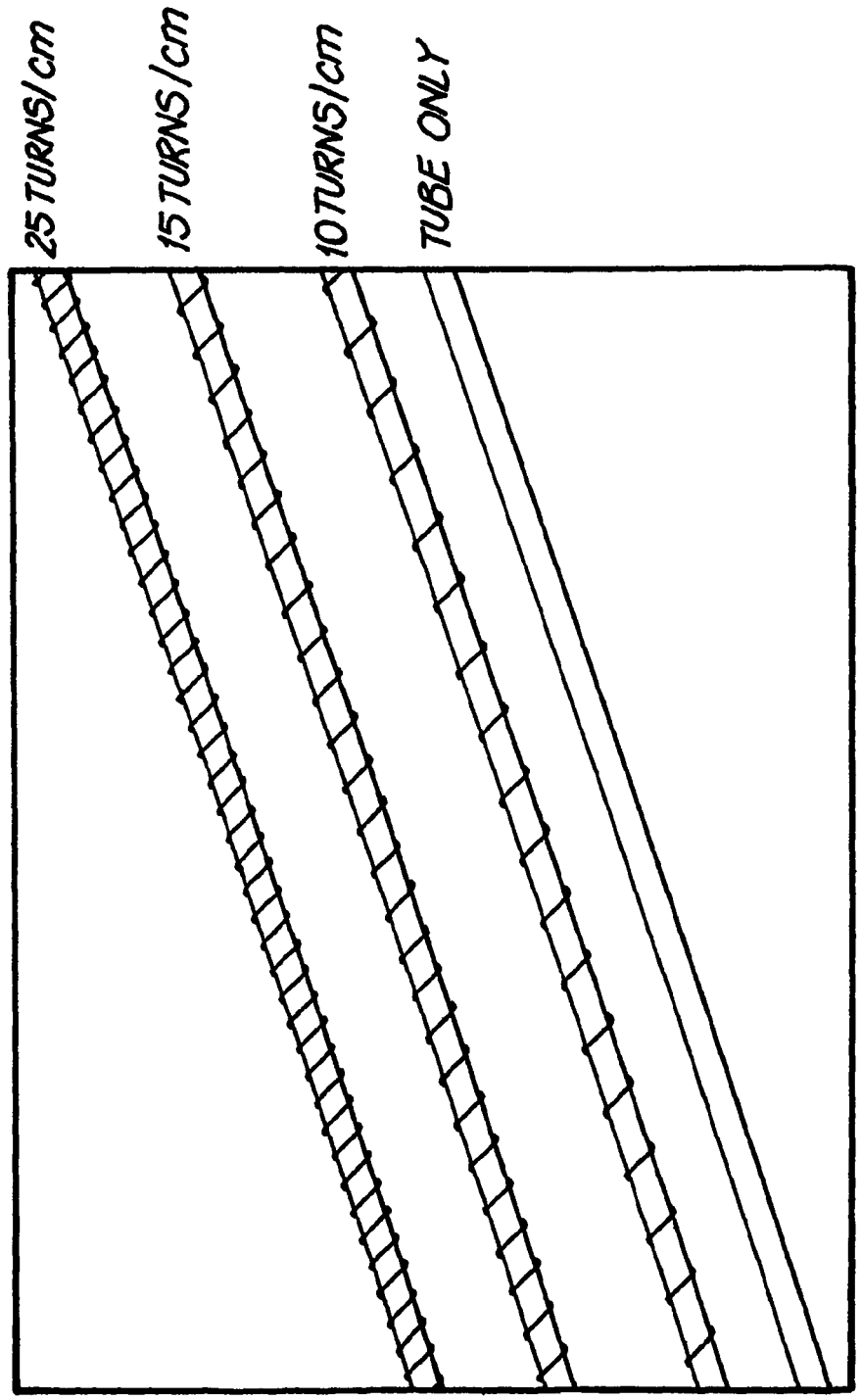
FIG. 8 is a partial side view of electromechanical actuators embodied by the present invention.

Electromechanical actuators of the present invention formed of appropriate polymers are illustrated in FIG. 8. In particular, the embodiment illustrated by A comprises a tube of polypyrrole (PPy) alone. The further actuators indicated by B, C and D comprise a tube of the polymer incorporating a longitudinally extending helix formed by a conductor comprising platinum wire. While platinum is used in the present example, the wire may be made from other suitable metals. Indeed, the wire may be formed from conducting materials other than metal. In the actuators shown, the pitch of the helical wire for embodiment B is 10 turns cm$^{-1}$, while the pitch for embodiments C and D is 15 turns cm$^{-1}$ and 25 turns cm$^{-1}$, respectively.

Figure 9:
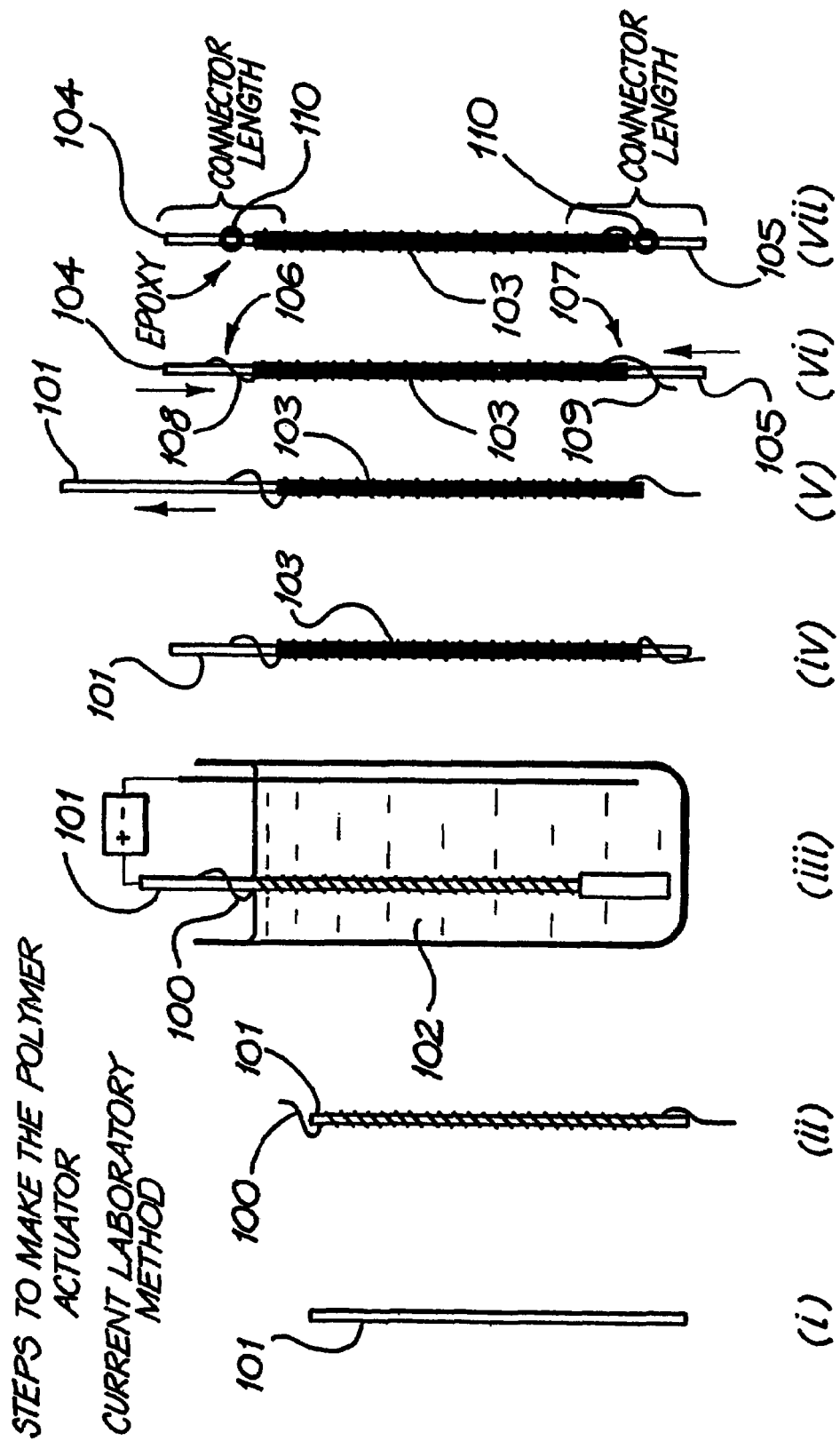
FIG. 9 is a schematic representation illustrating the manufacture of an electromechanical actuator of the present invention.

The manufacture of preferred electromechanical actuators will now be described with reference to FIG. 9. Briefly, a conductor comprising a 25 μm platinum wire 100 is wrapped around a straight 125 μm platinum wire template 101 to form a helix therealong. The conductor and template wires are then placed in a polymer electrolyte solution 102 and electroplated for 24 hours at −28° C. to form a tube of polymer 103 around the template wire 101 and conductor wire 100 as indicated in step (iii), prior to removing the formed polymer tube 103 from the electrolyte solution 102 as indicated in step (iv). The template wire 101 is then slid from the polymer tube 103 prior to electrical connectors in the form of short inserts 104 and 105 of 125 μm platinum wire being inserted into each end 106 and 107 of the polymer 103 as indicated in steps (v) and (vi). Each end of a connector wire 108 and 109 is then wrapped tightly around the corresponding short wire insert 104 or 105, and fixedly glued in position thereon by an epoxy resin 110 as indicated in step (vii).

If desired, the template wire 101 may be left in position within the longitudinally extending interior passageway of the polymer tube 103 rather than removing it as indicated above.

Figure 25:
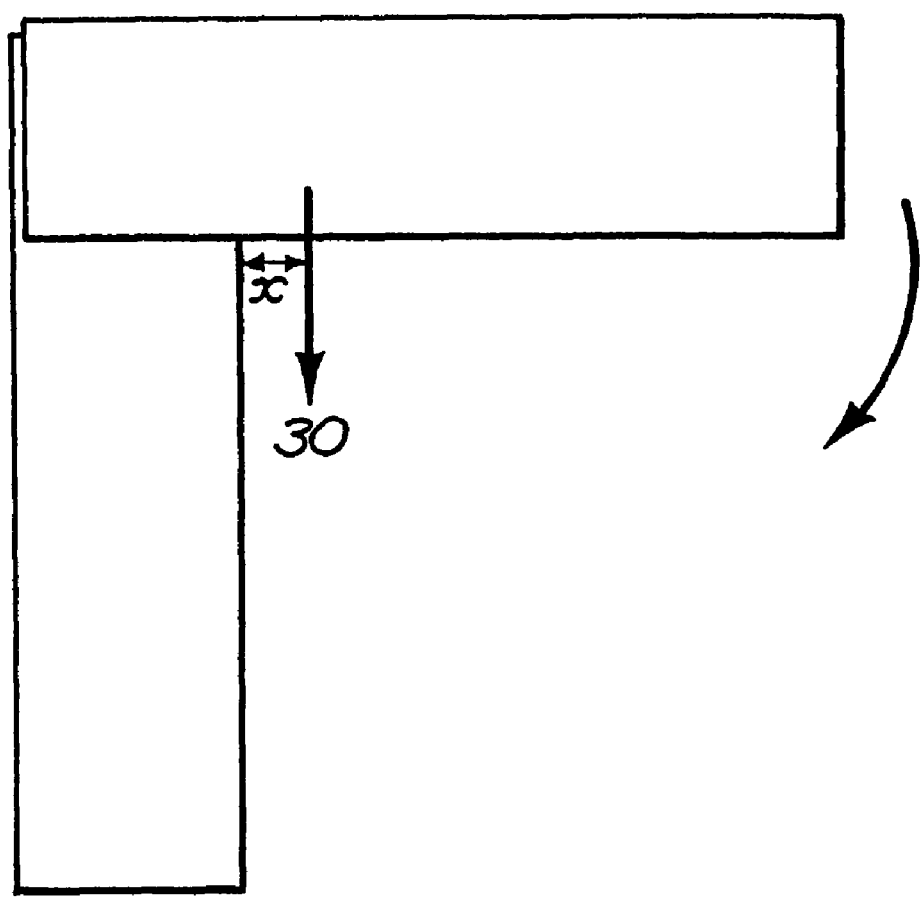
FIG. 25 is a schematic representation of a joint illustrating the relative radius from the axis of movement of the joint from which the actuator preferably exerts force on the first object.

As suggested above, in some preferred embodiments, by attaching the actuator at a small radius from an axis of movement, a small change in the actuator's length can cause a significant movement in the first object (see FIG. 25 in which "X" illustrates the small radius from the axis of movement of the joint from which the actuator 30 applies a force and as a result of which the actuator 30 is capable of causing a large movement in the joint). Accordingly, where the device is being used, for example, on a finger joint, a 5% reduction in length of the actuator may achieve full flexion of the finger joint, when the actuator is coupled as described above. Note also that coactivation of agonist 30a and antagonist actuators 30b across a joint is a mechanism by which "splinting" of that joint may be achieved. Alternatively, "splinting" may be achieved by locking the mechanical joint, or both agonist and antagonist activation cables, in place using a mechanism which may for example be a manually activated lever or a switch operated electromechanical device. These alternatives are not shown in the Figure.

Actuators 30 acting at the distal interphalangeal joint 14 will pass through the proximal interphalangeal 13 hinge 20 directly over its longitudinal axis 50.

The wrist joint (not specifically illustrated) may have actuators 30 acting across it which are also attached to the glove member 25 and/or structure 10 and/or bandaging or cast.

Preferred combination embodiments are powered and controlled by a portable, pager-sized, battery powered programmable operating means 85. The operating means 85 may be interfaced to a computer for therapist programming 99.

Figure 11:
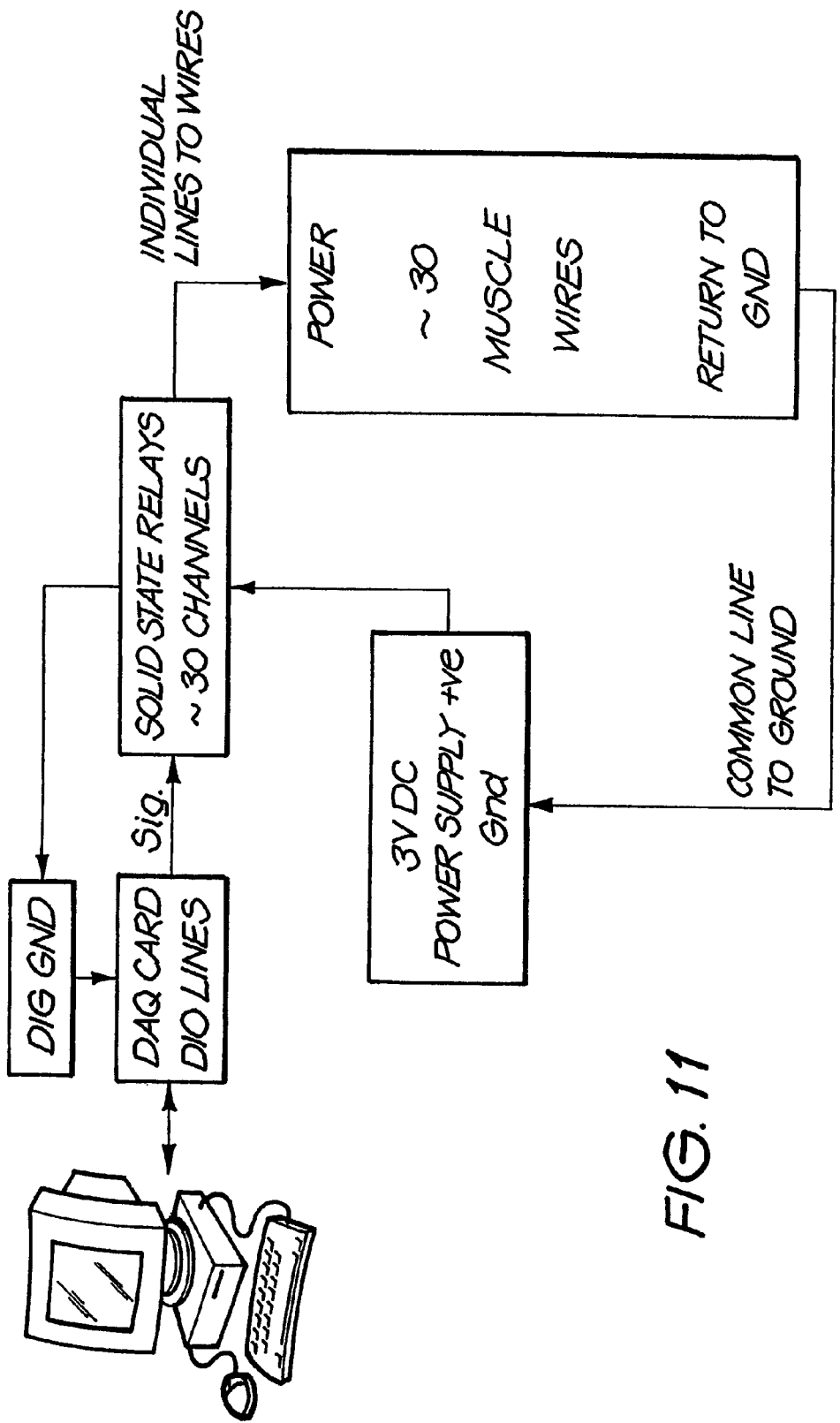
FIG. 11 is an illustration a basic circuit layout for one preferred embodiment of the operating means from the present invention.
Figure 12:
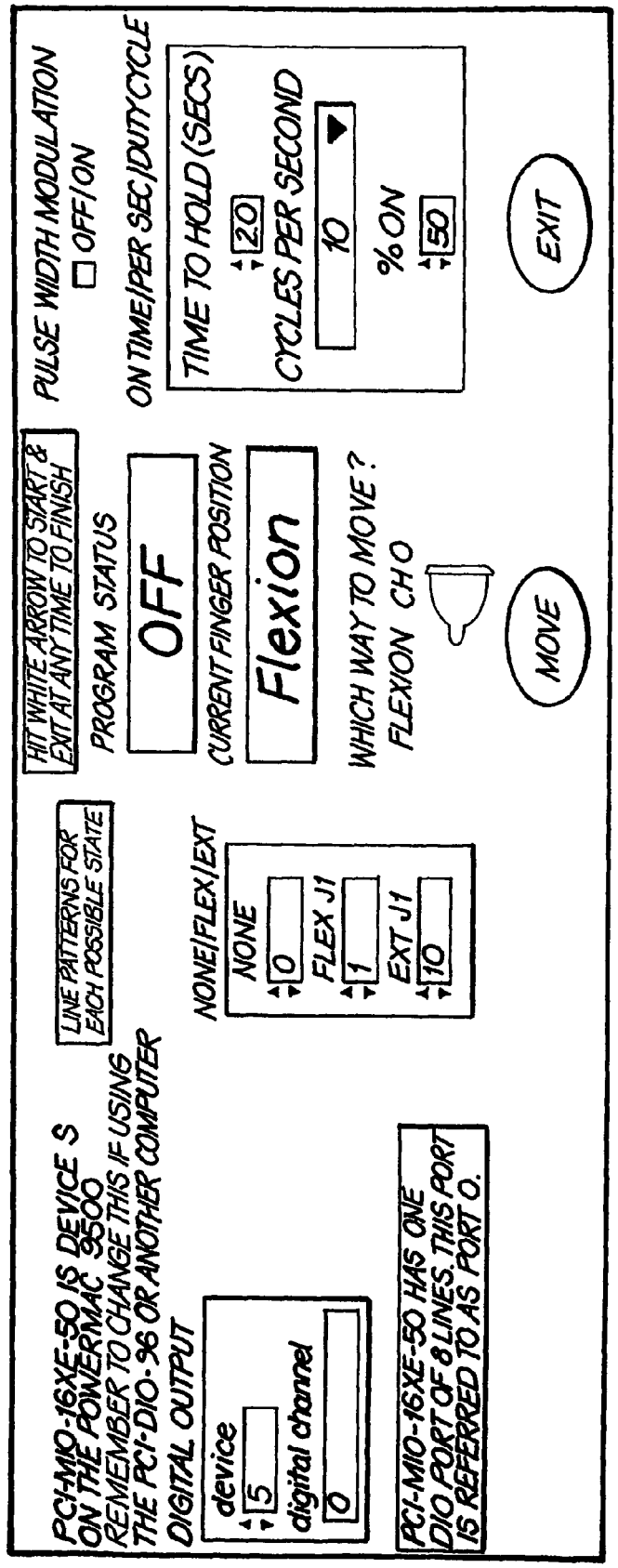
FIG. 12 is a front panel view or user interface of the software of the present invention which is programmed with a two wire configuration.
Figure 13:
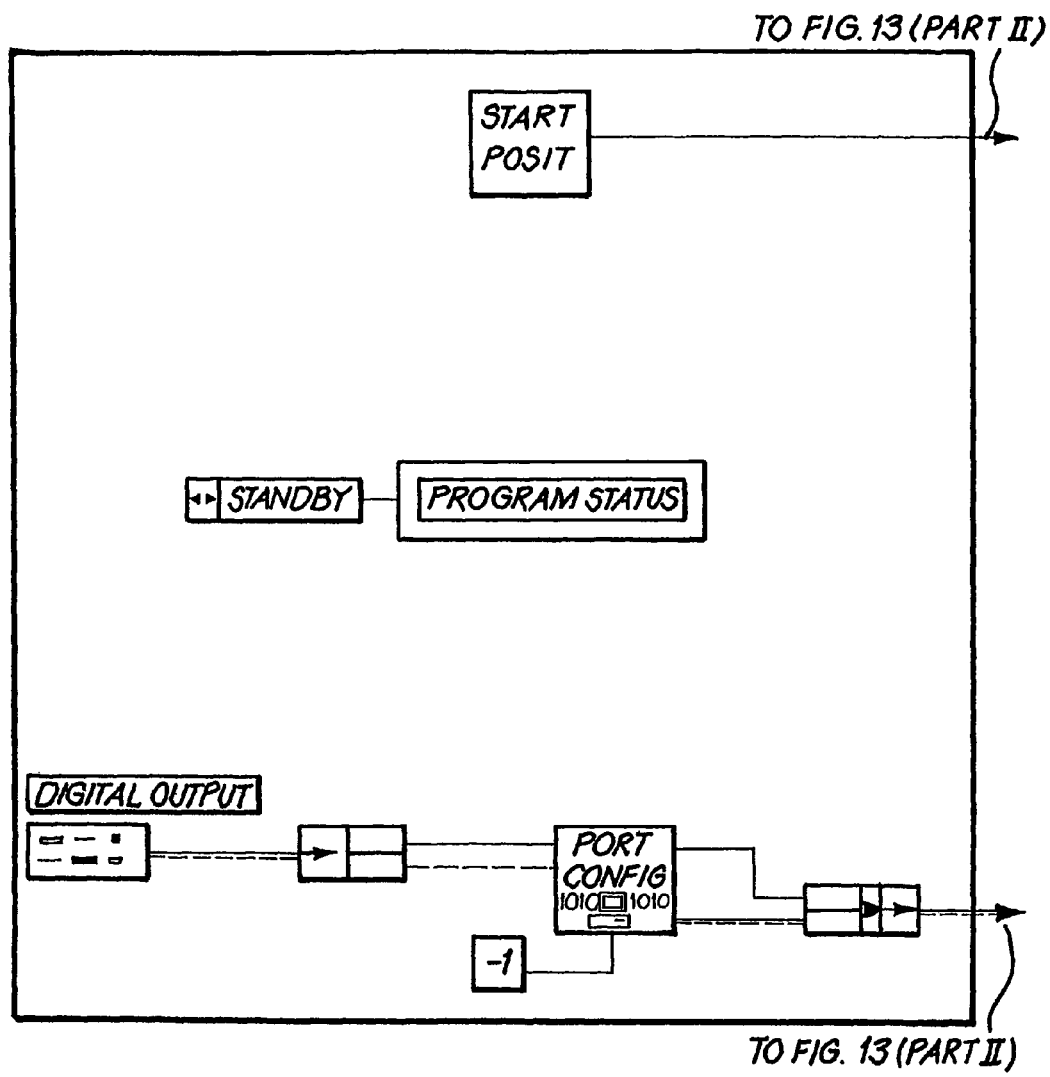
FIG. 13 is the graphical programming code corresponding to the front panel of FIG. 12.
Figure 14:
FIG. 14 is a further graphical programming code corresponding to the front panel of FIG. 12.
Figure 15:
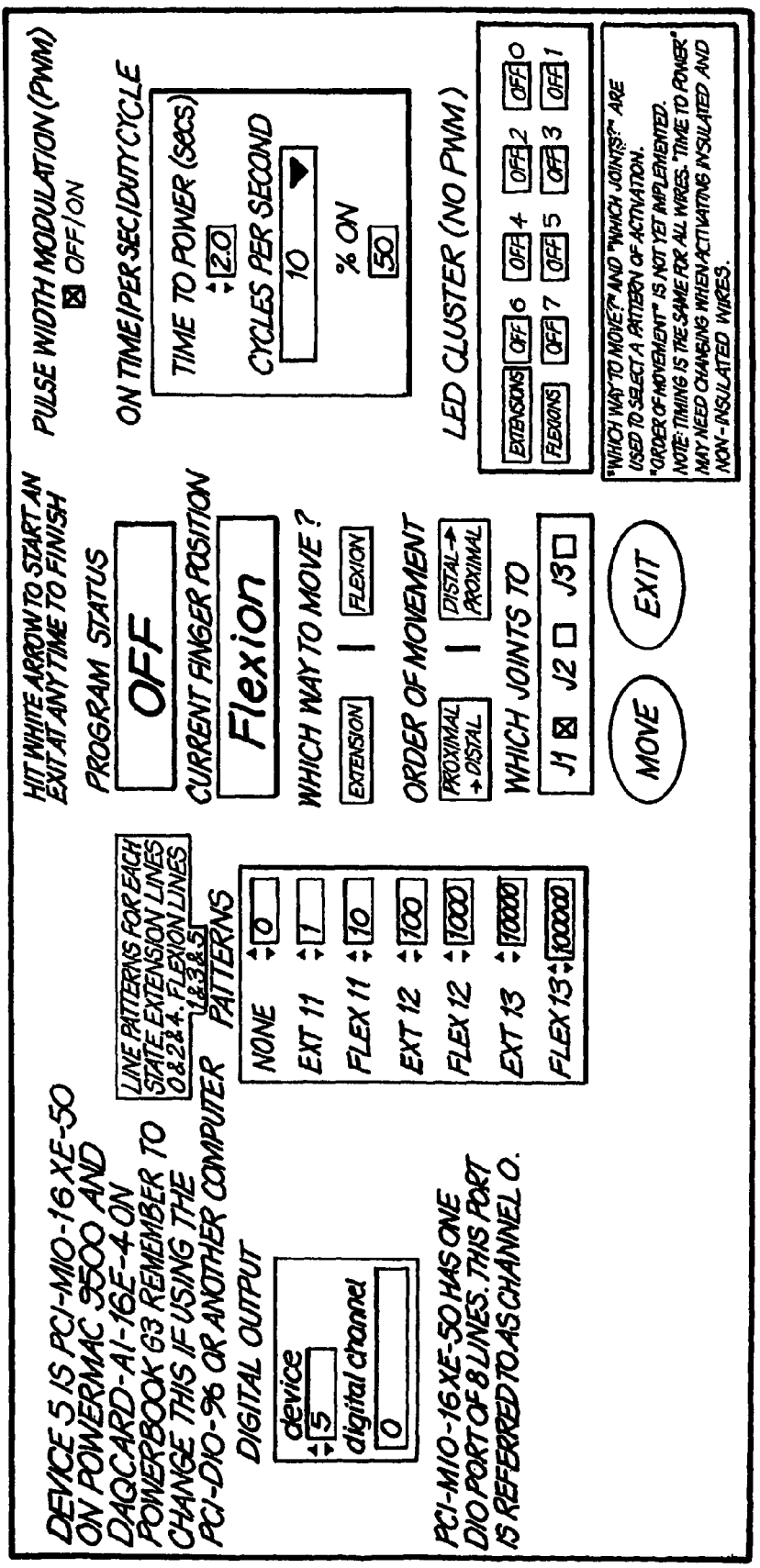
FIG. 15 is a front panel view or user interface of the software of preferred embodiments programmed with a three joint configuration.
Figure 16:
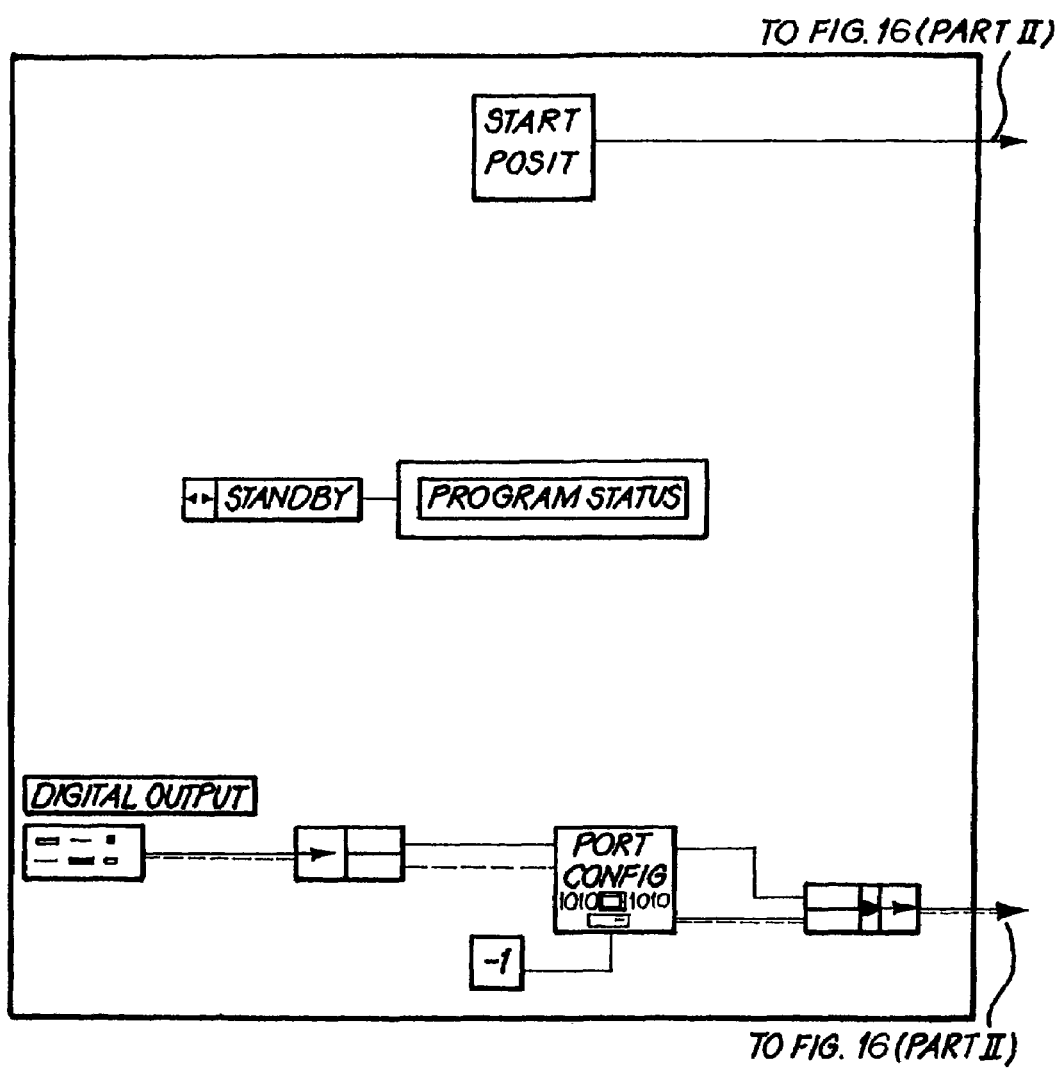
FIG. 16 is a graphical programming code corresponding to the front panel of FIG. 15.
Figure 16:
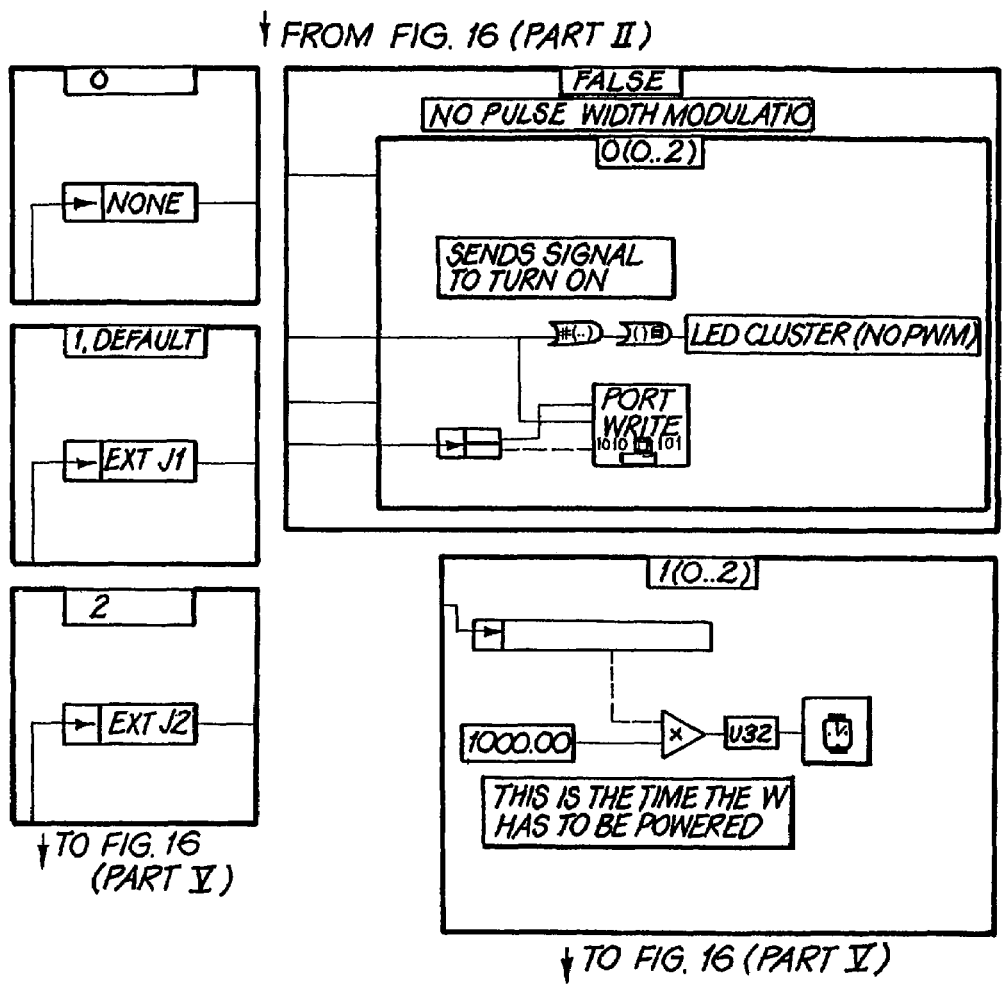
Figure 17:
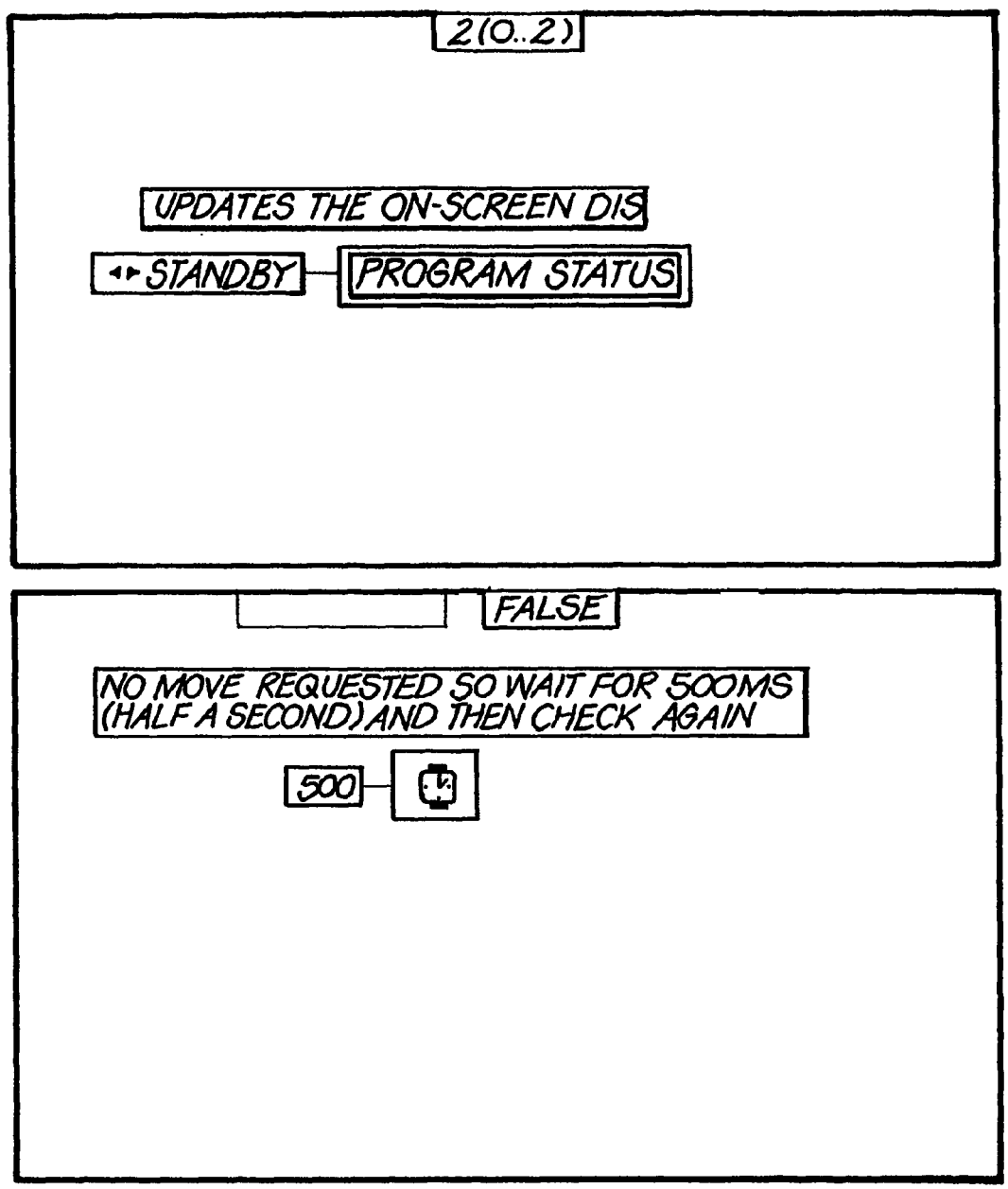
FIG. 17 is a further graphical programming code corresponding to the front panel of FIG. 15.
Figure 18:
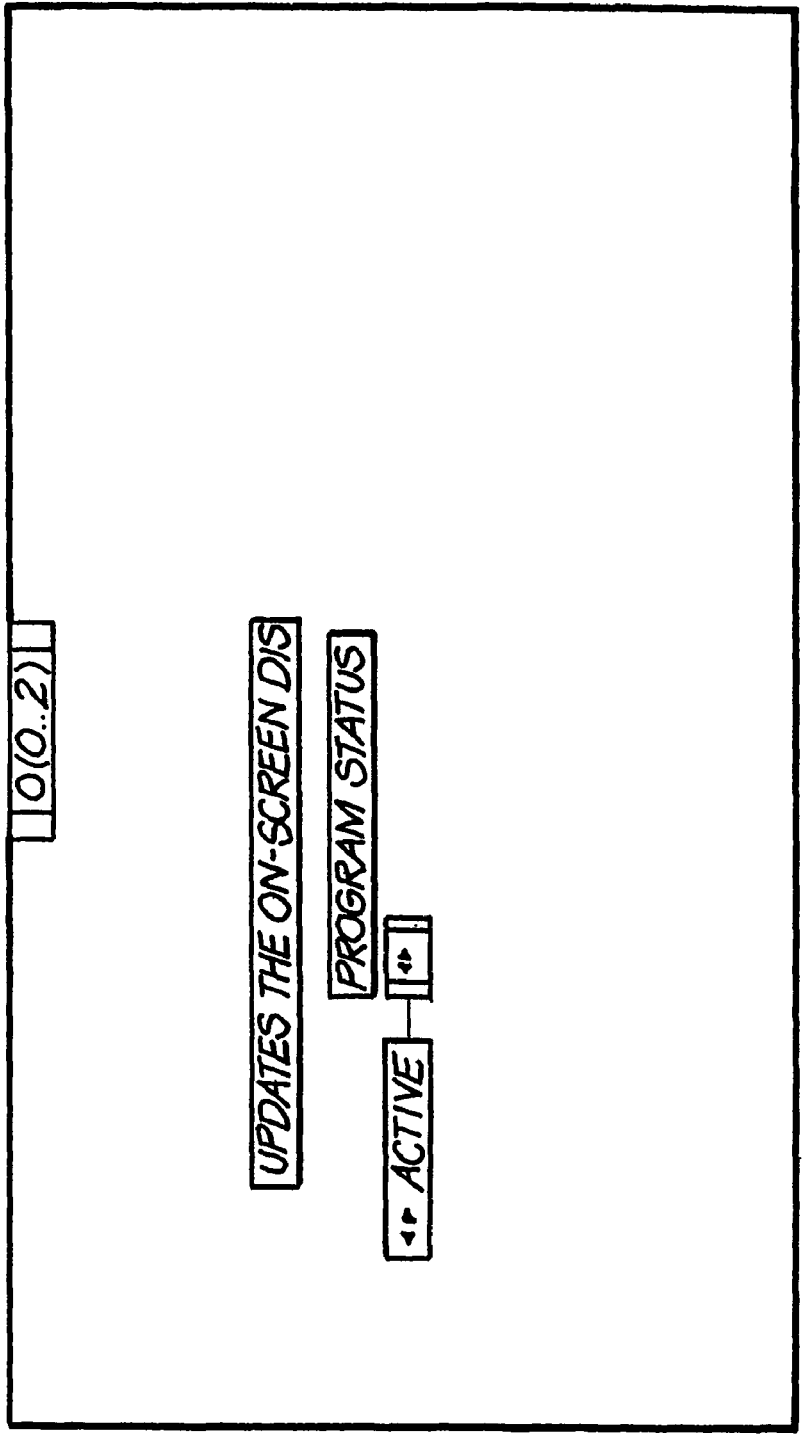
FIG. 18 is a further graphical programming code corresponding to the front panel of FIG. 15.
Figure 21:
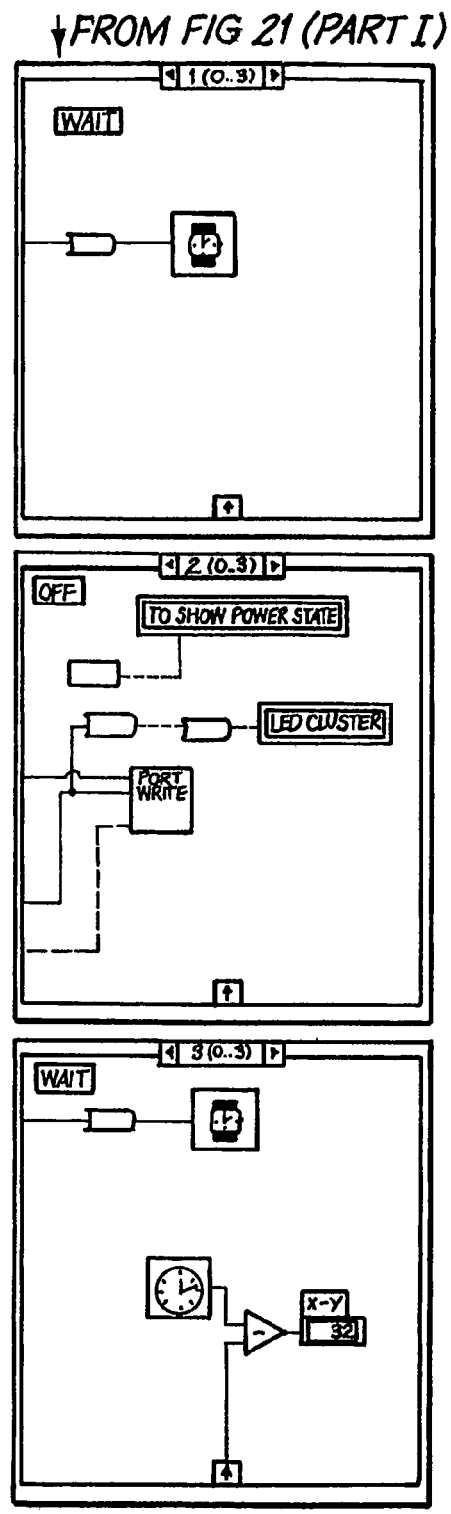
FIG. 21 is the graphical programming code corresponding to the front panels of FIGS. 19 and 20.
Figure 22:
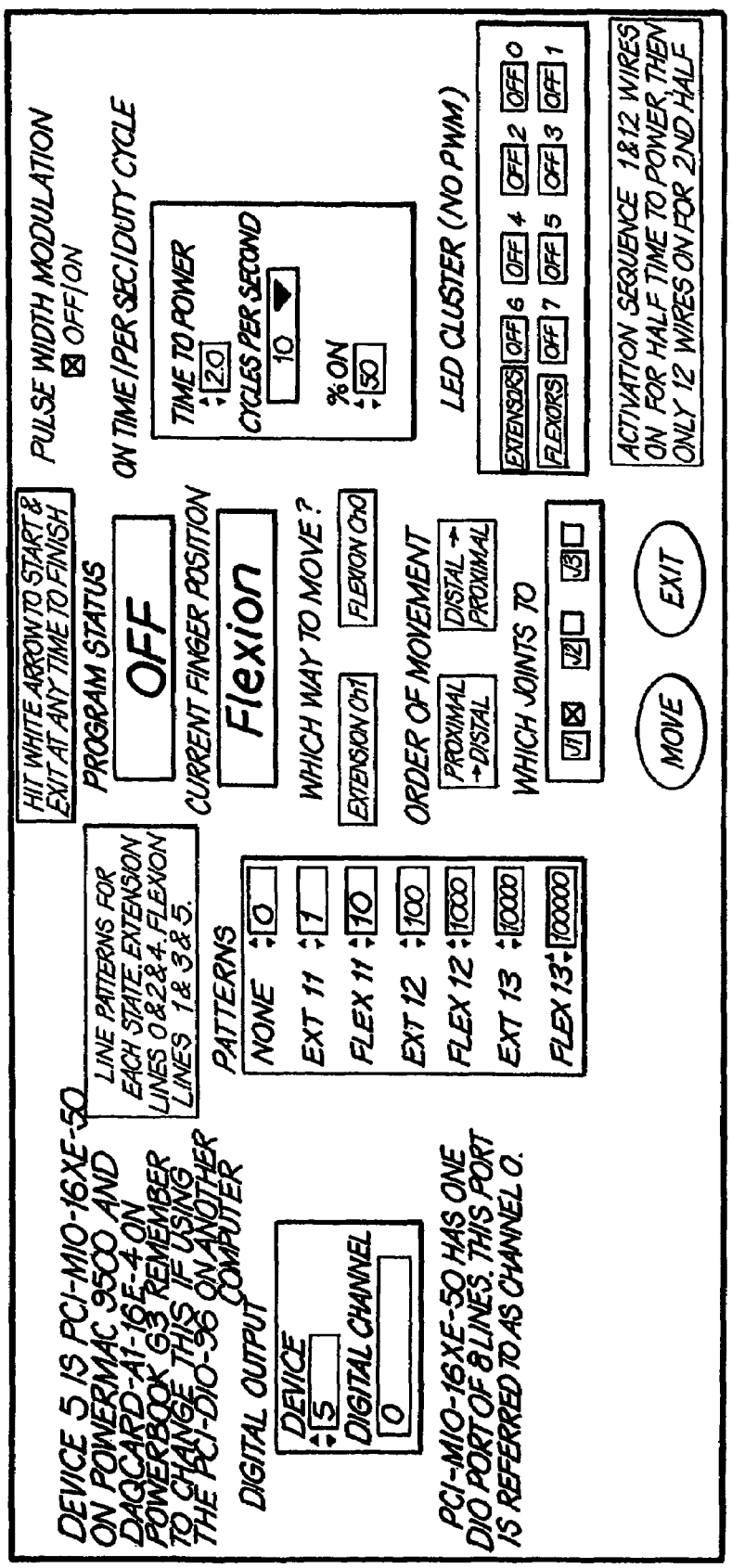
FIG. 22 is a front panel view or graphical interface of the software of preferred embodiments programmed with a four wire configuration.
Figure 23:
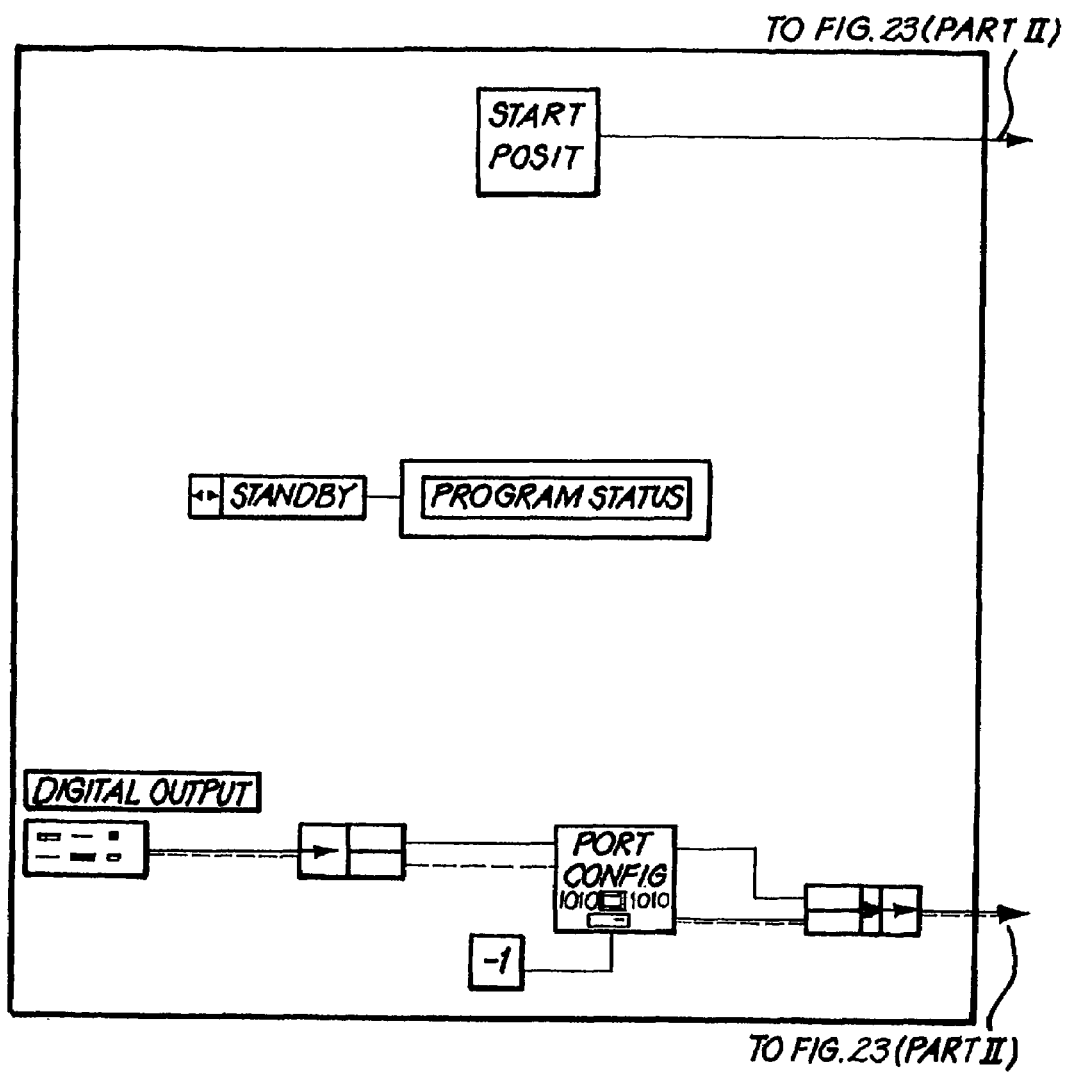
FIG. 23 is the graphical programming code corresponding to the front panel of FIG. 22.
Figure 23:
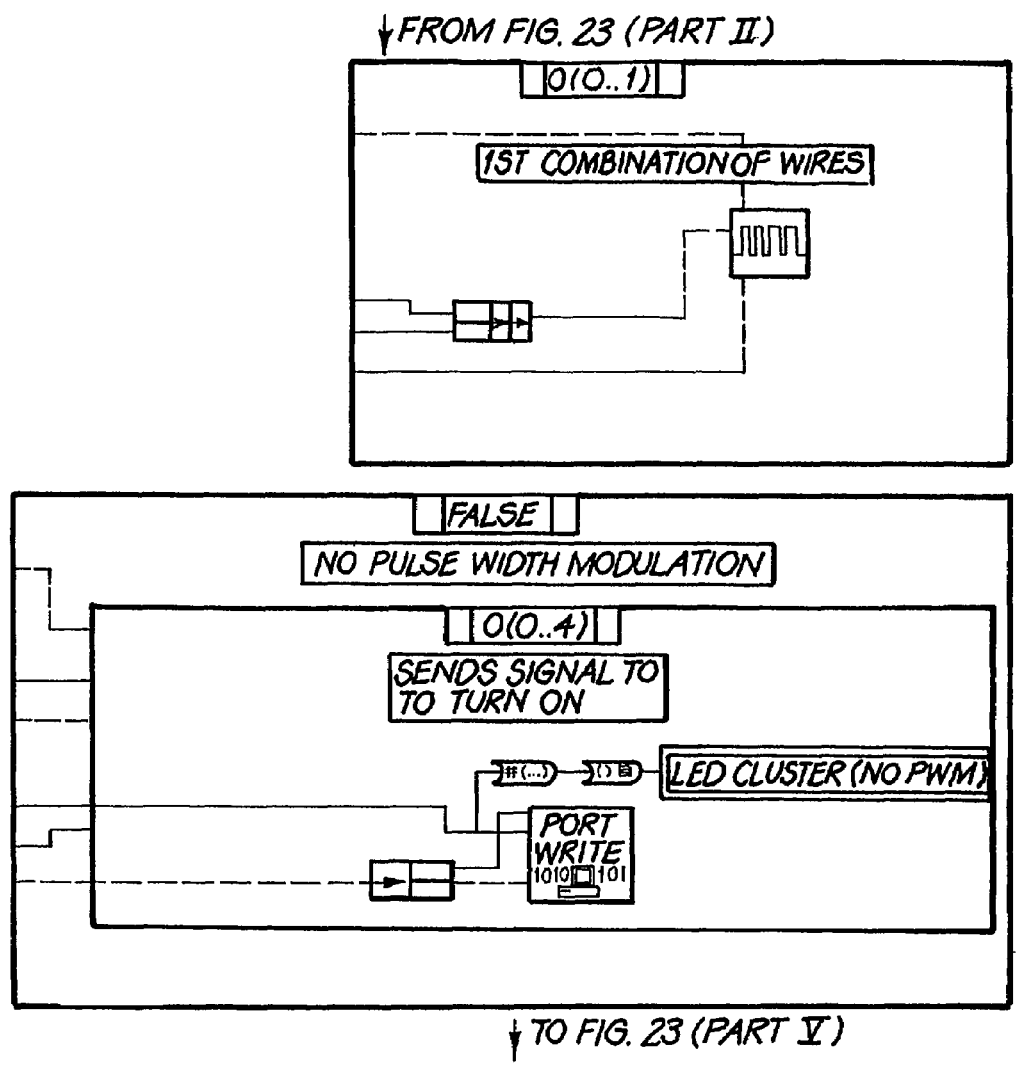
Figure 24:
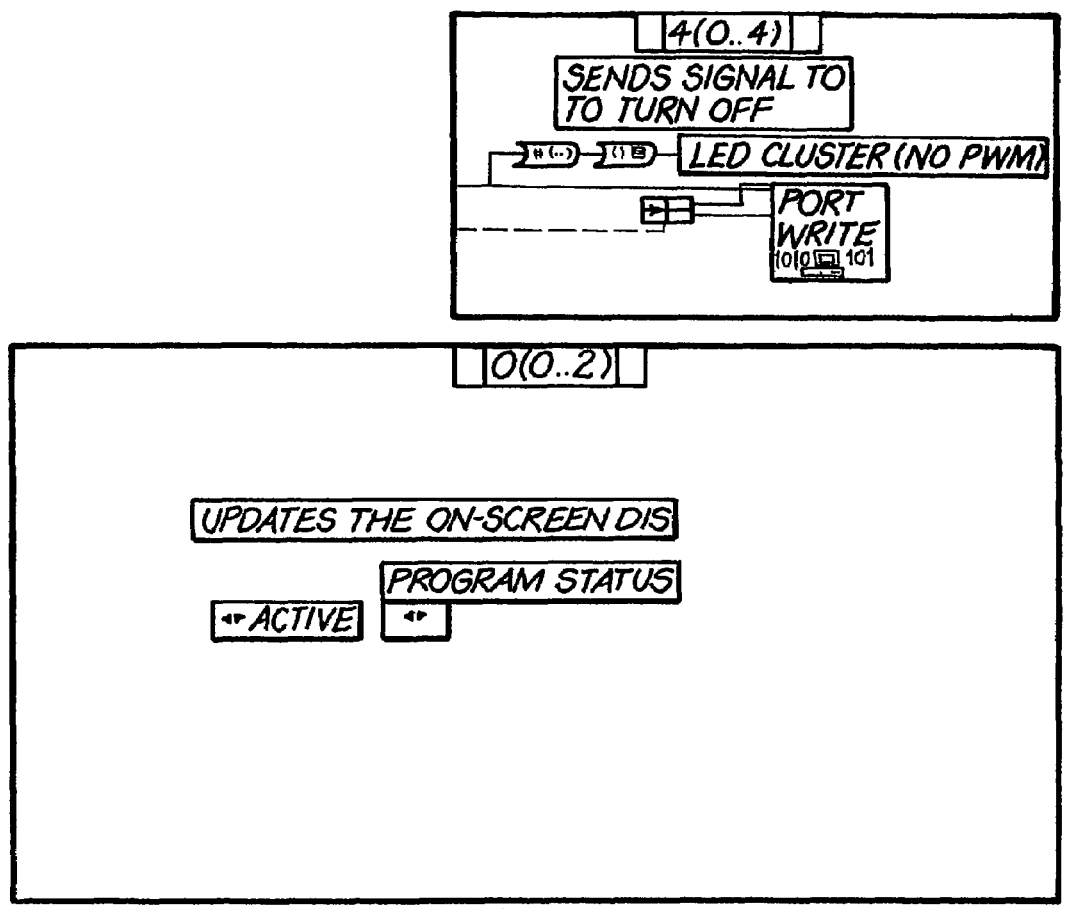
FIG. 24 is a further graphical programming code corresponding to the front panel of FIG. 22.
Figure 24:

FIG. 11 provides an illustration of a basic circuit layout of the operating means 85 of one preferred embodiment. In the figure, "DAQ" stands for "data acquisition" and "DIO" stands for "input/output channels", and will be used for data and control communication. The term "muscle wires" has been used to refer to the actuator 30.

FIGS. 12-24 illustrate front panels or user interfaces for various embodiments of the invention programmed to cause movement of a patient's joint, along with the corresponding graphical programming code for those front panels.

Further preferred embodiments comprise systems suitable for CPM therapy. Three different systems are described, named TAM, TAM-SAM and TENDON systems. The common novel features for the three are:

They are capable of working on individual fingers and individual joints in the hand. This is important in the treatment of isolated joint problems where it is desirable to immobilize other joints.

They are capable of sensing finger and joint position as well as the forces exerted on and by the fingers The passive finger movements can be better controlled with the provision of feedback of force and position information Adjustable safety force limits may be easily set by programming the device's electronic controller.

The CPM may be used as an automatic adjustable splint. Various combinations of finger and joint positions may be locked into place to maintain position and allow different types of hand therapy not previously possible with prior art.

A logger in the software can trace day to day improvements by tracking the Range of Motion (ROM) as well as the stiffness of the joints. This information may be downloaded to a PC for printing and analysis.

All 3 CPM systems are lightweight and provide unobstructed movement by leaving the palm side of the fingers free, this being supportive of effective hand grasp. The significance for this is that the CPM function may be modified to perform hand grasp and release (suitable for people with cervical spinal cord injury).

The individual features of each of the systems are detailed as follows:

CPM 1—TAM System

The TAM (Telescopically Activated Modular) System is made from individual modular actuator arms placed above each finger joint. Each module passively moves one joint when connected to its corresponding actuator cable. The uniquely novel features of the system include:

The system may be modified to act on just one finger joint, or it may be interconnected to act on all joints in the hand The isolated modules may be attached to plasters and bandages surrounding the joints.

The TAM works from the back of the hand leaving the sides and the front of the hand unobstructed.

CPM 2—TAM-SAM System

The TAM-SAM (Telescopically Activated Modular-Side Activated Modular) system is made from combined modular actuator arms placed on the sides of each finger. Each module passively moves the joints of a single finger when connected to its corresponding actuator cable. The following are the uniquely novel features of the system:

The system may be modified to act on a single joint only, leaving the other joints and fingers free, splinted or undertaking different CPM therapy This system is more compact and less conspicuous than the TAM, therefore it is cosmetically more appealing for long term use. It is also more rigid which improves the efficiency of the force and movement transmission by the actuator.

CPM 3—TENDON System

The TENDON system is a glove with embedded actuator cables arranged to function as tendons do in the human hand. The following are the uniquely novel features of the system:

This is the most compact unobstructive hand CPM of the three described. All passive movements are conducted via the cables within the glove.

The device is very easy to put on or take off.

The glove end of the device is detachable and may be washed or replaced without damaging the control modules powering the glove.

The natural pressure within the glove may help alleviate conditions such as oedema The glove is cosmetically appealing in comparison to prior art, making it suitable for long term and daily use.

Actuators and Feedback Sensors for Use within the CPM Device

In order to produce passive movement, a source of mechanical power is required. In most prior art, this is achieved by using rotational DC motors, implementing slow yet powerful movement though connections to gear boxes or worm drives. In the present technology, passive movement is achieved by the use of an actuating material that contracts in response to a stimulus. The actuator material may include any combination of the following:

Shape Memory Alloys (SMA), e.g. nitinol. This type of alloy contracts by about 4% when heated to a particular temperature. Heating may be effected using an electrical current.

Polypyrrole, Electro-Active Polymers (EAP), carbon nanotubes, Ionic Polymer Metal Composites (IPMC), Polyacrylonitrile (PAN). These actuators are activated by applied electrical charges and currents and are more efficient than the SMA, although typically not as powerful.

The actuating material is integrated within specifically designed actuator devices and feedback sensors, these being the Force-Position Transducer, M.A.L.C.A, L.U.I.S.A and B.I.R.A, described below.

Force Position Transducer (FPT)

One of the novel features of the CPM systems of the present invention is the force-position transducer capabilities. Each actuator has its own embedded miniaturized FPT, which is able to monitor the amount of force exerted by the transducer, as well as on the transducer by the finger. It can also monitor the position of the actuator cable and, hence of the finger. The FTP units should be calibrated before use. The novel feature of the FPT is that it uses very simple components including light emitting diodes (LEDs), a phototransistor and a spring to sense both position and force.

M.A.L.C.A (Multi-Armed Large Contraction Actuator)

The MALCA is concerned with achieving a greater overall contraction of material when the actuator is operated. This actuator uses the shape memory alloy (SMA) but may be modified for use with other material such as intelligent polymers. Novel features of this actuator include:

Increase of the actuation capabilities of the Nitinol SMA from 4% to much larger values (experimentally up to 15% but more is possible)

The ability to increase the overall contraction by increasing the number of layered actuation arms.

L.U.I.S.A (Linear Unidirectional Incremental Sequential Actuator)

LUISA utilizes two or more segments of actuator material to produce a stronger and longer linear movement than possible with the actuator material alone. This linear actuator is based on the Nitinol SMA but may be adapted to work with polymer-based or other contractile actuator material.

The novel features of this actuator include:

Long actuation distances (theoretically unlimited) are possible using this actuator.

The actuator shaft may be capable of exerting forces equal to the original strength of the contractile material but at a much greater distance than the material's natural contraction limit.

When the actuator is not powered, it automatically releases the shaft which may then move passively (e.g. by a spring or by antagonist actuation) to its original position In addition to the two required contracting wires, more wire units may be added to increase strength or smoothness of the actuation B.I.R.A (Bi-directional Incremental Rotary Actuator)

This actuator uses similar mechanism to the LUISA in order to turn a circular gear. The novel features of this actuator are equivalent to the above with the exception of the following:

Rotary motion is provided that may turn indefinitely.

The different systems are described below.

The CPM Systems

The CPM systems are made from the following components:

Mechanical assembly connecting to the fingers and joints. This includes mechanical safety limiting devices (force and position)

Actuators connecting to the mechanical assembly

Control system consisting of a user interface and an internal CPU containing the control software. Software controlled safety limiting devices are handled here.

Figure 26:
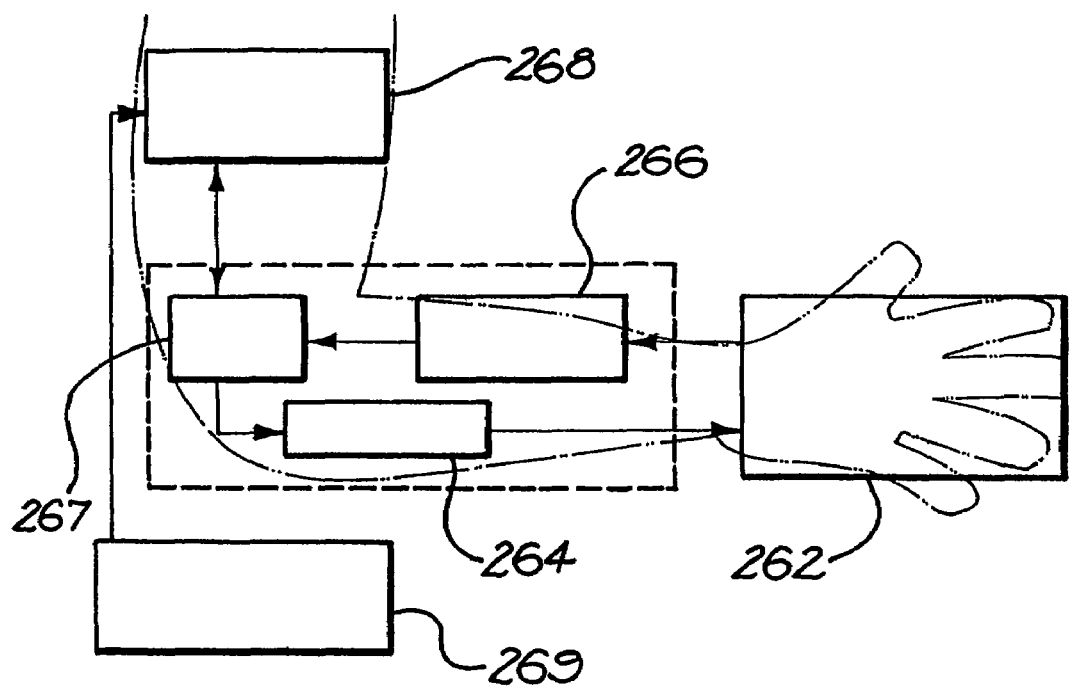
FIG. 26 is a diagrammatic representation of a telescopically activated modular (TAM) system showing the major components of the system.

Force and position transducers connecting to the mechanical assembly feeding back into the CPU as part of the control system Power Supply CPM 1—TAM System The TAM (Telescopic Activated Modular) system is designed to move individual joints of the hand independently and is shown diagrammatically in FIG. 26. It is composed of separate joint modules 262 connected to dedicated actuators 264 and feedback units 266 housed on the forearm. Actuators 264 and feedback units 266 are connected to CPU 267, which is in turn connected to a user interface 268 powered by power supply 269. A total of 30 units can be made available for the whole hand but the system can be operated by as little as one unit. Each module is also telescopically activated. Telescopic activation is a fundamental aspect of the system because it allows the actuation cables to reach the joints without being strained by the movement of other joints.

The joint units 262 are placed on the back of the hand. Each unit consists of a base attached to a finger segment with an activation arm extending out to the consecutive unit base (attached to the previous segment). These are shown in FIGS. 27 to 29.

Figure 27:
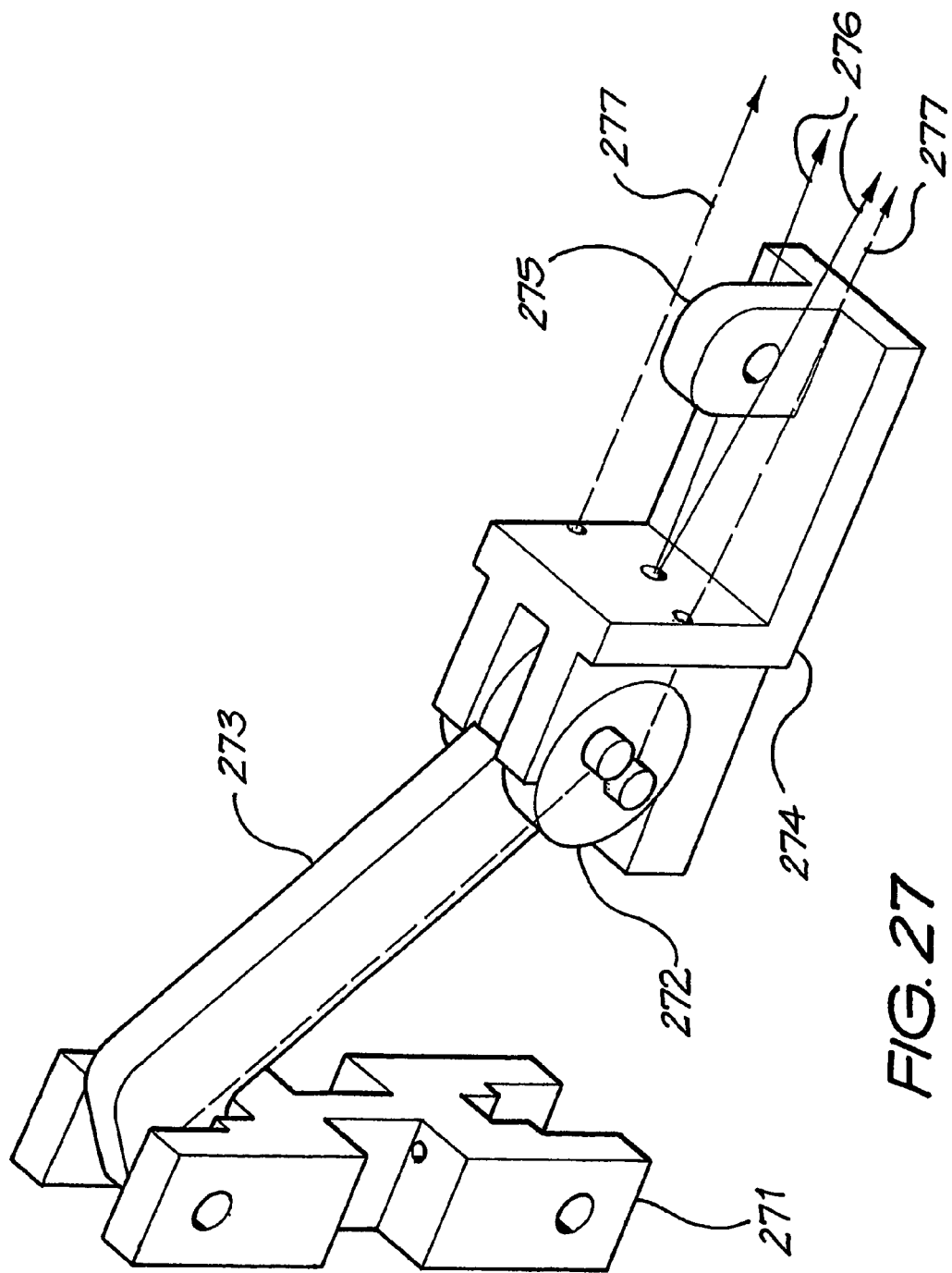
FIG. 27 is a diagram of a single joint activation unit of a TAM system such as is shown in FIG. 26.

In FIG. 27, H-arm 271 is connected to activation joint 272 by midarm 273. Activation joint 272 is mounted in base 274, which is fitted with attachment point 275 to connect to the H-arm of the next unit if needed. Activation cables 276 are connected to the active joint, one being for agonist movement and the other being for antagonist movement. Activation cables 277 extend through the TAM unit to the next consecutive TAM unit. In operation, activation of cables 276 causes H-arm 271 to move relative to base 274, leading to either flexing or extension of the joint to which they are attached.

Figure 28:
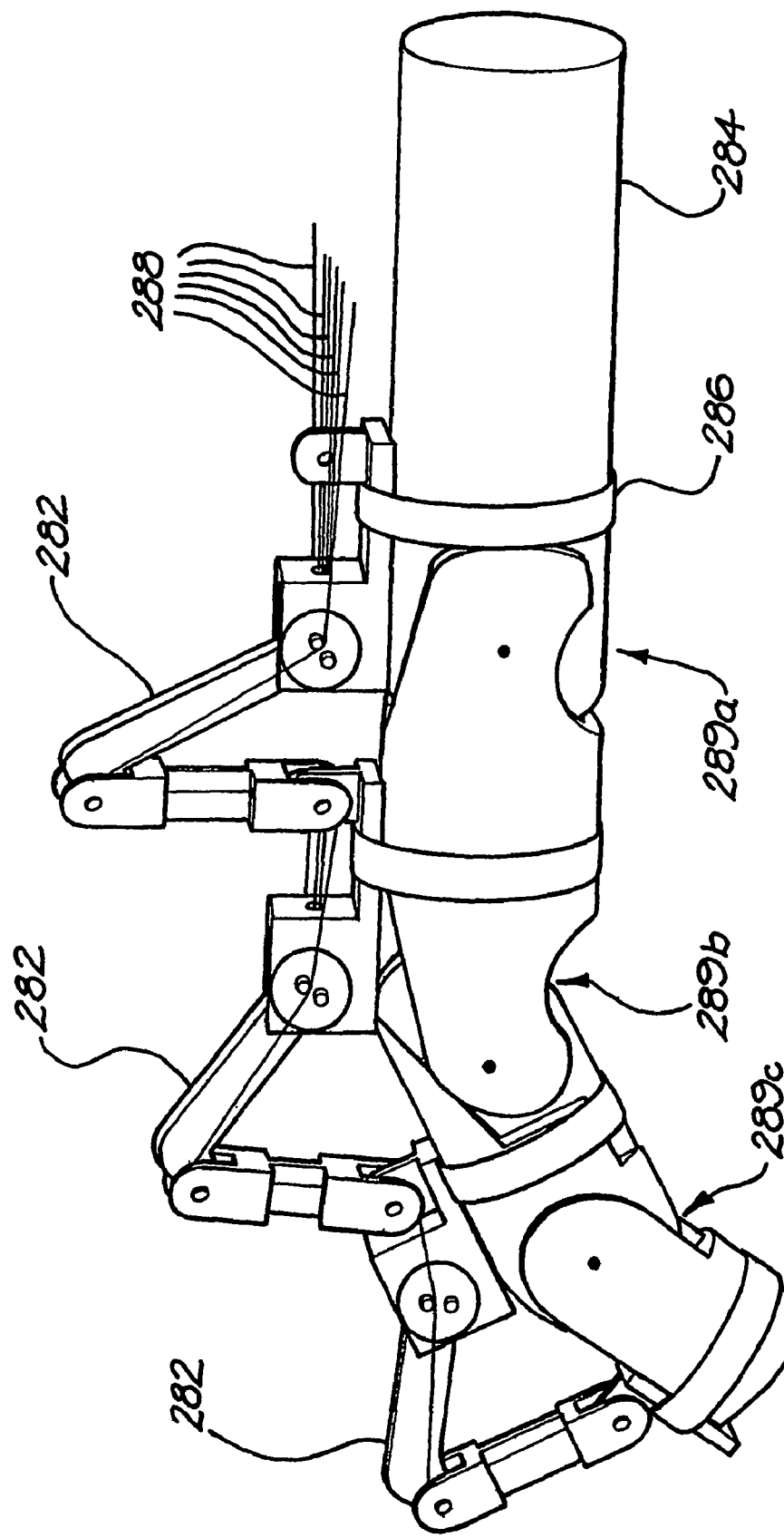
FIG. 28 is an illustration of 3 TAM units attached to a single finger in order to facilitate complex movement of the finger.

FIG. 28 shows three TAM units 282 attached to a finger 284. Attachment of units 282 to finger 284 is by means of attachment 286. Activation cables 288 extend from the actuators in order to promote movement of units 282. In this diagram, TAM units are attached to metacarpophalangeal joint ICP) 289a, proximal interphalangeal joint (PIP) 289b and distal interphalangeal joint (DIP) 289c.

Figure 29:
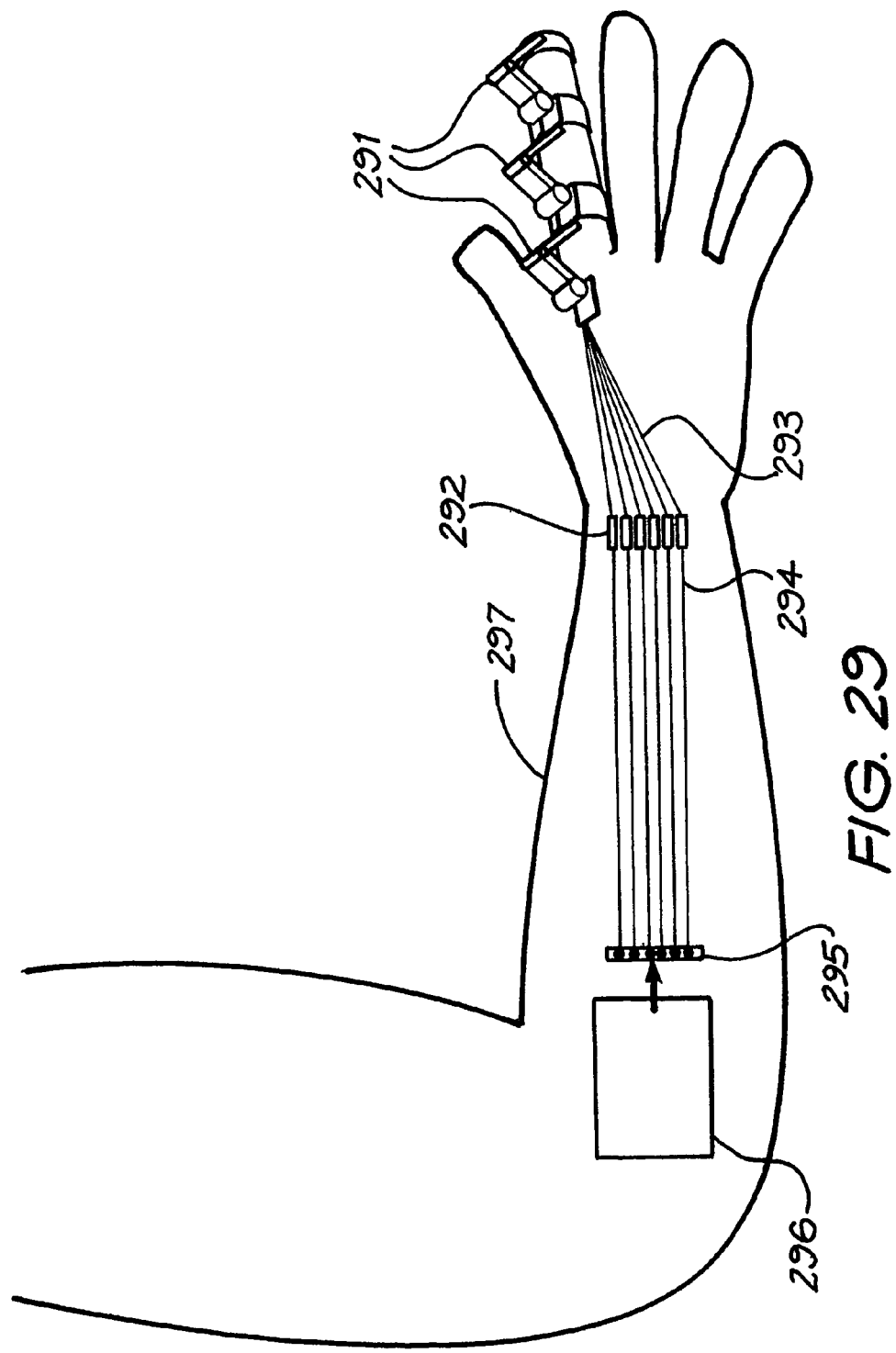
FIG. 29 is a diagram showing the connection of an actuator to activation cables via sensor blocks.

FIG. 29 shows the connection of the actuators to the activation cables. TAM units 291 (as shown in detail in FIG. 27) are connected to force-position sensors 292 by activation cables 293. Actuators 294 connect sensors 292 to connector block 295, which is electrically connected to the control CPU unit 296. Control CPU unit 296 and the housing for the actuators (not shown) are worn on the patient's forearm 297.

In cases where more than one finger on the hand has TAM units attached to it, multiple layers of actuators and sensors would be used. In operation, TAM units 291 facilitate movement of the patients joint. Control signals for that facilitation originate from CPU unit 296, which controls actuators 294, which in turn cause movement in TAM units 292 via activation cables 293. Sensors 292 provide CPU unit 296 with information concerning the operation of TAM units 292, so that CPU unit 296 can provide appropriate control signals.

The TAM has the advantage of keeping the palmar and lateral sides of the fingers free of components.

CPM 2—TAM-SAM system

Figure 30:
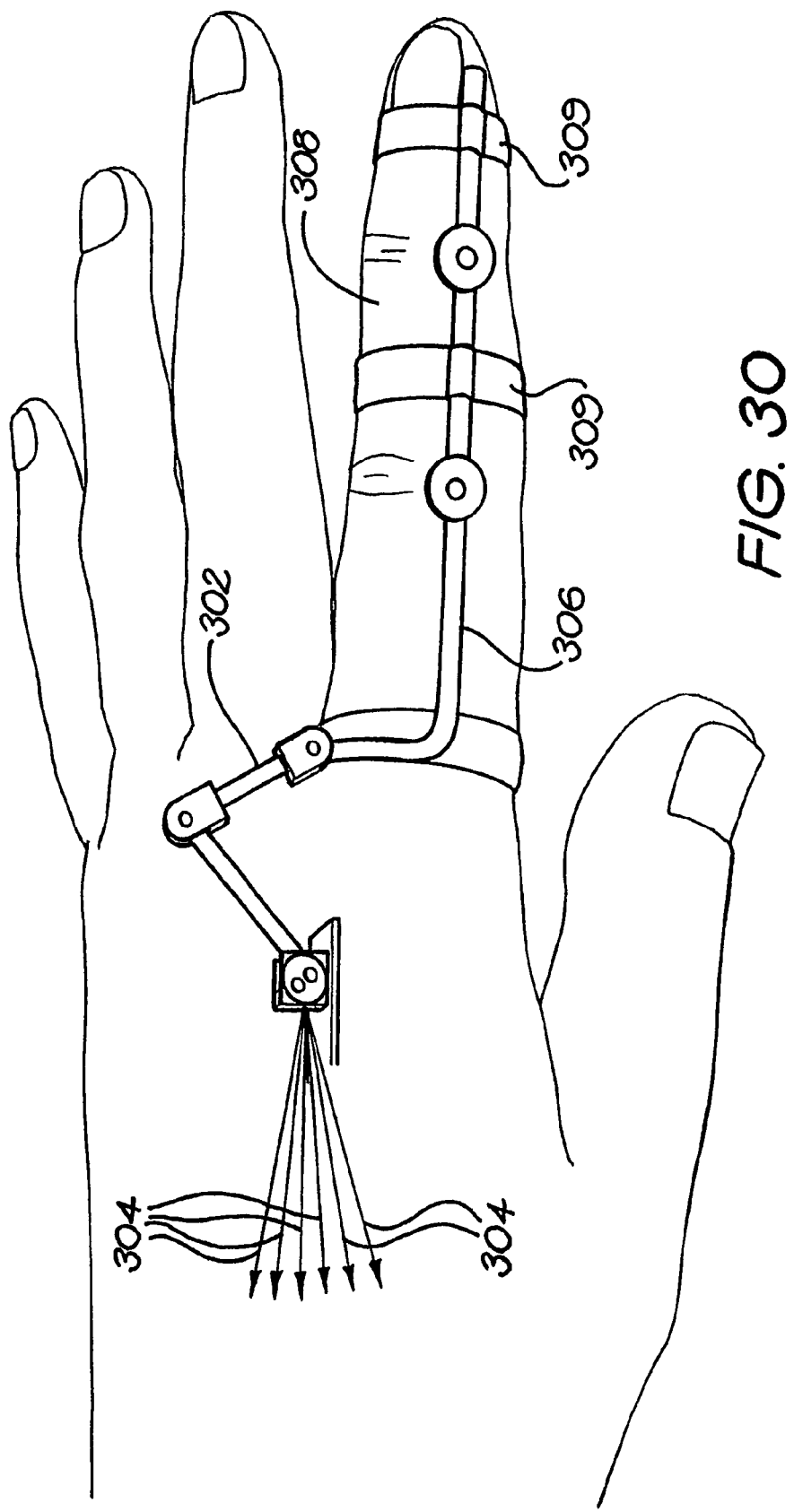
FIG. 30 is an illustration of a telescopically activated modular side activated modular (TAM-SAM) system.

This system combines aspects of the TAM system. Each finger is allocated a TAM unit for the MCP joint, connected to SAM activation arms attached to the sides of the fingers. The principal functional difference between this system and the TAM is seen at the activation end, attached to the fingers. By attaching to the sides of the fingers, this design avoids the slightly more bulky nature of the TAM. FIG. 30 shows the basic activation unit of TAM-SAM for one finger. In FIG. 30, TAM unit 302 is connected to activation cables 304. It is also connected to SAM activation arms 306 on finger 308, arms 306 being attached to finger 308 by attachments 309. The same unit may be replicated for the other fingers and the thumb. The activation cables extend to the same sensor block and actuation block used in a TAM system such as is shown in FIG. 29. In operation, signals from a CPU unit (not shown) cause actuators (not shown) to initiate movement in the patient's hand joints via activation cables 304, which act on activation arms 306 via a TAM unit mounted on the back of the hand.

CPM 3—TENDON System

Figure 31:
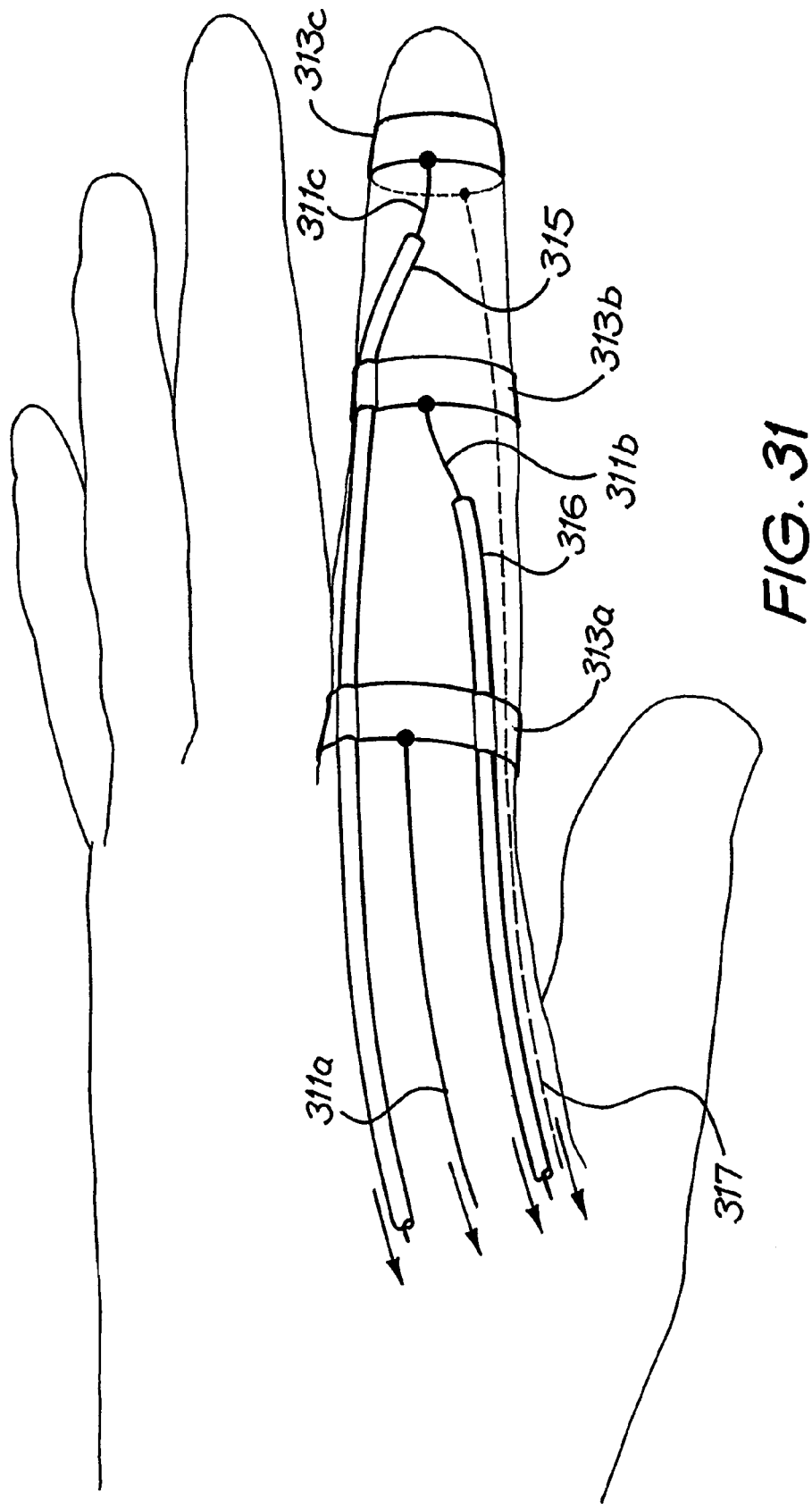
FIG. 31 is an illustration of a TENDON system, showing embedded actuator cables.

This system is based on an easy to put on glove that has activation cables woven through its fabrics to reach the segments of the finger, and is shown in FIG. 31. Extensor cables 311a, 311b and 311c come via the back of the fingers and connect to interwoven bands 313a, 313b and 313c which are more rigid than the glove fabric which secures the cables to the finger segment. There are 3 extensor cables per finger. PIP and DIP extensor cables 311b and 311c respectively are partially carried to their segments through interwoven thin Teflon tubes 315 and 316, also known as telescopic tubes. There is only one flexor cable 317 per finger, carried via the palm side of each finger and securing only to rigid interwoven band 313c at the tip of the finger. CPU and actuators (not shown) cause retraction of one or more of cables 311a, 311b, 311c and the flexor cable in order to facilitate appropriate movements of the finger joints. FIG. 31 illustrates only the mechanism for a single finger, however a glove may have corresponding sets of cables, attachments etc. in some or all of the other fingers (including the thumb) for facilitation of movement of some or all of the joints in those other fingers.

Force-Position Transducer

Figure 32:
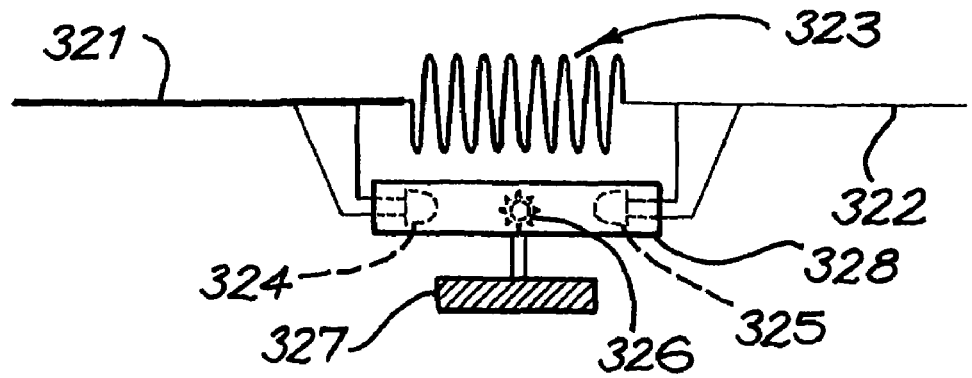
FIG. 32 is a diagrammatic representation of a force position transducer (FPT) showing the various components of the transducer.

This transducer, shown diagrammatically in FIG. 32, is made from the following components:

Actuator cable 321, being the cable that is directly connected to the actuator

Activation cable 322, being the cable that is connected to the mechanical components that passively move the fingers.

FPT Spring 323. This spring connects cables 321 and 322.

2 Phototransistors 324 and 325.

1 LED transmitter 326, atttached to stationary anchor point 327.

Phototransistors 324 and 325, and LED transmitter 326 are located within opaque tube 328.

Figure 33:
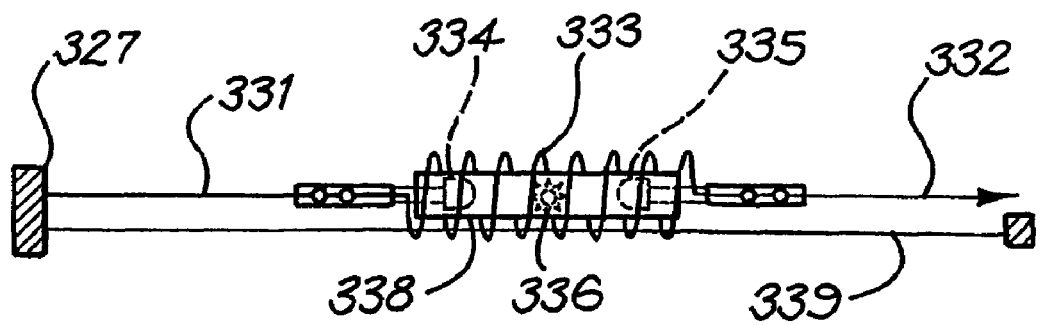
FIG. 33 is a diagrammatic representation of an alternative arrangement to a FPT to that shown in FIG. 32.

The purpose of the FTP transducer is to provide a method of measuring both the position of the segment being moved and the force being applied on it. This transducer is a component of each independent joint actuator in the CPM system. The position information may be used for control of speed and range of movement. The force information may be used to control the applied force on the fingers as well as to provide a safety mechanism so that the maximum force limit cannot be exceeded. An alternate setup of these components is shown in FIG. 33, where opaque tube 338 is placed inside the spring and stabilized using the support cable 339 attached to anchor point 337. Thus actuator cable 331 and activation cable 332 are connected to spring 333. Phototransistors 334 and 335 and LED 336 are located inside opaque tube 338. LED 336 and opaque tube 338 are held stationary by attachment to support cable 339, whereas phototransistors 334 and 335 are free to move relative to LED 336.

M.A.L.C.A (Actuator)

Figure 34:
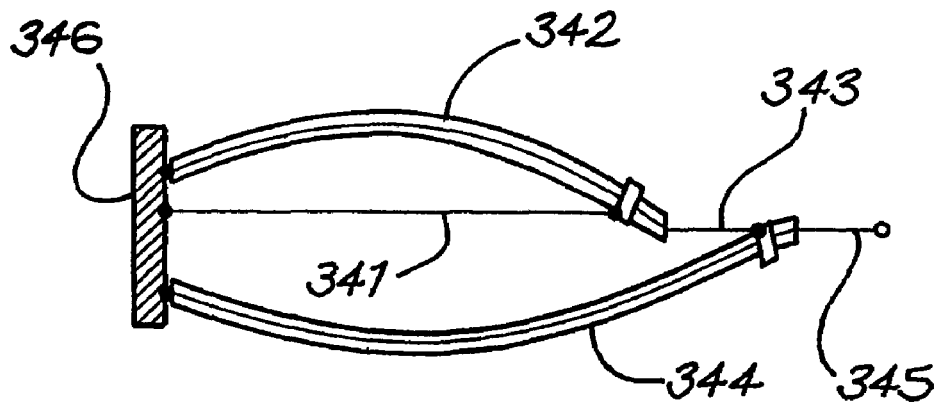
FIG. 34 is a diagrammatic representation of a multi-armed large contraction actuator (MALCA), showing the component parts of the actuator.

This actuator, shown diagrammatically in FIG. 34, may use any type of contractile material, however in this description nitinol wire (shape memory alloy) is used. The wires are configured in a manner that increases the overall contraction of the system. The actuator may have several branches of nitinol wire (N.W). The first branch, single straight nitinol wire 341, is directly attached to the end of teflon tube 342 containing second nitinol wire 343. Wire 343 coming out of this teflon tube is subsequently attached to the end of the next teflon tube 344 containing the third branch 345. Additional branches may be connected in this way. Thus all branches and tubes have one end anchored to point of reference 346 and the free end attached to other wires.

L.U.I.S.A (Actuator)

Figure 35:
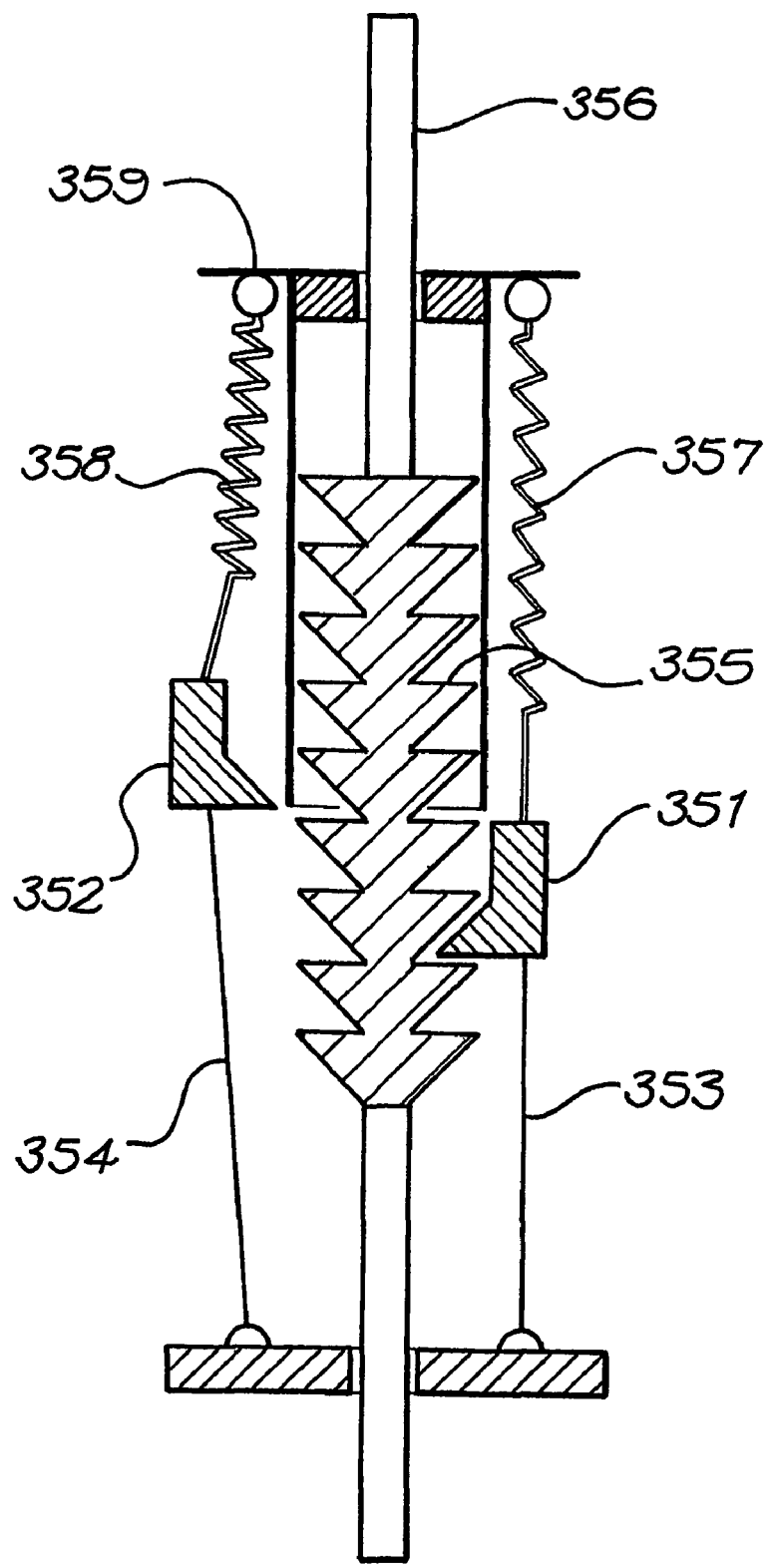
FIG. 35 is a diagrammatic representation of a linear unidirectional incremental sequential actuator (LUISA) showing the principal component parts.
Figure 36:
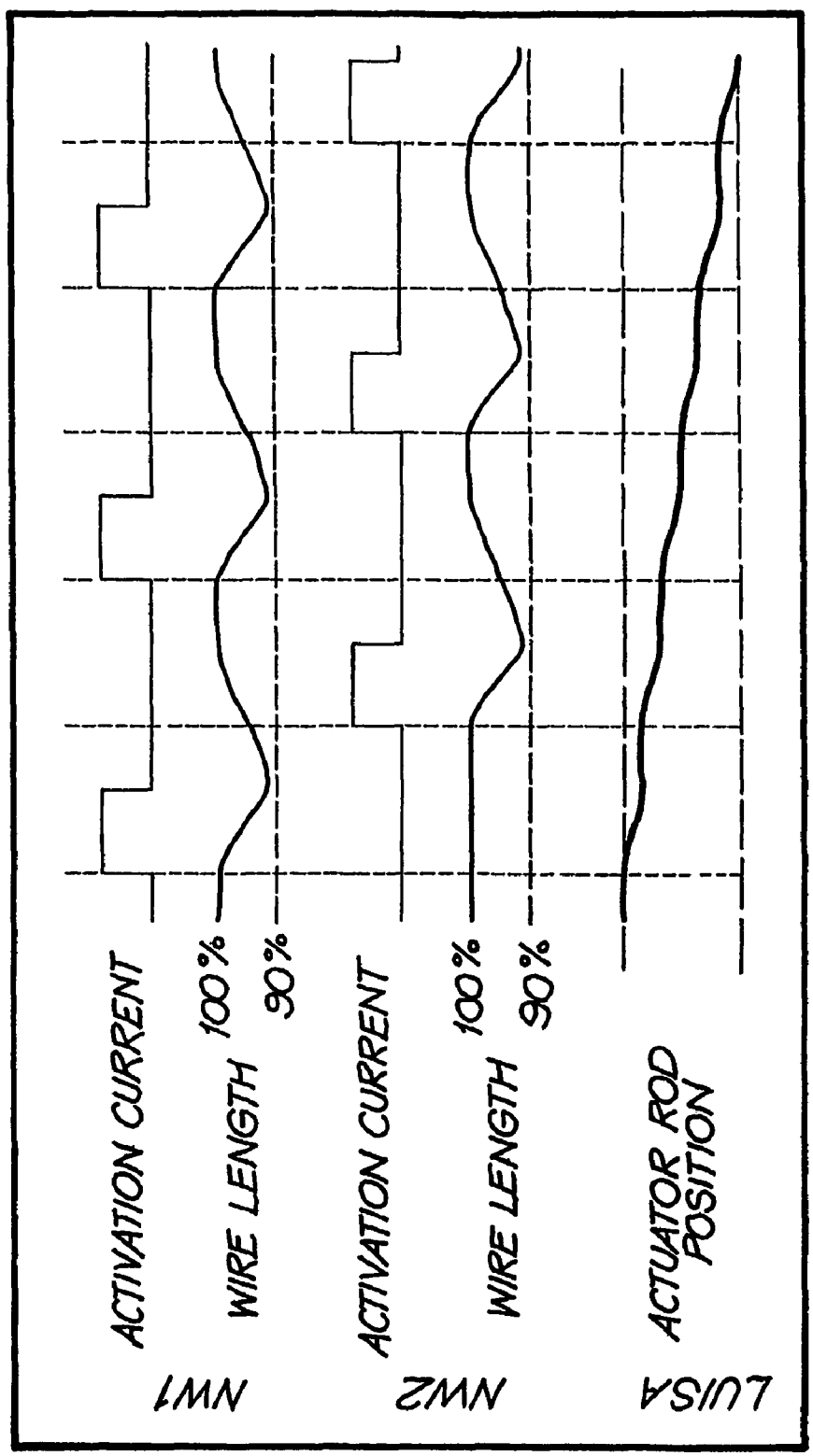
FIG. 36 is a graphical representation of a sequential powering method.

The components of this system are depicted in FIG. 35. The actuator may be based on any type of actuator material. However nitinol wire is used to describe this design. The actuator uses a minimum of 2 hooks 351 and 352 attached to nitinol actuator wires 353 and 354 respectively, which pull down on teeth 355 of actuator rod 356 every time they are activated. Hooks 351 and 352 are also connected to springs 357 and 358 respectively, that bring them back up when wires 353 and 354 are inactive. A sequential powering method illustrated graphically in FIG. 36 ensures that actuator rod 356 is continuously moving. The benefit of this actuator is that even though the activated nitinol wire contracts a small amount each time, the final actuation length is much greater and the original power of the nitinol wire is retained. The trade off for this greater length is contraction time. The longer the contraction length, the longer it takes to fully implement it. When the nitinol wires 353 and 354 are not powered, release shield 359 mechanically releases hooks 351 and 352, in effect freeing actuator rod 356 to return to its original position. Additional nitinol wire arms may be incorporated around actuator rod 356 to increase smoothness and/or strength of movement.

B.I.R.A (Actuator)

Figure 37A:
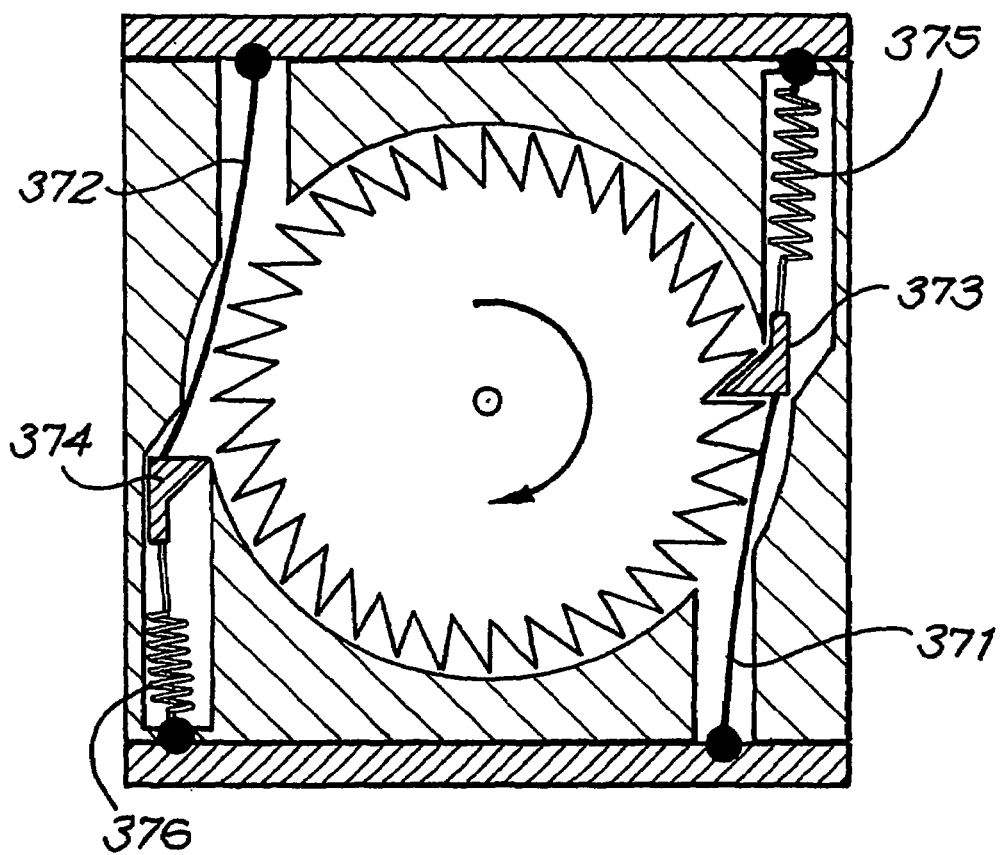
FIG. 37a is a diagrammatic representation of an a bidirectional incremental rotary actuator (BIRA).
Figure 37B:
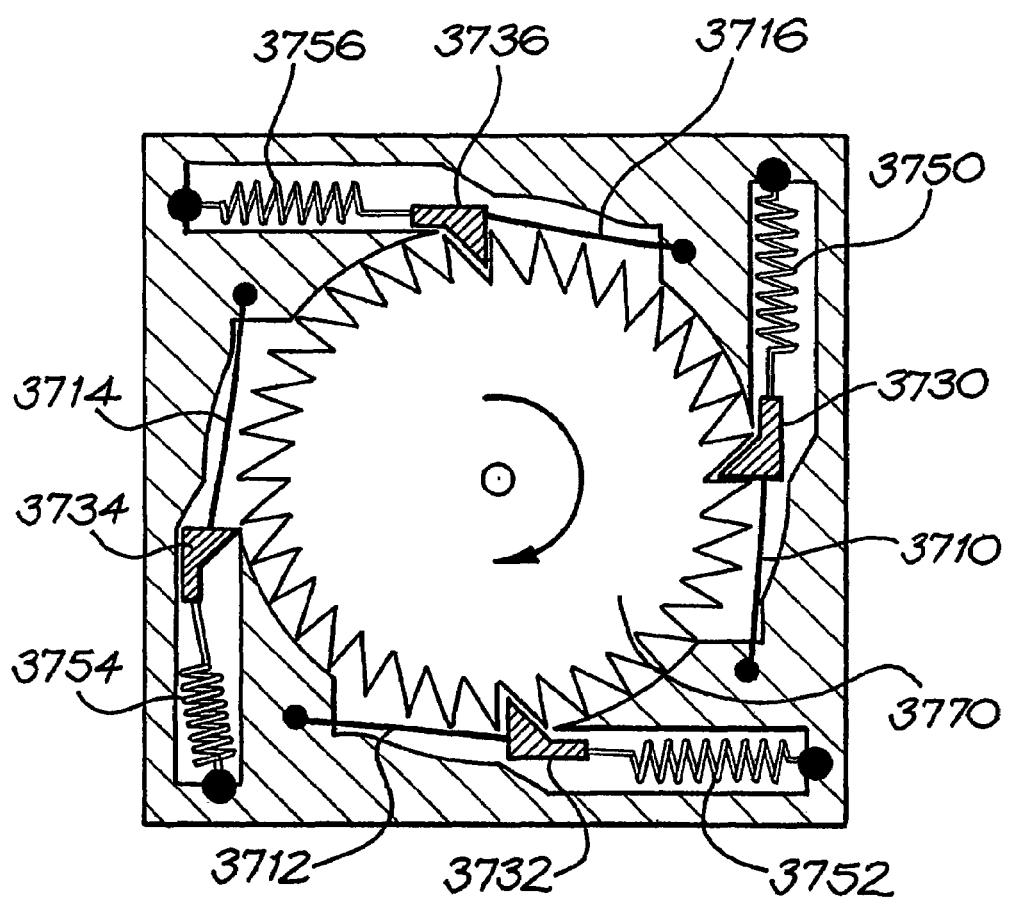
FIG. 37b is a diagrammatic representation of a modified BIRA showing additional springs to improve performance.

This actuator is shown in FIG. 37a. As above, this actuator may be based on any type of actuator material, although nitinol is used in this description. BIPA also uses the same strategy as the LUISA for increasing actuation length using 2 o nitinol wire arms 371 and 372 attached to hooks 373 and 374 respectively which are in turn attached to springs 375 and 376 respectively. The principal difference is that the actuator teeth are around rotary disk 377, making the actuation rotational and indefinite. As long as hooks 375 and 376 are pulled and released sequentially, disk 377 will rotate. The additional advantage of this actuator is that the torque produced by the actuator may be varied by changing the diameter of disk 377. This may be used as a mechanical advantage to trade off force for speed. FIG. 37*b* illustrates an alternative configuration of the BIRA actuator shown in FIG. 37*a*, whereby additional actuator wires, springs and hooks are included in order to improve smoothness and increase strength. Thus in FIG. 37*b*, wires 3710, 3712, 3714 and 3716 are attached to hooks 3730, 3732, 3734 and 3736 respectively which are in turn attached to springs 3750, 3752, 3754 and 3756 respectively. As long as hooks 3730, 3732, 3734 and 3736 are pulled and released sequentially, disk 3770 will rotate.

Other Considerations

Control of CPM devices. The CPM devices may be controlled using software embedded in a portable control unit. This may be in the form of a PDA (e.g. a PalmPilot™) device with hardware interface. The particular CPM activities may be programmed by the therapist using the software interface available.

Safetyfeatures. Safety considerations include correct anatomical movement and force and position limits. Correct anatomical movement has been considered in the physical design of the various CPM components. As for safety limits regarding force and position, these may be set in two ways combined for additional protection: physical limits in the form of adjustable mechanical stoppers and safety force releases (mechanical fuses) as well as software set limits controlled via the feedback information.

Other joints in the body. The designs presented in this application may be modified to suit almost all joints in the body. In particular a single joint unit can be created for joints such as the wrist, the elbow or the knee.

Cooling of wires. The nitinol actuators discussed in these designs may dissipate a significant amount of heat. The cooling strategy considered for this effect is thermo-electric cooling, based on the Peltier effect.

Operation of the systems is described below.

TAM CPM

Figure 38:
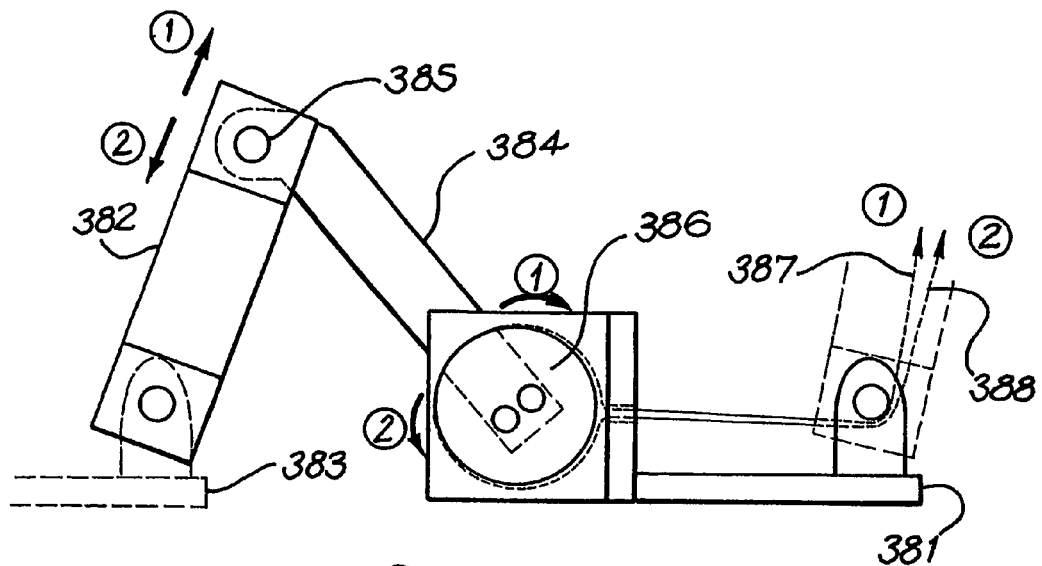
FIG. 38 is a diagrammatic representation of a TAM actuation unit showing the principal components of the mechanism.
Figure 39:
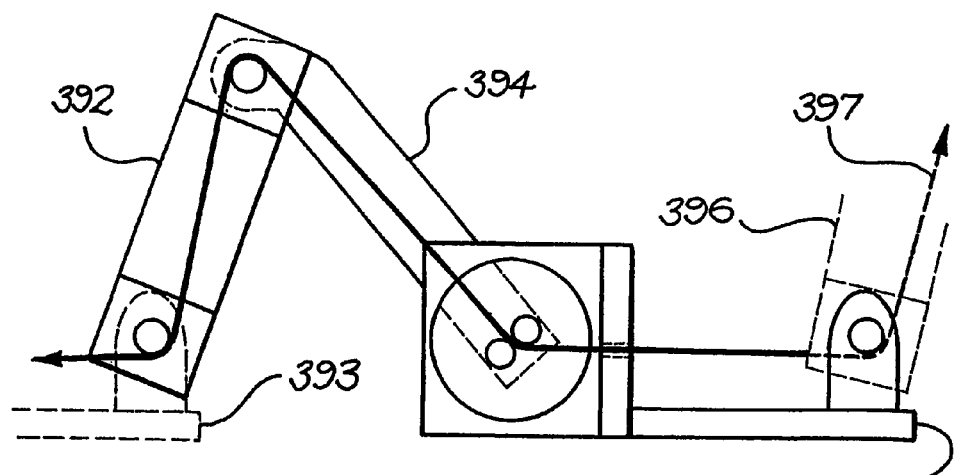
FIG. 39 is a diagrammatic representation of a TAM actuation unit illustrating the means for bringing activation cables to their destinations.

FIGS. 27, 38 and 39 depict the basic function of a single joint activation unit. With reference to FIG. 38, while base 381 is stabilized dorsally on finger segments (or the metacarpus in the case of the MCP joint), H-arm 382 is connected to another base 383 attached to the next distal segment. H-arm 382 exerts the required forces by pulling or pushing on this attachment. H-arm 382 in turn is connected to mid-lever 384 via a single is joint, 385. Mid-lever 384 is directed in a clockwise or anti-clockwise manner by the movement of activation joint 386. This activation joint is connected to two antagonist cables 387 and 388. These cables are brought to this joint via a system referred to as "telescopic". Telescopic activation is manifested by bringing cables through the centre (or very close to) of other joints in the system. This is done to minimize the interference of each cable with the movement of components in previous segments and vice versa. The result is that the cable may be pulled on by the actuator at one end, and the other end of the cable will theoretically exert the same force at the chosen segment regardless of the position of the joint in respect to one another. Thus pulling on cable 387 (the extension cable) causes H-arm 382 to rise and pull the next segment up, and pulling on cable 388 (the flexion cable, causes H-arm 382 to fall and push the next segment down. FIG. 39 illustrates the strategy used to bring activation cables to their destination. Thus, similar to FIG. 38, H-arm 392 is connected directly to base 393 of the next segment, and via mid-lever 394 to base 391. H-arm 396 belongs to the previous segment and is connected to base 391 Cable 397 comes through the centre of the joint of the previous segment. This minimises the torque creating effect of cable 397's tension on other independent joints.

Figure 40:
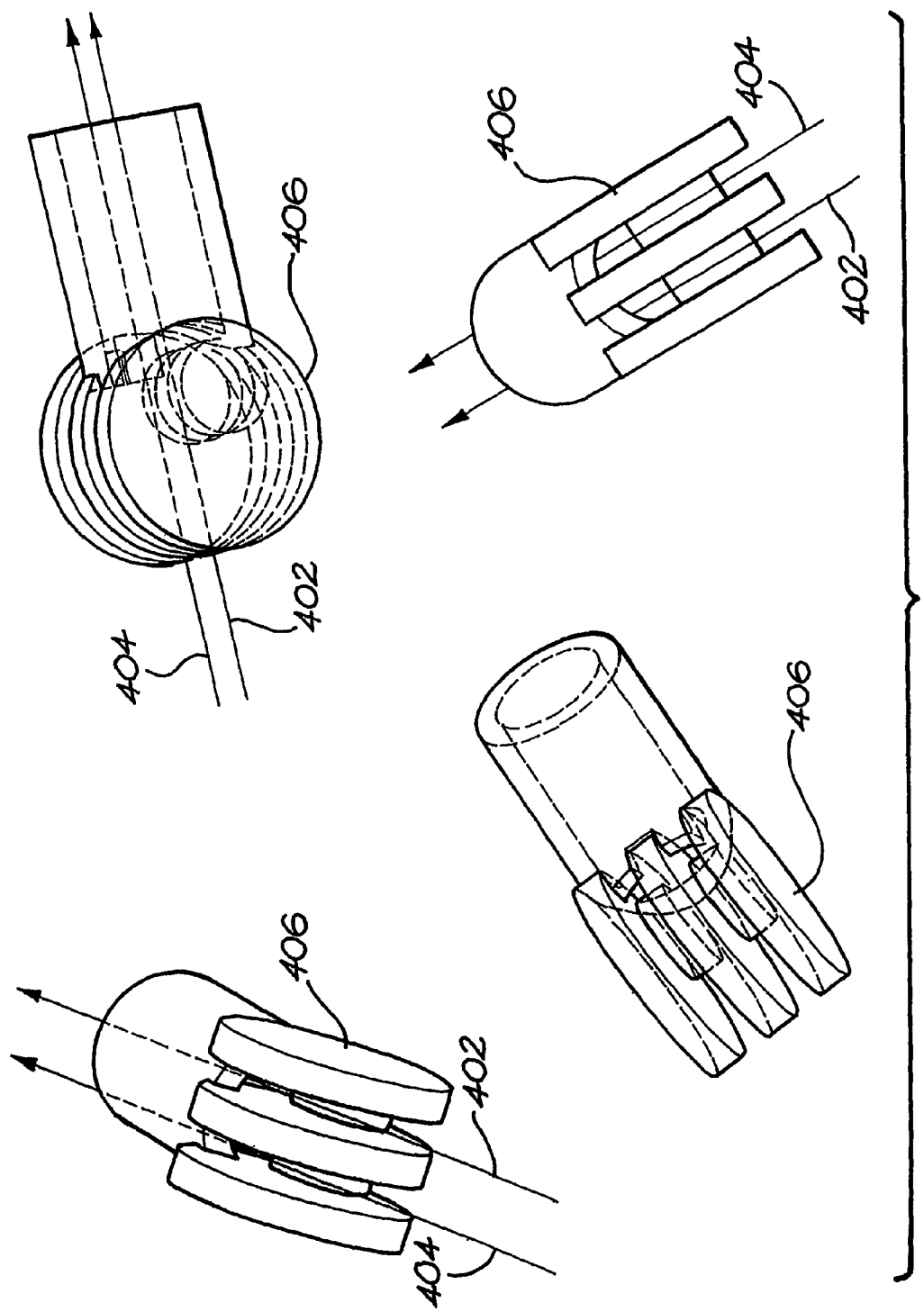
FIG. 40 is a diagrammatic representation of a gear from a SAM system.

TAM-SAM CPM This system also uses a telescopic actuation method similar to the TAM system. It is comprised of a single TAM unit used for the MCP joint followed by two SAM units for the PIP and DIP joints respectively. The SAM joint used a simple hollow cylindrical joint held in place by a hollow socket. The hollowness of the joints and sockets facilitate the travel of activation cable to the following joints. FIG. 40 shows a detailed view of the SAM joint, showing in particular the locations of cables 402 and 404 in SAM joint 406. The SAM is designed in such a way that cables of distal units can go through the center of the joint as to not exert any torque on proximal joints. This structure allows telescopic and independent activation of all joints. FIG. 40 further demonstrates the workings of a single TAM-SAM unit.

TENDON CPM

Figure 41:
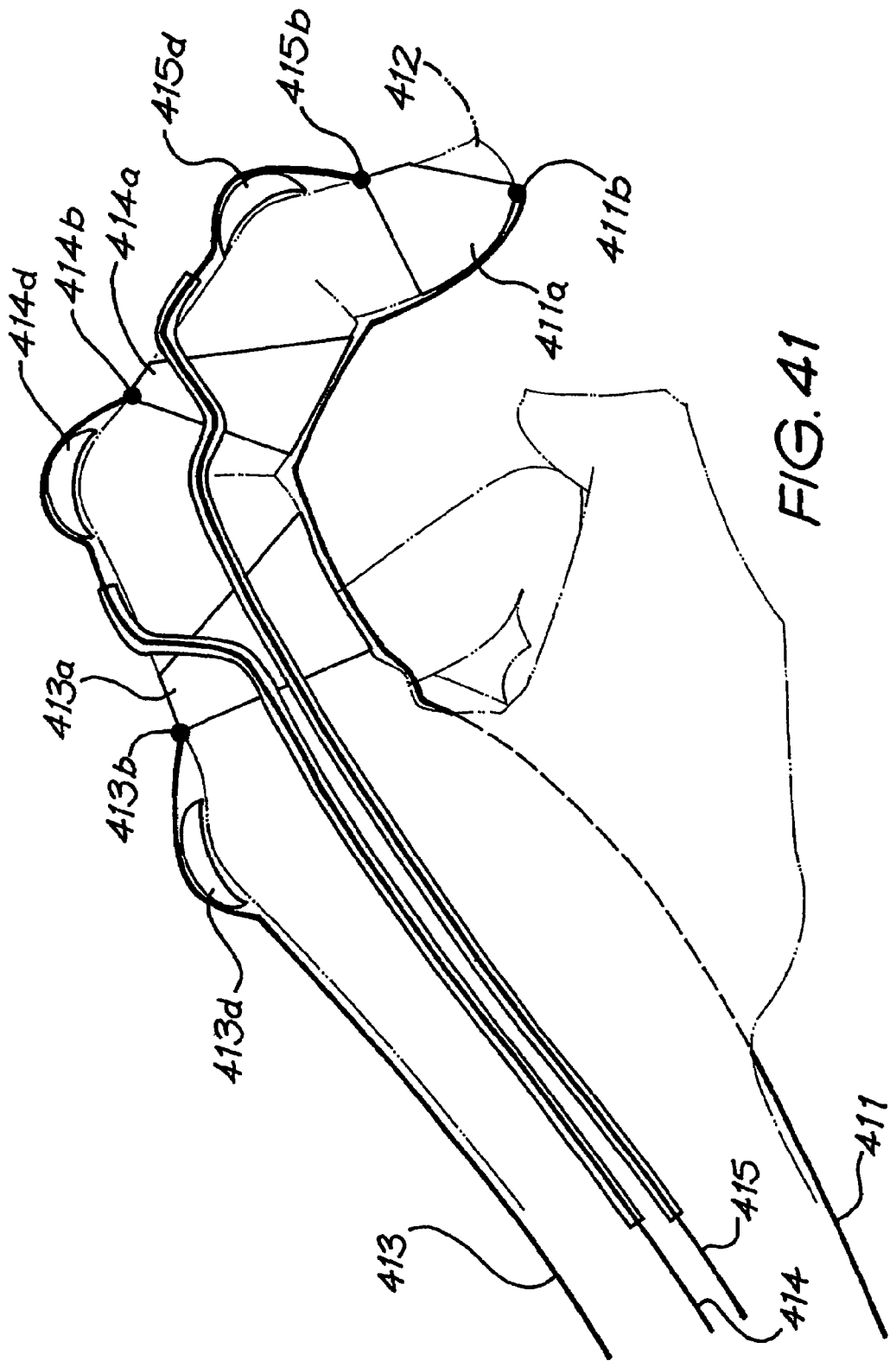
FIG. 41 is an illustration of a hand fitted with a TENDON glove showing the design of the glove.

Unlike the TAM and TAM-SAM designs, the TENDON system flexes at the joints of each finger using only a single flexor cable. This cable runs from the actuator through the glove (within the fabric of the glove) to a reinforced portion of the glove at the tip of the finger. Therefore activating this cable alone, flexes the entire finger into a curled position. The independent movement of the joints, however, is achieved by the telescopic activation of individual extensor cables. These cables are specific to their specified joint and their activation extends the phalanx to which they are connected. These connections are shown diagrammatically in FIG. 41 for a single finger in the TENDON glove. In FIG. 41, flexor cable 411 is connected to reinforced fabric 411*a* by connection 411*b*, located under finger 412. Similarly extensor cables 413, 414 and 415 are connected to reinforced fabrics 413*a*, 414*a* and 411*a* respectively by connections 413*b*, 414*b* and 415*b*. Cables 414 and 415 pass through teflon tubes 414*c* and 415*c* respectively. Plastic knuckles 413*d*, 414*d* and 415*d* are made of plastic, and are interwoven in to the glove. They are tough but flexible, providing additional mechanical advantage to extension cables 413, 414 and 415 respectively. The same connections may be carried out to all fingers including the thumb.

To flex all fingers and re-extend, first the flexor cable 411 is activated, followed by a pause after which the extensor cables 413, 414 and 415 are activated sequentially (e.g. MCP then PIP then DIP). If only a single joint is required to be flexed and re-extended then the following strategy is used: First the extensor cables for joints not requiring flexion are activated and held for the duration of the upcoming flexion. Then shortly after the flexor cable 411 is activated at a constant force. Thus the moments about the inactive joints are balanced and no movement occurs. However at the appointed joint, only flexion moment is present and this causes the appropriate movement at this joint. The same method may be used to independently activate any combination of joints in the hand. Furthermore, position feedback for all joints in the hand may be derived from the position of the respective extension cables which are absolute in relation to their corresponding joints.

Programmable Splinting in All Systems

This novel feature of all CPM systems described above can be achieved in two ways. Firstly any particular finger positioning can be achieved, provided that it is permitted by the physical constraints of the hand, by the use of the actuators within the system. The position feedback can guarantee the desired postures in the fingers. Maintaining these postures however will be energy consuming since the actuators would be required to continuously exert forces. Thus the second method which may be combined with the first is to provide a feature that allows mechanical locking of all the joints once the desired posture is reached. This may be done easily at the actuator end rather that at the joints themselves. Since the joints are directly connected to the strong activation cables, a press-lock may be activated near the wrist where all the cables are extending to the fingers. This lock may be activated manually, or another actuator may be dedicated to locking and unlocking this feature.

Force-Position Transducer

FIGS. 32 and 33 illustrate the individual components of the FPT. With reference to FIG. 32, these components work in such a way as to give information about the position of activation cable 322 and, hence, the joint angle. This is in addition to the position of actuator cable 321. A simple spring, 323, connects cables 321 and 322. Therefore the changing length of spring 323 may be derived from the position information of the two cables 321 and 322. The length of spring 323 directly relates to the amount of force being applied to it. This force value may be obtained using the formula $F=K \cdot L$, where K is the spring tension constant (known) and L is the length spring 323 has been extended by following the exertion of the tensile force.

Position measurement may be performed using a light emitting device such as an LED and a light sensing device such as a phototransistor. The principles behind this operation are based on the decreasing intensity of light with increasing distance given by the formula:

$I=C/(D+A)^2$, where I and D represent intensity and distance respectively and C and A are constants. The phototransistor has the ability to represent the received intensity of light by changing the voltage across it. This voltage is directly proportional to the intensity detected.

Figure 42:
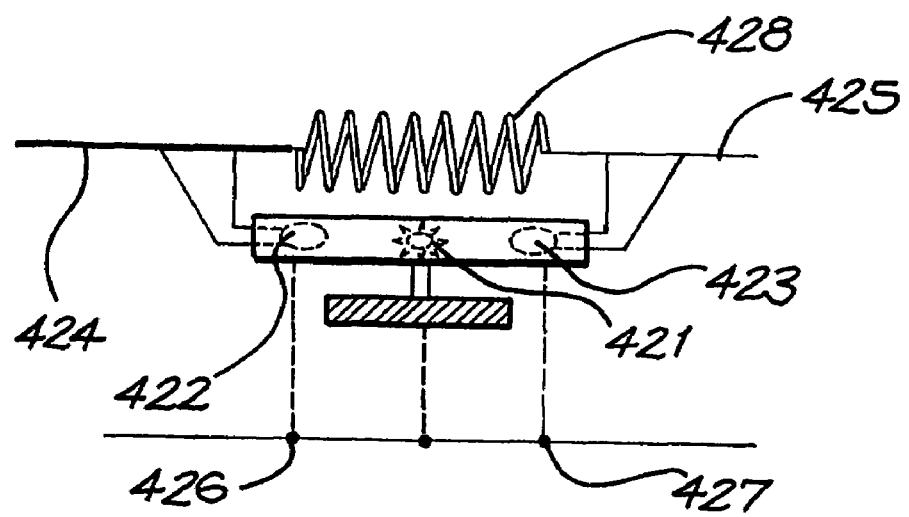
FIG. 42 is a diagrammatic representation of a force position transducer showing the variables used to determine position and force.

FIG. 42 shows how a single fixed emitter 421 and two floating receivers 422 and 423 attached to the actuator and activation cables 424 and 425 respectively may be used to obtain two position values P1 from position 426 and P2 from position 427. P1 is a direct value for the position of activation cable 425.

Force measurement. To derive force the following formula may be used: $F=K(L-L')$ where L is the length of spring 428 (L' is the original length) $F=K((P1-P1')-(P2-P2'))$

M.A.L.C.A

FIG. 34 illustrates the components of a MALCA unit. The fundamental principle of operation behind the large overall actuation length of the MALCA is the use of telescopic sub-actuators therein. Each telescopic actuator unit is comprised of a rigid frictionless tube such as a teflon tube with an actuator inside it (such as nitinol wire). The inner circumference of the tube remains constant even if the tube is bent to a degree. This allows us to bring the end of one actuator wire directly to the end of another independent to the movement of the latter.

Figure 43:
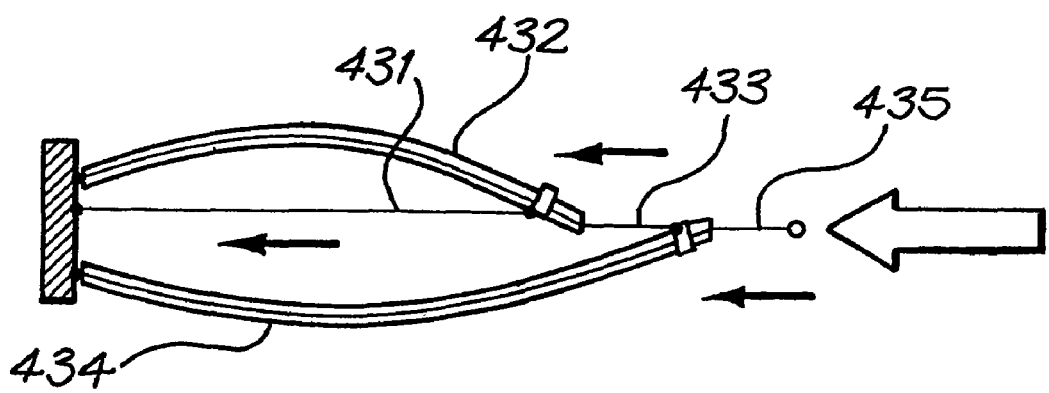
FIG. 43 is a diagrammatic representation of a MALCA showing the operation of the device.

FIG. 43 best demonstrates how this concept is used in the MALCA. Upon activation first wire 431 contracts by a certain amount. Wire 431 is connected to teflon tube 432 with another wire causing it to bend in the direction of contraction. Note that at this stage the tip of wire 433 maintains its distance to the tip of teflon tube 432 and hence is pulled left-wise also. Next wire 433 is also activated and this cause a further movement of the tip of this wire to the left (i.e. so far the total movement has been the contraction length of first wire 431 plus the contraction length of wire 433). The two previous contractions have both caused a pull on teflon tube 434 containing wire 435. Thus even before this wire has been activated it has already been pulled to the left. Finally the activation of wire 435 causes another movement. Hence the total movement of the whole actuator is roughly equal to the combined length of 3 wires. The same concept can be applied to as many as wires as required to increases the overall actuation length.

L.U.I.S.A

This is illustrated in FIG. 35. The main feature of this actuator is a long jagged cylinder 355 with a shaft 356 through it. The upper end of this shaft can be connected as the active end of the actuator. The internal mechanism of the LUISA however lies within the function of the two hooks 351 and 352 on either side of the jagged cylinder. Upon sequential activation (where one hook is activated, then relaxed while the other is activated and so on), each hook incrementally pulls down on one side of the cylinder by locking onto one of the actuator teeth. Sequential activation is further illustrated in FIG. 36. The hooks and teeth are fashioned in such a way that locking would only occur in one direction. In other words when the hooks are relaxed and go back to their original position they slip past the teeth of 355. One of the objectives of this design has been to provide a mechanism to release the hooks from the teeth when the actuator wires 353 and 354 (e.g. nitinol wires) are not being powered. This has been achieved by incorporating a component referred to as the release shield (359 in FIG. 35). This consists of a flat sheet situated at close proximity to the surface of the cylinder, which releases the hooks by forcing them to move away from the actuator teeth as they are pulled up by the spring. Additional hook-actuator wire units can be added to improve performance. For these additional units, coactive wires can increase the strength of the actuator whereas sequentially active units can increase the smoothness of the actuation. Since the activation is software driven, a number of combinations of activation patterns can be selected from to trade power for smoothness and speed and vice versa Oust like real muscles).

B.I.R.A

This is illustrated in FIG. 37a. This actuator works in a similar way to the LUISA. The difference being that instead of a jagged cylinder and shaft, the actuator component is a jagged rotary disk 377. The rotating shaft of this disk can be coupled with another disk with looped cable to provide tension or it could be coupled to other rotational levers or arms using gears. One advantage of this design is that by changing the diameter of inter-coupling gears and disks, rotational speed and strength can be modified. As may be seen in FIG. 37, a single jagged disk 377, at least 2 hooks 373 and 374 with associated springs 375 and 376 and nitinol wire 371 and 372 (or other contracting material) may be housed together in a solid structure (acting as container of the components as well as the release shield for the hooks). The hooks contract and release as in the LUISA actuator following sequential activation. Additional hooks may be added around the disk to modify performance to desired smoothness, speed and strength (see FIG. 37b).

Figure 44:
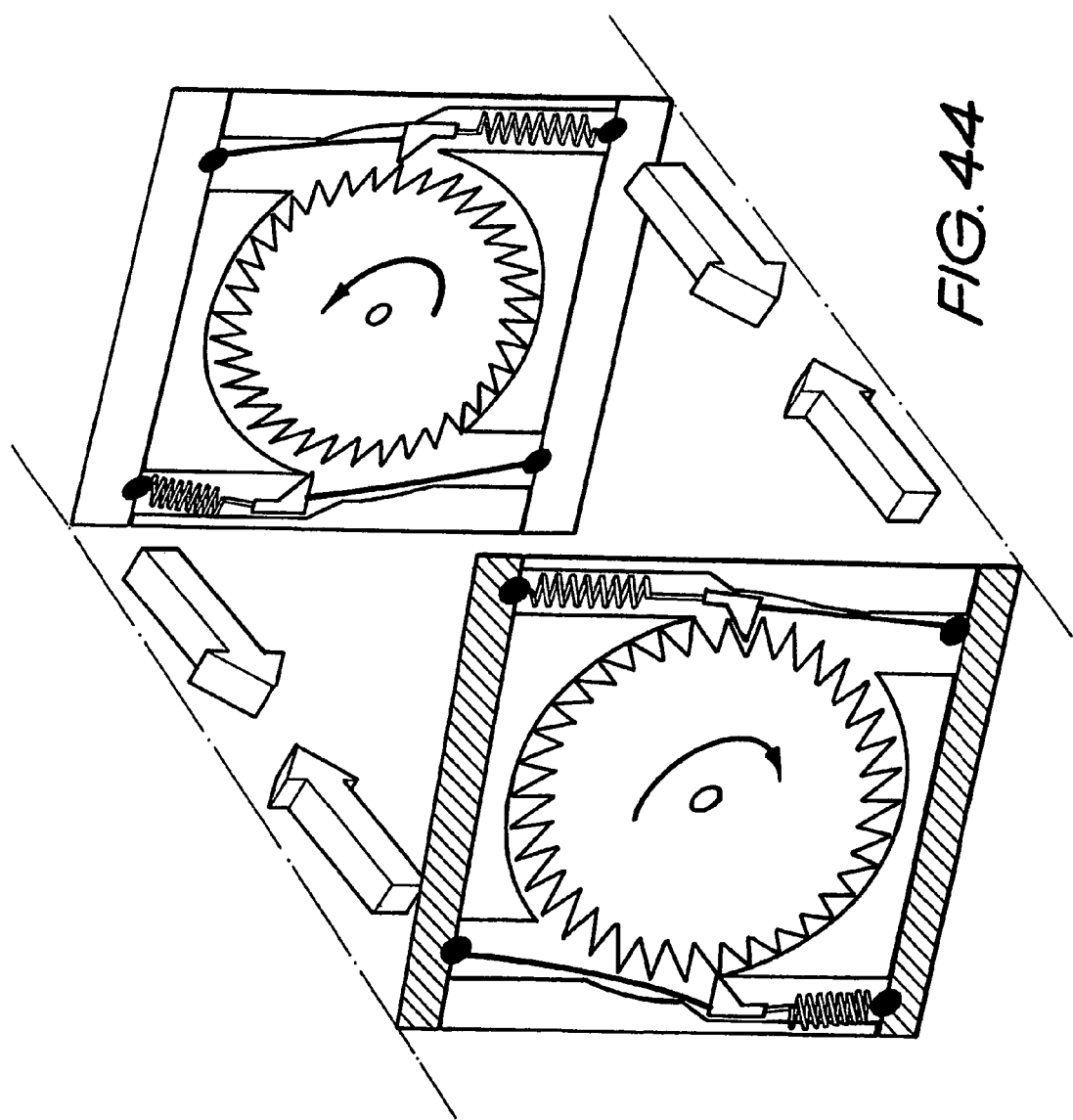
FIG. 44 is a diagrammatic representation of two unidirectional incremental rotary actuators, showing how they may be combined to form a single BIRA.

The feature that makes this actuator "bi-directional" is demonstrated in FIG. 44. If a single actuator sub-unit (being the jagged disk, hooks units and housing) is reversed, it may actuate in reverse direction. Hence two of these sub-units can be coupled together (by reversing one and binding the disks concentrically together) to provide the ability to actuate both clockwise and anti-clockwise.

It must be noted that care must be taken during activation to only power one sub-unit at a time, otherwise the actuator will be counterproductive at best, and damaged at worse (due to wires failing or breaking).

CPM

The TAM, TAM-SAM and TENDON CPM devices will be applied to people post-hand trauma and post hand surgery.

Additionally the devices are suitable for improving and maintaining normal properties of the hand in patients suffering from spinal injury, burns, stroke, edema, peripheral nerve injury and the onset of arthritis. Also the systems can be used to produce hand grasp and release. This can be implemented by an external switch activated by the user (this might be achieved by a button press or another volitional user control signal). In cases of individuals with weak grips, the activation can be triggered by the actual active grip (i.e. the glove senses the movement of the fingers and activated to strengthen their forces).

The mechanical design of the actuators are not restricted to hand CPM only. The same idea can be used to create CPM devices for other joints in the body including the elbow, wrist and knee.

FPT

The force-position transducer may be used in many other applications where small force/position controlled movements are required. An example may be an automatic door, where a small but powerful actuator coupled to the FPT can provide feedback on the position of the actuator as well as any forces encountered (i.e. obstructions to the door movement)

ACTUATORS

The actuators described are not limited to CPM devices. There are many devices which can benefit from the use of such actuators (including medical and non-medical devices). These actuators are light weight, silent and very strong. They have been designed to address the limitation of movement available in prior art.

The invention will now be further described with reference to a number of examples, for the electromechanical actuators.

EXAMPLE 1

For the purpose of demonstrating characteristics of electromechanical actuators of the invention, a number of actuators were prepared and tested using polypyrrole polymer with hexafluorophosphate ($PF_6^-$) as a dopant as indicated below.

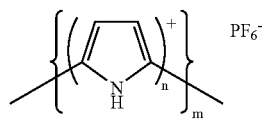

wherein n=2-4, and m=the number of repeat units of the polymer.

Specifically, the actuators were prepared:

(a) as a strip by electrodeposition onto a platinum (Pt) plate from a solution containing 0.06 M pyrrole and 0.05 M PPy/$PF_6$ in propylene carbonate at a current density of 0.15 mA/cm$^2$;

(b) as a tube but with no helical wire conductor using the method described above with reference to FIG. 9 and the solution and electrochemical conditions as for the preparation of the strip actuator in (a) above;

(c) as a tube with a helical wire conductor using the method described above with reference to the FIG. 9 and using the solution and electrochemical conditions as for the preparation of the strip actuator as in (a) above.

The tube configuration results in improved electronic, mechanical and electrochemical properties as summarised below in Table 1. Mean values are shown.

TABLE 1

Characteristics of tube actuator compared to flat film actuator

| | Tube (no helix) (PPy/$PF_6$) | Flat Film (PPy/$PF_6$) |
|---|---|---|
| Conductivity (Scm$^{-1}$) | 170 | 85 |
| Tensile strength (MPa) | 23 | 6.0 |
| Elongation to break (%) | 17 | 8.0 |
| Electrolytic efficiency (%) | 10 | 5.0 |

The electrochemical efficiency of the tube configuration compared to the flat film indicates that more of the tube is electrochemically accessible than the corresponding strip. However, even with the tube configuration, enhanced electrolytic efficiency and actuation was obtained with just one and then both ends of the tube connected to the short wire inserts 104 and 105 suggesting improved electrical connection with the polymer was obtained utilising the wire inserts as indicated in Table 2.

TABLE 2

Characteristics of tube actuator with and without helical conductor

| | Tube (no helix) One end connected (PPy/$PF_6$) | Tube (no helix) Both ends connected (PPy/$PF_6$) |
|---|---|---|
| Electrolytic efficiency (%) | 3.5 | 5.0 |
| Stroke (strain) (%) | 0.23 | 0.33 |
| Stroke rate (%/sec) | 0.48 | 0.67 |

EXAMPLE 2

A number of tube actuators of the invention incorporating helical conductors were prepared and the performance of three samples is shown in Table 3.

Resistance of the actuators were measured after locating wire inserts 104 and 105 in each end of the polymer tube, respectively.

All the polymer helices were between 45 and 55 mm long.

All polymer helices tested were from the same batch and prepared under a current density of 0.15 mA/cm$^2$ for 24 hours.

A platinum (Pt) wire helix was used with a pitch of 25 turns/cm.

TABLE 3

Comparison of characteristics between the actuators with helical conductor

| Polymer Helix | Resistance (Ω)* | Strain (%) | Strain rate (%/sec) |
|---|---|---|---|
| Helix 2 | 4-8 | 0.7 | 1.4 |
| Helix 3 | 4-8 | 0.8 | 1.6 |
| Helix 5 | 4-8 | 0.8 | 1.6 |

In all cases, the inclusion of the helical wire in the actuator resulted in improved electrochemical and actuator performance. By forming the conductor wire into a helix, the wire is able to readily extend and contract in length with expansion and reduction of the volume of the polymer tube.

EXAMPLE 3

Figure 10:
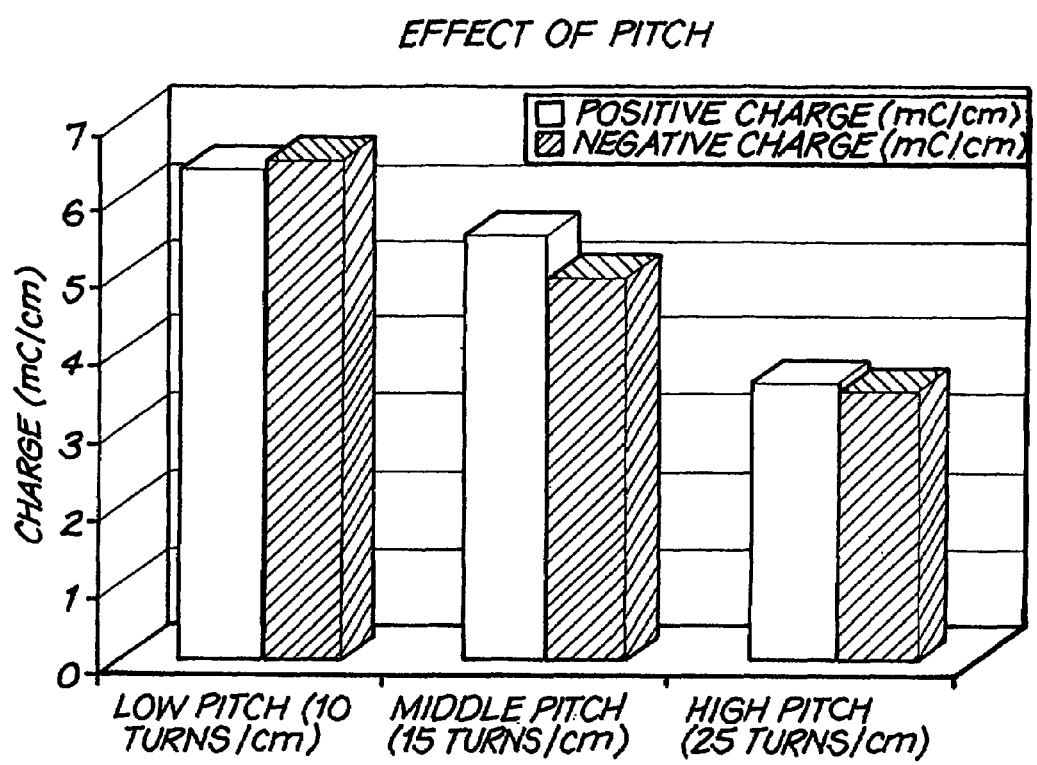
FIG. 10 is a graph showing charges transported by electromechanical actuators of the present invention against pitch of the helix of a conductor of the respective actuators.

The effect of the pitch of the helical wire on actuator performance was investigated. (Detail how the results were obtained.) The results set out in Table 4 suggests use of low pitch provides better performance as indicated by the increase in strain obtained. The increase in strain at lower pitch is in agreement with the increase in electrochemical efficiency at lower pitch as indicated in FIG. 10.

TABLE 4

Effects of pitch of helical conductor on strain under different applied frequencies
Strain (%)

| Operating Frequency | Low Pitched (10 turns/cm) | High Pitched (25 turns/cm) |
|---|---|---|
| 10.0 Hz | 0.10 | 0.1 |
| 5.0 Hz | 0.28 | 0.1 |
| 2.0 Hz | 0.38 | 0.2 |
| 1.0 Hz | 0.67 | 0.16 |
| 0.5 Hz | 1.0 | 0.1 |

REFERENCES CITED

1. M. R. Gandhi, P. Murray, G. M. Spinks, and G. G. Wallace, "Mechanism of electromechanical actuation in polypyrrole," *Synth. Met.* 73, pp. 247-256, 1995.
2. R H. Baugbman, "Conducting polymer artificial muscles," *Synth Met.* 78, pp. 339-353, 1996.
3. T. W. Lewis, L. A. P. Kane-Maguire, A. S. Hutchison, G. M. Spinks, and G. G. Wallace, "development of an all polymer axial force electrochemical actuator," *Synth. Met.* 102, pp. 1317-1318, 1999.
4. G. G. Wallace, G. M. Spinks, and P. R. Teasdale, "Conductive Electroactive Polymers: Intelligent Materials Systems, Technomic, Lancaster, 1997.
5. P. Murray, G. M. Spinks, G. G. Wallace, and R. P. Burford, *Synth. Met.* 97, pp. 117, 1998.
6. R. Baughman et. Al., *Science.* 284, pp. 1340, 1999.

The invention claimed is:

1. A movement device comprising movement facilitation devices capable of being coupled to a patient, so as to facilitate independent movement of at least two joints of a limb or digit, said movement device comprising:
    a) at least a first and a second movement facilitation device, the first movement facilitation device being disposed so as to facilitate a first movement of a corresponding first joint of said limb or digit, the second movement facilitation device being disposed so as to facilitate a second movement of a corresponding second joint of said limb or digit, wherein the first movement can be performed independently of the second movement, and each of the movement facilitation devices comprising:
        an actuator capable of causing the corresponding joint to move,
        operating means coupled to the actuator for operating the actuator in response to an input signal,
        a sensor capable of providing a corresponding feedback signal relating to at least one quantity selected from the group consisting of a force exerted on the corresponding joint, a force exerted by the corresponding joint, a position of the corresponding joint, a pressure exerted on the corresponding joint and a pressure exerted by the corresponding joint, and
        a support structure coupled to the actuator and capable of being coupled to the patient's body such that, when coupled to the patient's body, the support structure is disposed so that the actuator is capable of causing the corresponding joint to move; and
    b) controlling means capable of providing an input signal to one of the operating means for controlling said operating means;
    wherein each sensor is capable of providing the corresponding feedback signal to means selected from the corresponding operating means and the controlling means so as to affect the operation of one of the actuators,
    wherein each sensor comprises a force-position transducer for generating the corresponding feedback signal, and
    wherein the transducer comprises:
        a) a radiation source and one or more detectors capable of detecting radiation from the radiation source, wherein at least one detector is free to move relative to the radiation source, and
        b) a return mechanism coupled to at least one detector, wherein at least one detector is capable of generating the corresponding feedback signal, wherein said feedback signal is dependent on an intensity of the radiation from the radiation source incident on said detector, said feedback signal relating to at least one quantity selected from the group consisting of a force exerted on the corresponding joint, a force exerted by the corresponding joint, a position of the corresponding joint, a pressure exerted on the corresponding joint and a pressure exerted by the corresponding joint.

2. The movement device of claim 1 wherein the radiation is selected from the group consisting of light, infra-red, magnetic, ultrasonic and electromagnetic radiation.

3. A method for monitoring at least one parameter selected from the group consisting of the position of a joint and a force exerted by the joint comprising:
    a) securing to at least a portion of the patient's body proximate the joint a movement device comprising:
        an actuator capable of causing the joint to move,
        operating means coupled to the actuator for operating the actuator in response to an input signal,
        a sensor capable of providing at least one feedback signal relating to a quantity selected from the group consisting of a force exerted on the joint, a force exerted by the joint, a position of the joint, a pressure exerted on the joint and a pressure exerted by the joint,
        a support structure coupled to the actuator and capable of being coupled to the patient's body such that, when coupled to the patient's body, the support structure is disposed so that the actuator is capable of causing the joint to move, and
        controlling means coupled to the operating means for controlling the operating means,
    wherein the sensor comprises a transducer comprising a radiation source and one or more detectors capable of detecting radiation from the radiation source wherein at least one detector is free to move relative to the radiation source, and a return mechanism coupled to the one or more detectors, wherein each of the one or more detectors is capable of generating one of the at least one feedback signals, wherein said feedback signal is dependent on an intensity of the radiation incident on said detector;
    b) causing the joint to apply a force;
    c) monitoring the intensity of the intensity of radiation incident on the or each detector; and
    d) using the intensity of radiation to determine at least one parameter selected from the group consisting of the position of the joint and the force exerted by the joint.

* * * * *

UNITED STATES PATENT AND TRADEMARK OFFICE
CERTIFICATE OF CORRECTION

PATENT NO. : 7,481,782 B2  Page 1 of 1
APPLICATION NO. : 10/526713
DATED : January 27, 2009
INVENTOR(S) : Scott et al.

It is certified that error appears in the above-identified patent and that said Letters Patent is hereby corrected as shown below:

On the cover page, item (75) inventors, replace

Timothy Roderick Dalkeith Scott, New South Wales (AU); Veronica A. Vare, New South Wales (AU); Peter Puya Abolfathi; New South Wales (AU); Gordon G. Wallace, New South Wales (AU); Dezhi Zhou, New South Wales (AU)

with

Timothy Roderick Dalkeith Scott, New South Wales (AU); Veronica A. Vare, New South Wales (AU); Peter Puya Abolfathi

Signed and Sealed this

Nineteenth Day of May, 2009

JOHN DOLL
*Acting Director of the United States Patent and Trademark Office*